US 9,389,454 B2

(12) United States Patent
Yamaguchi et al.

(10) Patent No.: US 9,389,454 B2
(45) Date of Patent: Jul. 12, 2016

(54) LIQUID CRYSTAL LENS, METHOD OF DRIVING LIQUID CRYSTAL LENS, LENS UNIT, CAMERA MODULE, AND CAPSULE TYPE MEDICAL DEVICE

(71) Applicant: ORTUS TECHNOLOGY CO., LTD., Tokyo (JP)

(72) Inventors: Minoru Yamaguchi, Hamura (JP); Mamoru Yoshida, Kunitachi (JP)

(73) Assignee: ORTUS TECHNOLOGY CO., LTD., Tokyo (JP)

( * ) Notice: Subject to any disclaimer, the term of this patent is extended or adjusted under 35 U.S.C. 154(b) by 15 days.

(21) Appl. No.: 13/943,422

(22) Filed: Jul. 16, 2013

(65) Prior Publication Data

US 2014/0028924 A1    Jan. 30, 2014

Related U.S. Application Data

(63) Continuation of application No. PCT/JP2012/050870, filed on Jan. 17, 2012.

(30) Foreign Application Priority Data

Jan. 17, 2011   (JP) .................................. 2011-007236
Oct. 21, 2011   (JP) .................................. 2011-231667

(51) Int. Cl.
*G02F 1/1335*   (2006.01)
*G03B 17/56*   (2006.01)
(Continued)

(52) U.S. Cl.
CPC ........ *G02F 1/133526* (2013.01); *A61B 1/0019* (2013.01); *A61B 1/00096* (2013.01);
(Continued)

(58) Field of Classification Search
CPC ............. A61B 1/00096; A61B 1/0019; A61B 1/00193; A61B 1/041; G02B 13/0075; G03B 17/565; G02F 1/29; G02F 1/134309; G02F 2203/28; G02F 1/1347; G02F 1/13471
See application file for complete search history.

(56) References Cited

U.S. PATENT DOCUMENTS

2003/0008135 A1\*   1/2003   Kawamura .......... G02F 1/13439
                                                                        428/336
2007/0100200 A1\*   5/2007   Suzuki et al. ................. 600/101
(Continued)

FOREIGN PATENT DOCUMENTS

CN          101395523          3/2009
CN          101625498          1/2010
(Continued)

OTHER PUBLICATIONS

PCT International Preliminary Report on Patentability mailed Jul. 25, 2013 in corresponding International Application No. PCT/JP2012/050870.
(Continued)

*Primary Examiner* — Ryan Crockett

(57) ABSTRACT

A liquid crystal lens includes a first liquid crystal cell, a second liquid crystal cell, and an intermediate layer sandwiched therebetween. The first liquid crystal cell includes a pair of a first transparent substrate and a second transparent substrate, a first liquid crystal layer, and a first electrode. The second liquid crystal cell includes a pair of a third transparent substrate and a fourth transparent substrate, a second liquid crystal layer aligned in a direction perpendicular to the first liquid crystal layer, and a second electrode. The intermediate layer includes a high dielectric constant layer and a third electrode including one or a plurality of opening portions.

27 Claims, 45 Drawing Sheets

(51) Int. Cl.
  *G02F 1/29* (2006.01)
  *A61B 1/04* (2006.01)
  *G02B 13/00* (2006.01)
  *A61B 1/00* (2006.01)
  *G02F 1/1343* (2006.01)
  *G02F 1/1347* (2006.01)

(52) U.S. Cl.
  CPC ............. *A61B1/00193* (2013.01); *A61B 1/041* (2013.01); *G02B 13/0075* (2013.01); *G02F 1/29* (2013.01); *G03B 17/565* (2013.01); *G02F 1/13471* (2013.01); *G02F 1/134309* (2013.01); *G02F 2203/28* (2013.01)

(56) References Cited

U.S. PATENT DOCUMENTS

| | | | | |
|---|---|---|---|---|
| 2007/0229754 | A1* | 10/2007 | Galstian | G02F 1/29 349/200 |
| 2007/0284627 | A1* | 12/2007 | Kimura | 257/257 |
| 2008/0136990 | A1* | 6/2008 | Kimura | 349/46 |
| 2010/0053539 | A1* | 3/2010 | Lin | G02F 1/13 349/200 |
| 2010/0060824 | A1* | 3/2010 | Sakai et al. | 349/74 |
| 2010/0289941 | A1 | 11/2010 | Ito et al. | |
| 2010/0307319 | A1* | 12/2010 | Kani | 84/485 R |
| 2011/0043742 | A1* | 2/2011 | Cavanaugh | 349/153 |
| 2011/0069151 | A1* | 3/2011 | Orimoto | 348/42 |
| 2011/0090415 | A1* | 4/2011 | Asatryan et al. | 349/33 |
| 2011/0181797 | A1* | 7/2011 | Galstian et al. | 349/2 |
| 2012/0019761 | A1* | 1/2012 | Nystrom | G02F 1/1345 349/139 |
| 2012/0188490 | A1* | 7/2012 | Zohrabyan et al. | 349/96 |
| 2012/0242924 | A1* | 9/2012 | Galstian | 349/54 |
| 2013/0169920 | A1* | 7/2013 | Wada | G02B 3/14 349/200 |
| 2013/0314632 | A1* | 11/2013 | Zohrabyan et al. | 349/36 |
| 2014/0036183 | A1* | 2/2014 | Asatryan et al. | 349/33 |
| 2014/0049682 | A1* | 2/2014 | Galstian et al. | 348/356 |
| 2015/0198830 | A1 | 7/2015 | Galstian et al. | |

FOREIGN PATENT DOCUMENTS

| | | |
|---|---|---|
| EP | 2 161 616 A2 | 3/2010 |
| JP | 5-53089 A | 3/1993 |
| JP | 11-305262 | 11/1999 |
| JP | 2000-81600 | 3/2000 |
| JP | 2001-95756 | 4/2001 |
| JP | 2001-170002 | 6/2001 |
| JP | 2002-49043 | 2/2002 |
| JP | 2004-4616 | 1/2004 |
| JP | 2004-248753 | 9/2004 |
| JP | 2006-78650 | 3/2006 |
| JP | 2006-138950 | 6/2006 |
| JP | 2006-227036 | 8/2006 |
| JP | 2007-256473 | 10/2007 |
| JP | 2008-233628 | 10/2008 |
| JP | 2009-128555 | 6/2009 |
| JP | 2009-188973 | 8/2009 |
| JP | 2009-528558 | 8/2009 |
| JP | 2010-113029 | 5/2010 |
| JP | 2010-172119 | 8/2010 |
| JP | 2010-204447 | 9/2010 |
| JP | 2010-211084 | 9/2010 |
| JP | 2011-7236 | 1/2011 |
| JP | 2011-525251 | 9/2011 |
| KR | 10-0832897 | 5/2008 |
| WO | 2007/098602 | 9/2007 |
| WO | WO 2009/153764 | 12/2009 |
| WO | WO 2009/153764 A2 | 12/2009 |
| WO | WO 2011/075834 | 6/2011 |

OTHER PUBLICATIONS

International Search Report mailed Mar. 6, 2012 in corresponding International Application No. PCT/JP2012/050870.
Extended European Search Report dated Oct. 26, 2015 from European Patent Application No. 12736896.7, 13 pages.
Chinese Office Action dated Apr. 23, 2015 in corresponding Chinese Patent Application No. 201280005630.7.
Partial European Search Report dated Jun. 19, 2015 in corresponding European Patent Application No. 12736896.7.
Ye et al., "Double-Layer Liquid Crystal Lens", Japanese Journal of Applied Physics, vol. 43, No. 3A, 2004, pp. L352-L354.
Extended European Search Report dated Oct. 26, 2015 from European Patent Application No. EP App. No. 12736896.7, 13 pages.
Japanese Office Action dated Jan. 5, 2016 from Japanese Patent Application No. 2012-553736, 13 pages.

* cited by examiner

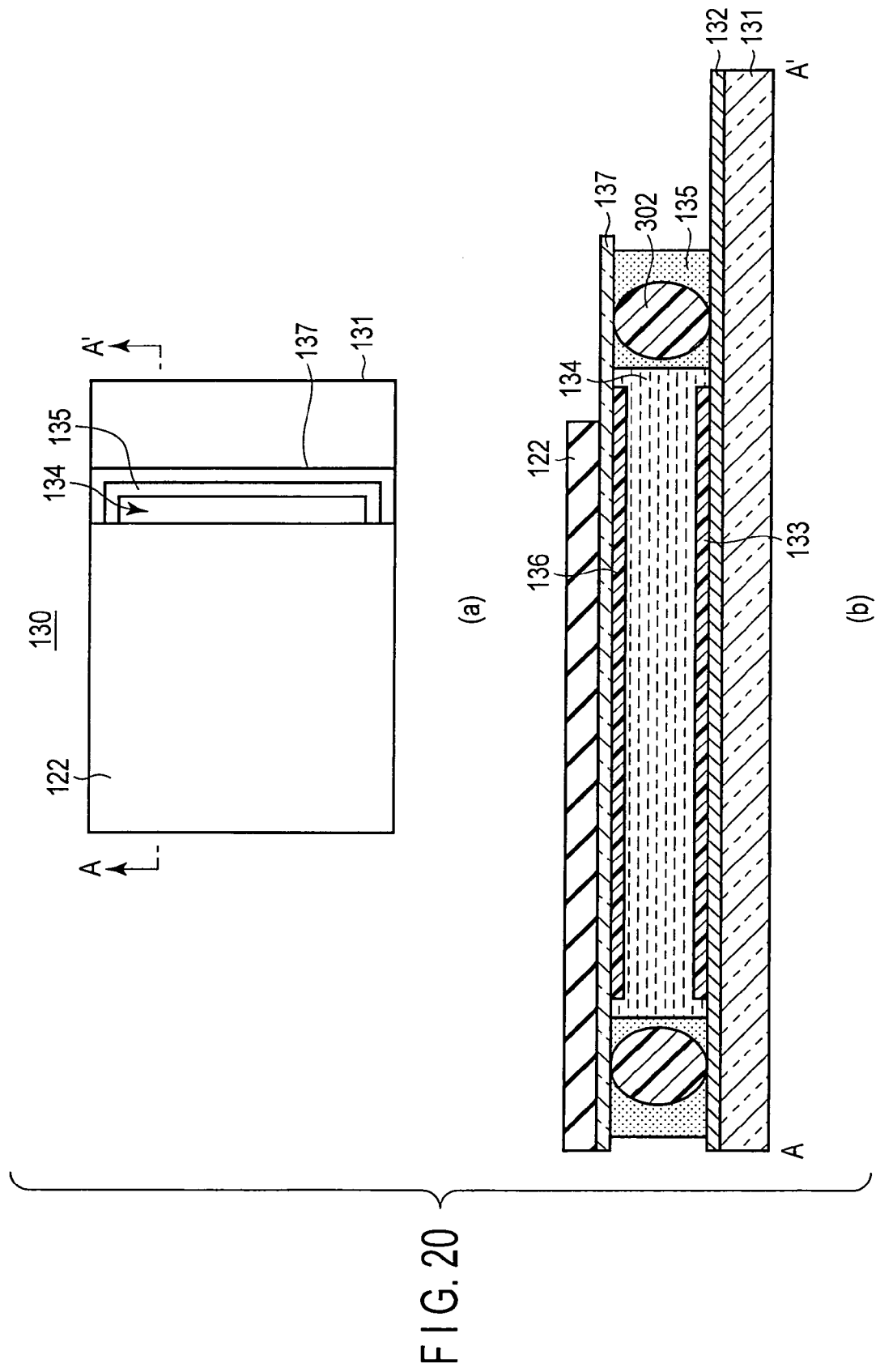
F I G. 20

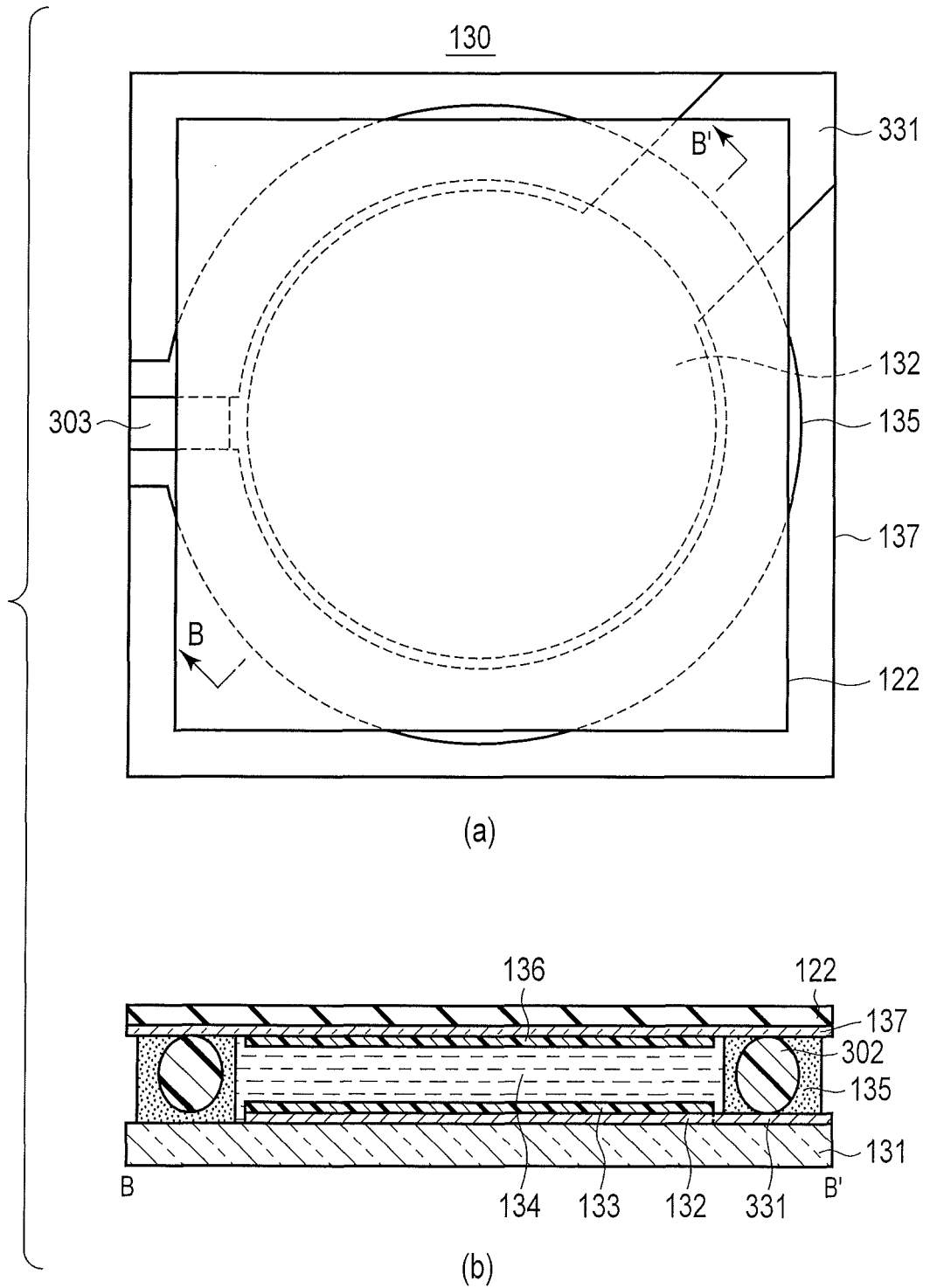
F I G. 33

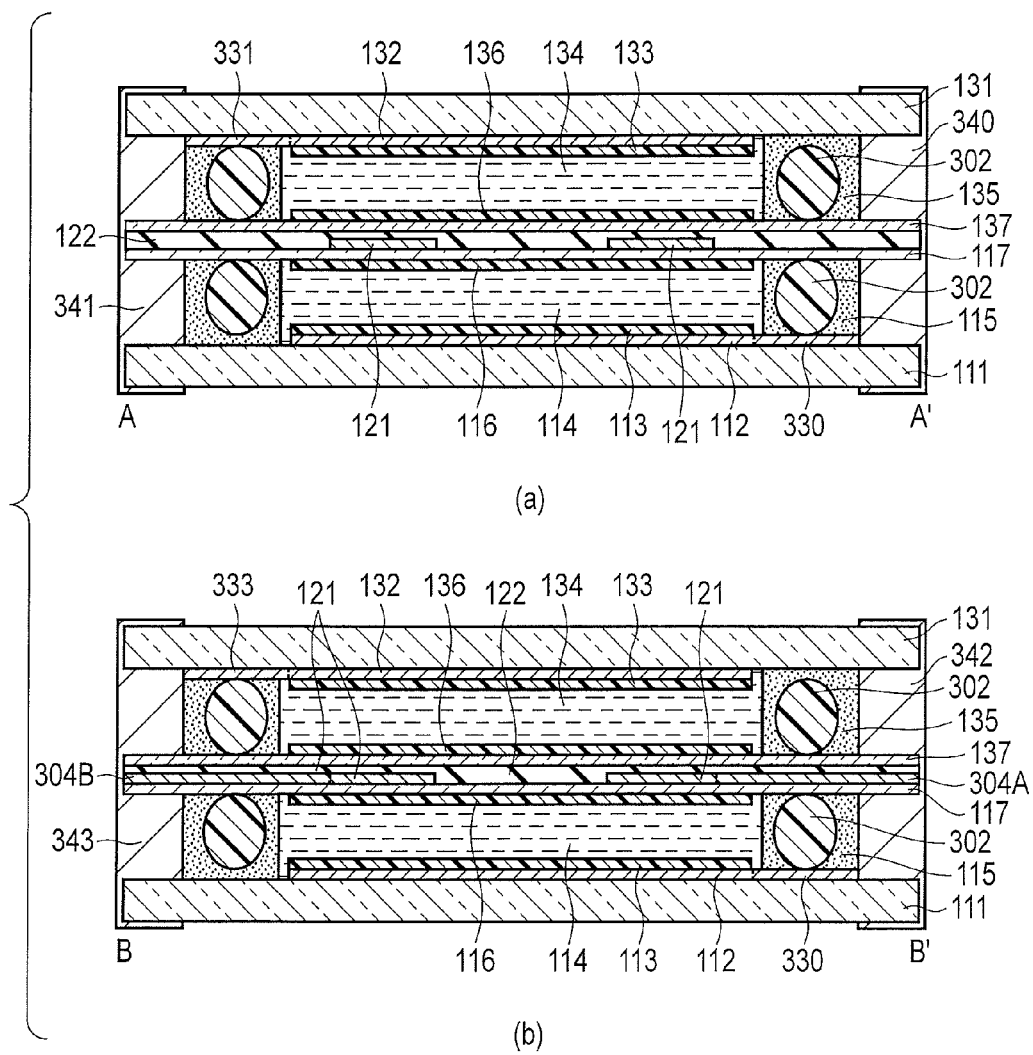
F I G. 37

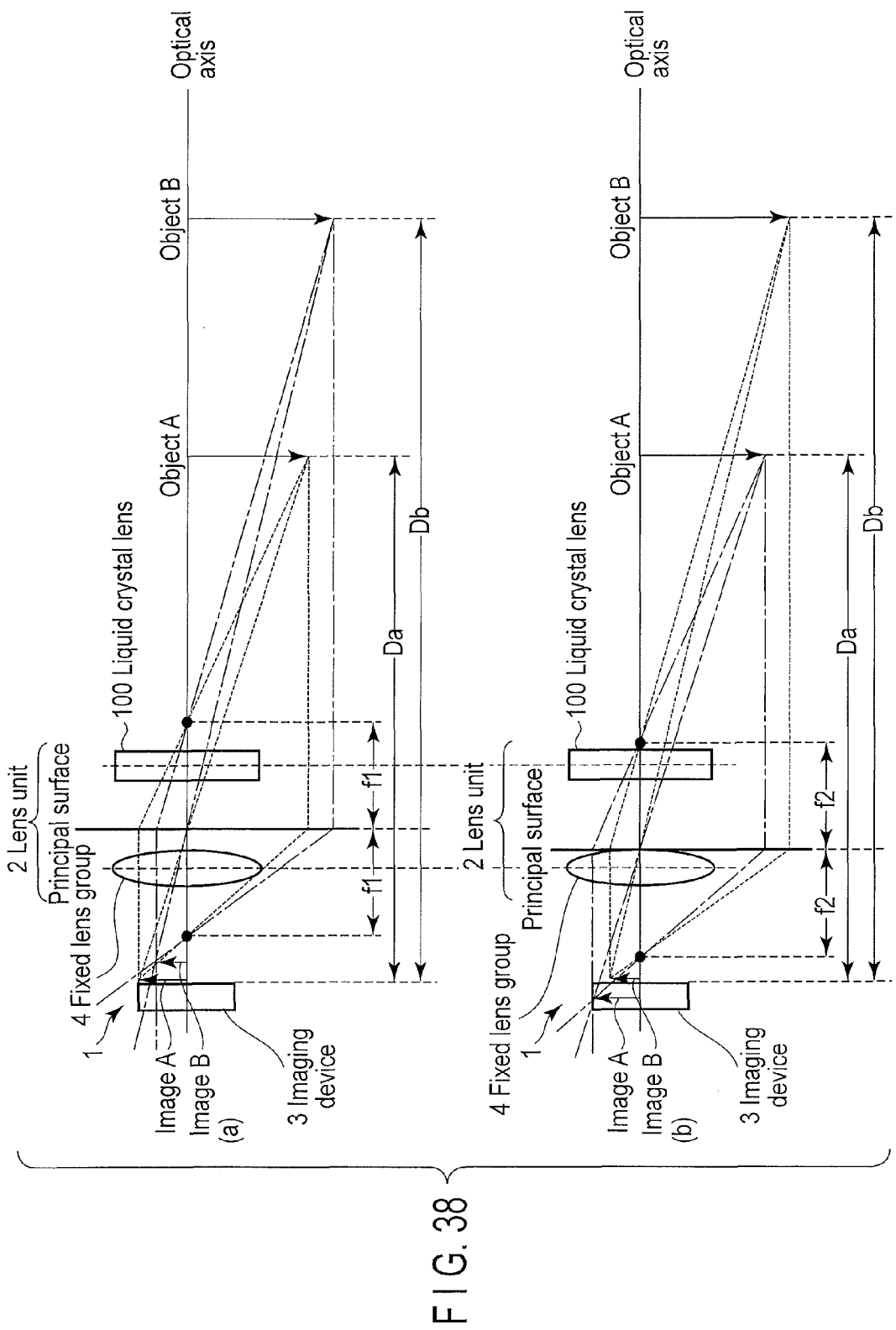
F I G. 38

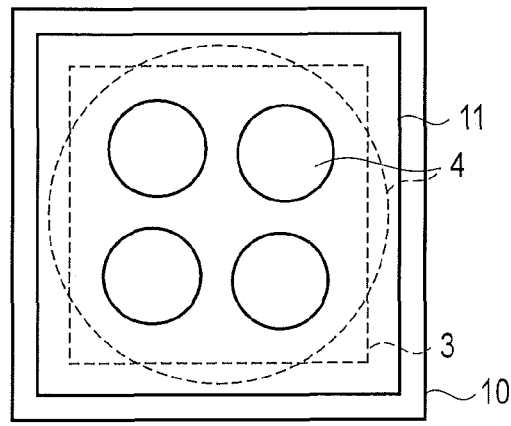
F I G. 48
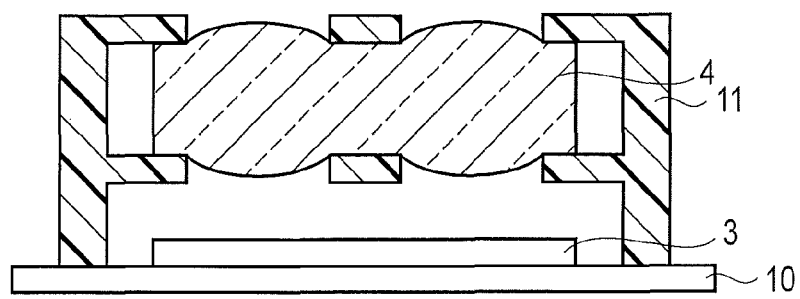
F I G. 49
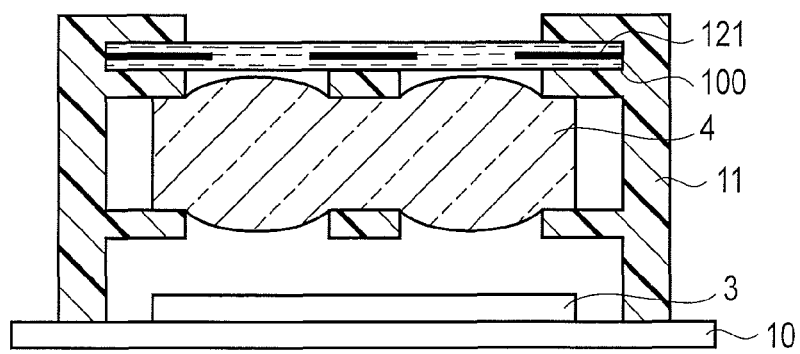
F I G. 50

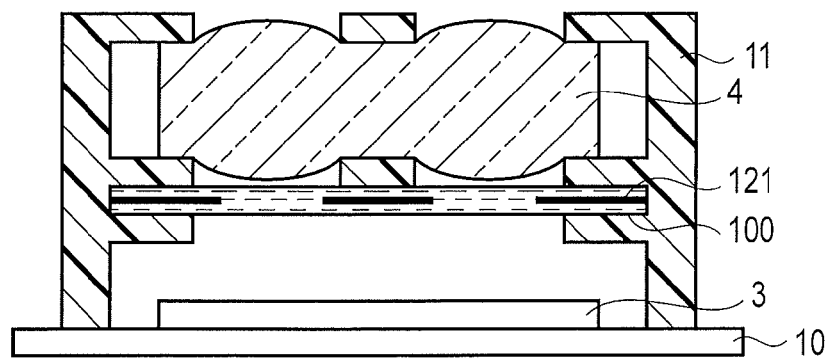
F I G. 51
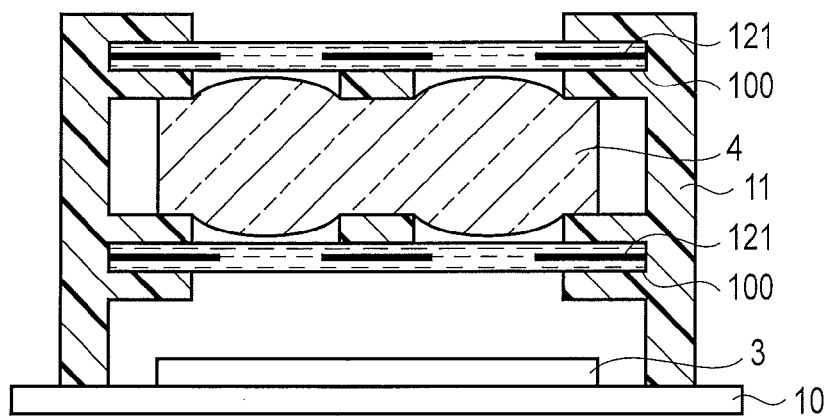
F I G. 52
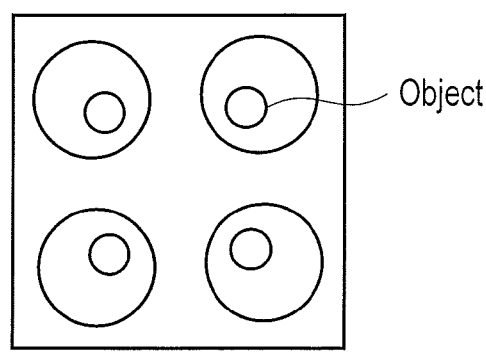
F I G. 53

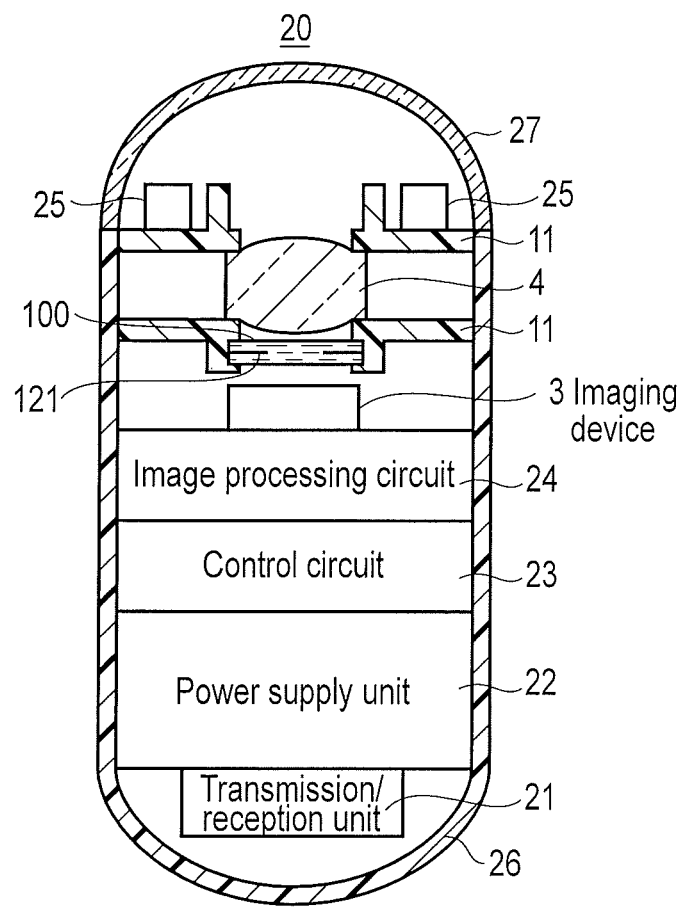
F I G. 56

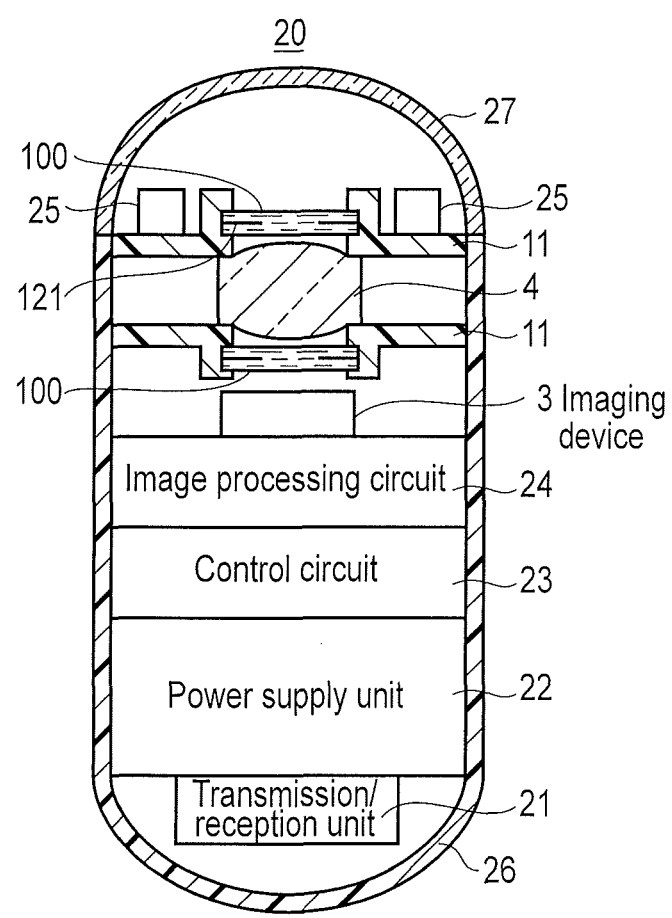
F I G. 57

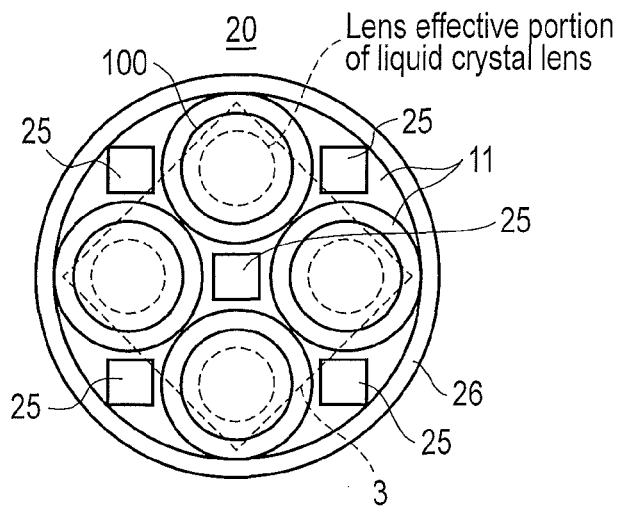
F I G. 58
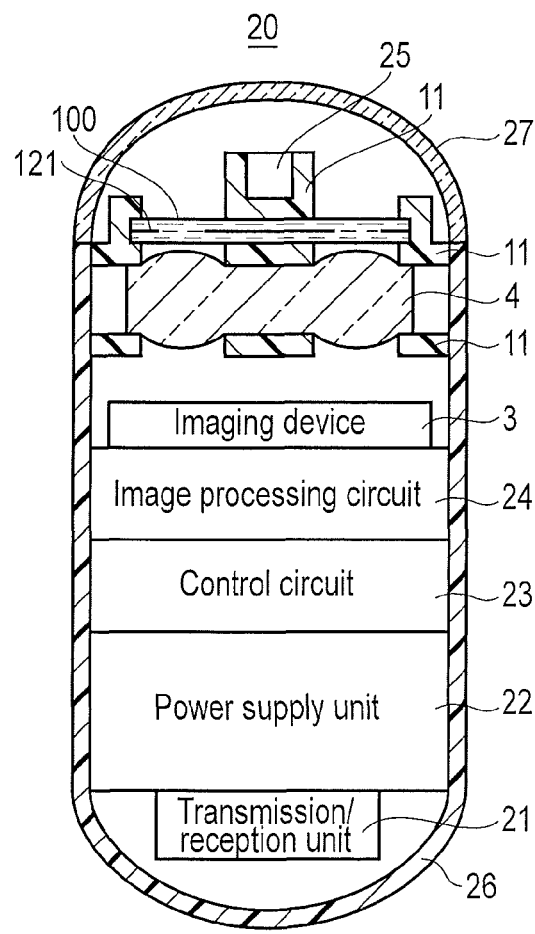
F I G. 59

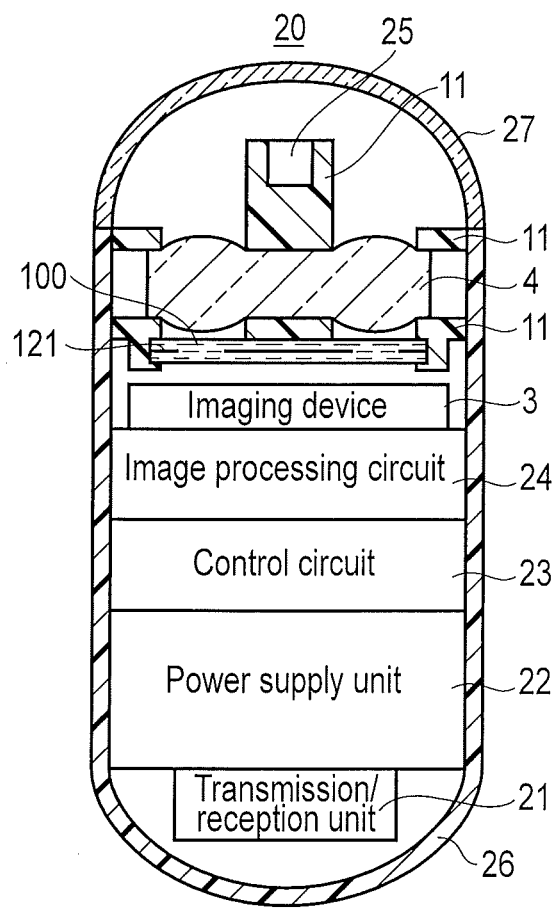
F I G. 60

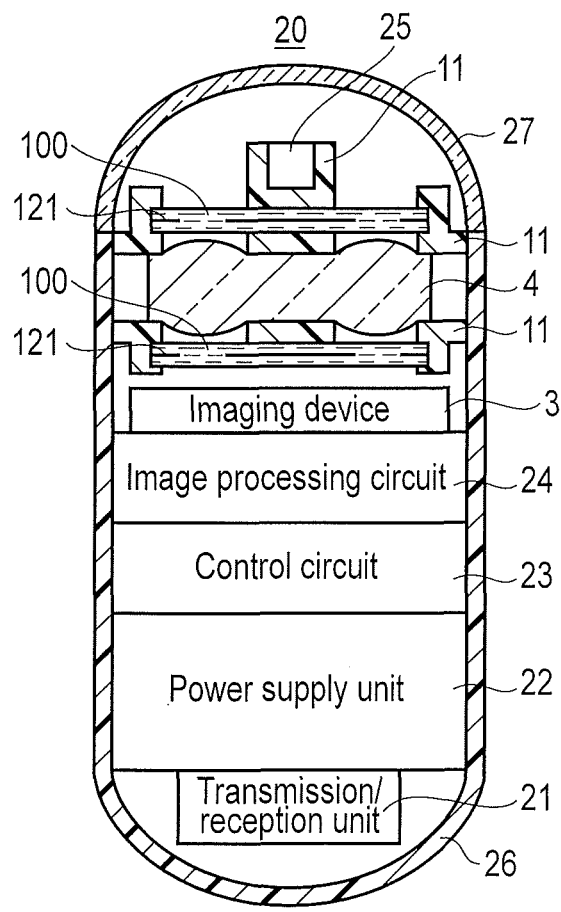
F I G. 61
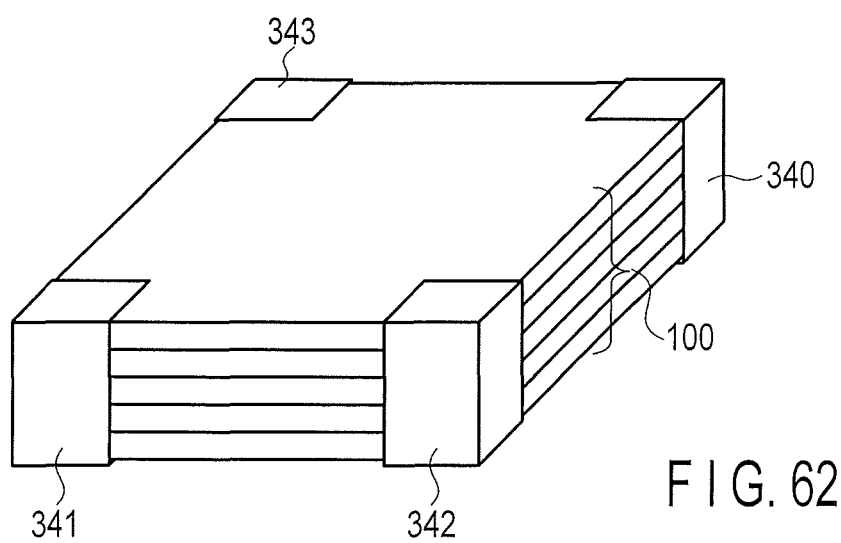
F I G. 62

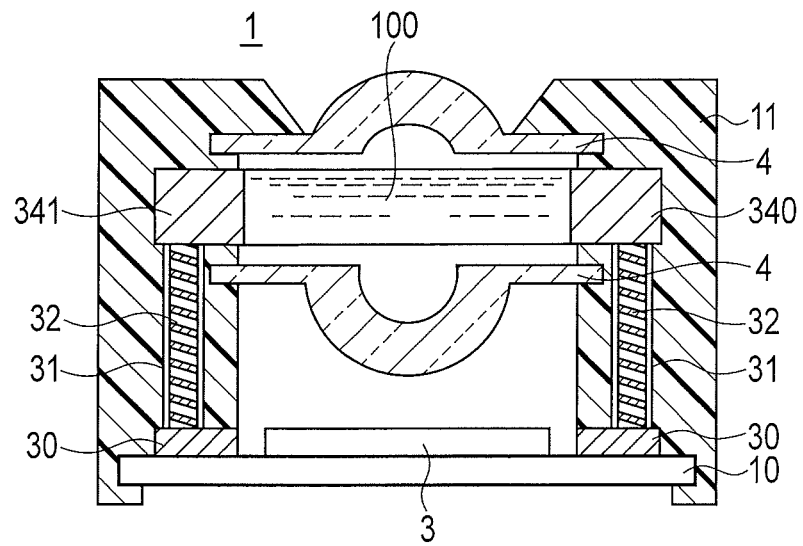
F I G. 65
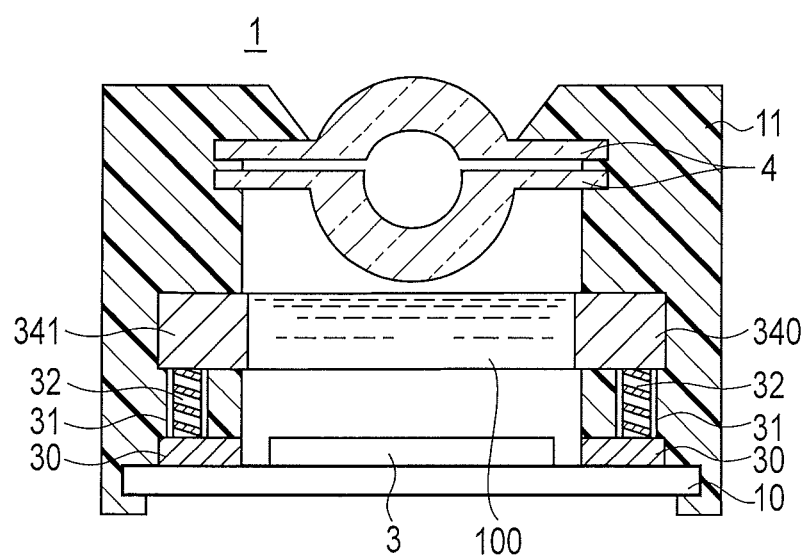
F I G. 66

LIQUID CRYSTAL LENS, METHOD OF DRIVING LIQUID CRYSTAL LENS, LENS UNIT, CAMERA MODULE, AND CAPSULE TYPE MEDICAL DEVICE

CROSS REFERENCE TO RELATED APPLICATIONS

This application is a Continuation Application of PCT Application No. PCT/JP2012/050870, filed Jan. 17, 2012 and based upon and claiming the benefit of priority from prior Japanese Patent Applications No. 2011-007236, filed Jan. 17, 2011; and No. 2011-231667, filed Oct. 21, 2011, the entire contents of all of which are incorporated herein by reference.

BACKGROUND OF THE INVENTION

1. Field of the Invention

The present invention relates to a liquid crystal lens which can change a focal length in accordance with an electrical signal and a method of driving the liquid crystal lens. The present invention further relates to a lens unit including the liquid crystal lens, a camera module, and a capsule type medical device.

2. Description of the Related Art

A liquid crystal lens is expected to be applied to the autofocus function of a camera, an optical pickup device, and the like by advantageously utilizing the ability to electrically control the focus length of the lens. A conventional autofocus function has used a scheme of moving the position of the lens by using a voice coil motor. However, using a liquid crystal lens capable of changing its focal length eliminates a mechanical movable portion, leading to the downsizing and power saving of a lens unit.

Liquid crystal lenses are disclosed in, for example, patent literatures 1 and 2. The liquid crystal lenses disclosed in these literatures each are designed to use concentrically patterned transparent electrodes to form applied voltage gradients from the center of the lens to its periphery. This lens functions by changing the average tilt angle of liquid crystal molecules.

When using such a structure, it is necessary to use a lead wire pattern, which impairs rotational symmetry, to extract outside concentric electrodes on the central portion of the lens. This inevitably causes lens distortion. In addition, a fine transparent electrode pattern existing on a portion through which light from the lens passes has a refractive index that is too high to be ignored as compared with those of a glass substrate and liquid crystal. This causes scattering and reflection of light at a pattern end, which in turn interferes with imaging. According to the above literatures, it is necessary to finely control the voltages applied to many electrodes. This requires a complex driving circuit.

According to another example of the above literatures, a current is supplied to the patterned transparent electrodes to form voltage gradients applied to the liquid crystal through a voltage drop across a resistor. In this case, although voltage control is simple, the power consumption increases for driving operation.

Recently, as a compact camera module incorporated in a cellular phone or the like, a product added with a focus adjustment function and an angle-of-view adjustment function has been on the market. The focus adjustment function and the angle-of-view adjustment function are implemented by spatially moving some lenses in the lens unit using a voice coil motor and the like. This scheme, however, requires a mechanism for spatially moving lenses, and hence it is difficult to implement downsizing.

Medical practices conducted in medical fields use endoscopes capable of capturing stereoscopic images. An endoscope used in this case is, for example, a straight tube type endoscope using a fiber. Furthermore, a capsule type medical device incorporating a compact camera module has been on the market. The capsule type medical device can image the digestive organs of an object such as the small intestine and large intestine by being swallowed via the mouth. A capsule type medical device which captures a stereoscopic image of the digestive organ has also been researched and developed but has not been put into practice. One of the reasons for this is that it is very difficult to install two or more compact camera modules in a limited space.

Incorporating a fly-eye lens unit in a capsule type medical device can obtain a plurality of images having parallaxes necessary for stereoscopic image capturing. Using these images can generate a stereoscopic image of an observation region. Observing the stereoscopic image makes it possible to closely observe the surface state, e.g., irregularity, of a morbid region. This makes accurate examination and treatment possible.

Studies have also been made on a technique of transmitting driving power from outside the body to a capsule type medical device by a noncontact power transmission technique such as an electromagnetic induction scheme. At this time, there is a risk that strong electromagnetic waves may affect components in the capsule type medical device. In particular, the voice coil motor of a compact camera module incorporated in the capsule type medical device malfunctions due to the influence of the magnetic field generated by strong electromagnetic waves. As a consequence, the focus adjustment function and the angle-of-view adjustment function fail to accurately function.

BRIEF SUMMARY OF THE INVENTION

According to an aspect of the present invention, there is provided a liquid crystal lens comprising:

a first liquid crystal cell including a pair of a first transparent substrate and a second transparent substrate, a first liquid crystal layer sandwiched between the first transparent substrate and the second transparent substrate, and a first electrode arranged between the first transparent substrate and the first liquid crystal layer;

a second liquid crystal cell including a pair of a third transparent substrate and a fourth transparent substrate, a second liquid crystal layer sandwiched between the third transparent substrate and the fourth transparent substrate and aligned in a direction perpendicular to the first liquid crystal layer, and a second electrode arranged between the fourth transparent substrate and the second liquid crystal layer; and an intermediate layer including a high dielectric constant layer sandwiched between the first liquid crystal cell and the second liquid crystal cell so as to be in contact with the second transparent substrate and the third transparent substrate, and a third electrode including one or a plurality of opening portions.

According to an aspect of the present invention, there is provided a method of driving the liquid crystal lens, comprising:

grounding the third electrode;

applying a first alternating voltage and a second alternating voltage to the first electrode and the second electrode, respectively; and changing a focal length of the liquid crystal lens by changing a phase difference between the first alternating voltage and the second alternating voltage.

According to an aspect of the present invention, there is provided a lens unit comprising:

the liquid crystal lens; and a fixed lens arranged on an optical axis of the liquid crystal lens and having a fixed focal length, wherein a focal point or an angle of view is adjusted by changing the focal length of the liquid crystal lens.

According to an aspect of the present invention, there is provided a camera module comprising:

the lens unit;

an imaging device configured to receive light from the lens unit; and a control circuit configured to control the liquid crystal lens and the imaging device.

According to an aspect of the present invention, there is provided a capsule type medical device comprising:

the lens unit;

an imaging device configured to receive light from the lens unit;

a control circuit configured to control the liquid crystal lens and the imaging device; and a capsule configured to seal the lens unit, the imaging device, and the control circuit.

BRIEF DESCRIPTION OF THE SEVERAL VIEWS OF THE DRAWING

FIG. 20 shows a step of manufacturing the liquid crystal lens following the step in FIG. 19;

FIG. 33 shows a step of manufacturing the liquid crystal lens following the step in FIG. 32;

FIG. 37 shows sectional views taken along a line A-A' and a line B-B' in FIG. 36 and showing a step of manufacturing the liquid crystal lens;

FIG. 38 shows the arrangement of a camera module having a focus adjustment function according to the seventh embodiment;

FIG. 48 is a plan view showing the arrangement of a multieye camera module according to Example 1;

FIG. 49 is a sectional view showing the arrangement of a multieye camera module according to Example 1;

FIG. 50 is a sectional view showing the arrangement of a multieye camera module according to Example 2;

FIG. 51 is a sectional view showing the arrangement of a multieye camera module according to Example 3;

FIG. 52 is a sectional view showing the arrangement of a multieye camera module according to Example 4;

FIG. 53 is a view for explaining an image captured by the multieye camera module;

FIG. 56 is a sectional view showing the arrangement of a capsule type medical device according to Example 2;

FIG. 57 is a sectional view showing the arrangement of a capsule type medical device according to Example 3;

FIG. 58 is a top view showing the arrangement of a multi-eye capsule type medical device according to the 10th Embodiment;

FIG. 59 is a sectional view showing the arrangement of a multieye capsule type medical device according to Example 1;

FIG. 60 is a sectional view showing the arrangement of a multieye capsule type medical device according to Example 2;

FIG. 61 is a sectional view showing the arrangement of a multieye capsule type medical device according to Example 3;

FIG. 62 is a perspective view schematically showing a liquid crystal lens;

FIG. 65 is a sectional view showing another example of the arrangement of the camera module; and FIG. 66 is a sectional view showing still another example of the arrangement of the camera module.

DETAILED DESCRIPTION OF THE INVENTION

Figure 1:
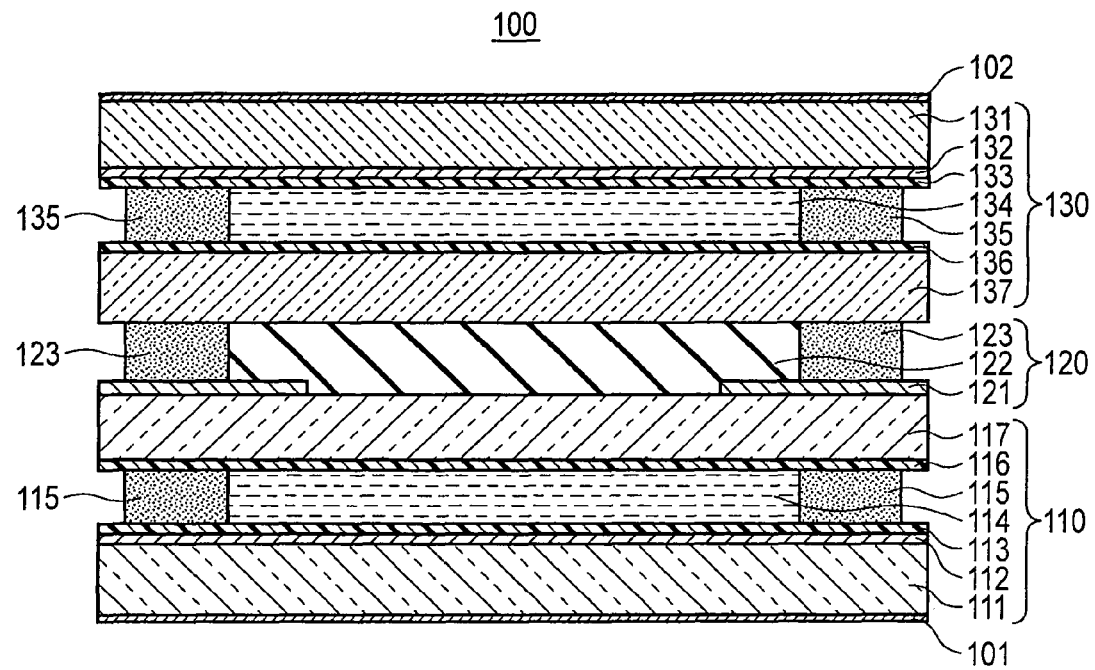
FIG. 1 is a sectional view showing the arrangement of a liquid crystal lens 100 according to the first embodiment.

The embodiments of the present invention will be described below with reference to the accompanying drawings. Note that the drawings are schematic and conceptual, and the dimensions, ratios, and the like in the respective drawings are not necessary the same as those in reality. In addition, even the same portion may be shown in a different dimensional relationship or with different ratios in different drawings. Several embodiments to be described below represent examples of apparatuses and methods for embodying the technical idea of the present invention, and the technical idea of the present invention is not specified by the shapes, structures, and layouts of the constituent parts. The technical idea of the present invention can be embodied by modifying constituent elements without departing from the gist of the invention. Note that in the following explanation, the same reference numerals denote elements having the same functions and arrangements, and a repetitive explanation will be made only when necessary.

[First Embodiment]

FIG. 1 is a sectional view showing the arrangement of a liquid crystal lens 100 according to the first embodiment of the present invention. The liquid crystal lens 100 includes a first liquid crystal cell 110, a second liquid crystal cell 130, and an intermediate layer 120 sandwiched between the cells.

The first liquid crystal cell 110 includes a pair of transparent substrates 111 and 117 formed from, for example, glass substrates, an electrode 112, a pair of alignment films 113 and 116, and a liquid crystal layer 114. The electrode 112 is provided on the transparent substrate 111. The electrode 112 is formed from a transparent conductive material having optical transparency, e.g., ITO (Indium-Tin Oxide).

The alignment film 113 is provided on the electrode 112. The alignment film 116 is provided on the surface of the transparent substrate 117 which faces the transparent substrate 111. The liquid crystal layer 114 is sandwiched between the alignment films 113 and 116. The liquid crystal material forming the liquid crystal layer 114 changes its optical characteristics as the aligning direction of the liquid crystal molecules is operated in accordance with the electric field applied to the material. Aligning treatments have been performed on the surfaces of the alignment films 113 and 116 which are in contact with the liquid crystal layer 114 to decide the aligning direction of the liquid crystal molecules without any applied electric field (in an initial alignment state).

A seal member 115 is provided between the alignment films 113 and 116 in contact with them. As the seal member 115, an adhesive mixed with spherical silica or cylindrical glass particles is used. The seal member 115 surrounds the outer edge portion of the lens portion in the circumferential direction. The seal member 115 has a function of holding the liquid crystal layer 114 to a predetermined thickness, a function of sealing the liquid crystal material of the liquid crystal layer 114, and a function of bonding the transparent substrates 111 and 117. As the seal member 115, for example, an adhesive resin such as an acrylic-based adhesive or epoxy-based adhesive is used. Alternatively, it is possible to use a resin which can be molded by being irradiated with light, for example, a photo curing resin (e.g., an acrylic-based photo curing resin) or a resin which can be molded by heat, for example, a heat setting resin (e.g., an epoxy-based heat setting resin).

The second liquid crystal cell 130 includes a pair of transparent substrates 131 and 137 formed from, for example, glass substrates, an electrode 132, a pair of alignment films 133 and 136, and a liquid crystal layer 134.

The electrode 132 is provided on the transparent substrate 131. The electrode 132 is formed from a transparent conductive material having optical transparency, e.g., the same material as that used for the electrode 112.

The alignment film 133 is provided on the electrode 132. The alignment film 136 is provided on the surface of the transparent substrate 137 which faces the transparent substrate 111. The liquid crystal layer 134 is sandwiched between the alignment films 133 and 136. The liquid crystal material forming the liquid crystal layer 134 changes its optical characteristics as the aligning direction of the liquid crystal molecules is operated in accordance with the electric field applied to the material. Aligning treatments have been performed on the surfaces of the alignment films 133 and 136 which are in contact with the liquid crystal layer 134 to decide the aligning direction of the liquid crystal molecules without any applied electric field.

A seal member 135 is provided between the alignment films 133 and 136 in contact with them. As the seal member 135, for example, the same material as that used for the seal member 115 is used. The seal member 135 surrounds the outer edge portion of the lens portion in the circumferential direction. The seal member 135 has a function of holding the liquid crystal layer 134 to a predetermined thickness, a function of sealing the liquid crystal material of the liquid crystal layer 134, and a function of bonding the transparent substrates 131 and 137.

The intermediate layer 120 is provided between the first liquid crystal cell 110 and the second liquid crystal cell 130. The first liquid crystal cell 110 is disposed such that the transparent substrate 117 is in contact with the intermediate layer 120. The second liquid crystal cell 130 is disposed such that the transparent substrate 137 is in contact with the intermediate layer 120.

The intermediate layer 120 includes an electrode 121 and a high dielectric constant layer (high-k layer) 122. The electrode 121 has, for example, a circular opening portion serving as a lens aperture (lens effective region), and is, for example, a ring-like electrode made of a conductive material. The opening portion of the electrode 121 may have a shape other than a circular shape as long as the liquid crystal lens 100 functions as a lens. The electrode 121 is, for example, disposed in contact with the transparent substrate 117. The position of the electrode 121 is not specifically limited. The electrode 121 may be disposed in contact with the transparent substrate 137 or may be buried in the intermediate portion of the high-k layer 122.

The high-k layer 122 is provided between the transparent substrate 117 and the transparent substrate 137 and between the electrode 121 and transparent substrate 137. The high-k layer 122 is made of a transparent insulating material. The relative dielectric constant of the high-k layer 122 is larger than that of the glass material for the transparent substrate, preferably two times or more that of the glass material. More specifically, if the relative dielectric constant of the glass material is about 5, the relative dielectric constant of the high-k layer 122 preferably falls within the range of 10 or more to 50 or less. Satisfying these conditions can form the liquid crystal lens 100 having a predetermined aperture. Note that it is possible to increase the aperture of the liquid crystal lens 100 by increasing the relative dielectric constant of the high-k layer 122 and increasing the thickness of the high-k layer 122 or increasing one of them.

A seal member 123 is provided between the electrode 121 and the transparent substrate 137 in contact with them. The same material as that used for the seal member 115 is used for the seal member 123. The seal member 123 surrounds the outer peripheral portion of the lens portion in the circumferential direction. The seal member 123 has a function of holding the high-k layer 122 to a predetermined thickness, a function of sealing the high-k layer 122, and a function of bonding the electrode 121 and the transparent substrate 137. Note that it is possible to use, instead of the seal member 115, a spacer for adjusting the distance between the electrode 121 and the transparent substrate 137. The spacer 123 is formed from, for example, a plastic or glass material.

In order to prevent unnecessary scattered light and reflected light in the lens, the interface between the high-k layer 122 and the transparent substrate 117 (or 137) preferably has a low reflectance. For this reason, the refractive index of the high-k layer 122 is set to a value close to or lower than that of the transparent substrates 117 and 137, with which it is in contact, or that of the electrodes 112 and 132. More specifically, the refractive index of the high-k layer 122 is set to be equal to or more than that of the transparent substrate 117 (or 137) and equal to or less than that of the electrode 112 (or 132). If the glass material for the transparent substrates 117 and 137 has a refractive index of about 1.5, in order to reduce the reflection of light at the interface between the glass substrates, the high-k layer 122 preferably has a refractive index of 2.0 or less.

An antireflection film 101 is provided on the opposite surface of the transparent substrate 111 to the surface on which the electrode 112 is provided. Likewise, an antireflection film 102 is provided on the opposite surface of the transparent substrate 131 to the surface on which the electrode 132 is provided. As the antireflection films 101 and 102, for example, a thin magnesium fluoride film or a thin multilayer film formed from titanium oxide, silicon oxide, and the like is used. Resin films coated with antireflection films may be bonded instead of the antireflection films 101 and 102.

In this case, the liquid crystal layer 114 has homogeneous alignment such that the long axes of liquid crystal molecules are parallel to the in-plane direction (the direction along the transparent substrate surface) and the long axis directions coincide with the first direction (X direction). The dielectric constant anisotropy of the homogeneously aligned liquid crystal layer is positive. As described above, the alignment films 113 and 116 and an alignment process step control the alignment of the liquid crystal layer 114. The liquid crystal layer 134 has homogeneous alignment such that the long axes of liquid crystal molecules are parallel to the in-plane direction and the long axis directions coincide with the second direction (Y direction) perpendicular to the X direction. As described above, the alignment films 133 and 136 and an alignment process step control the alignment of the liquid crystal layer 134.

Figure 2:
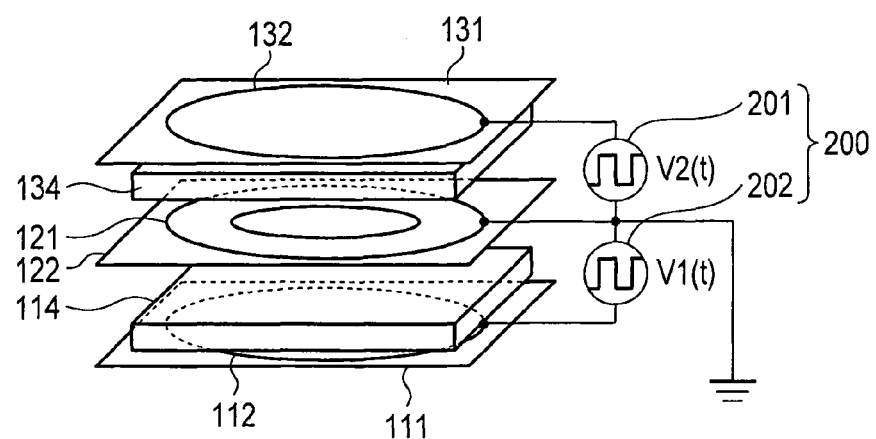
FIG. 2 is a schematic view showing the arrangement of a voltage control circuit 200 which applies voltages to the liquid crystal lens 100.

FIG. 2 is a schematic view showing the arrangement of a voltage control circuit 200 which applies voltages to the liquid crystal lens 100. The voltage control circuit 200 includes a first voltage control circuit 201 which applies voltages to the electrode 112 of the first liquid crystal cell 110 and a second voltage control circuit 202 which applies a voltage to the electrode 132 of the second liquid crystal cell 130. The electrode 121 is grounded. The operation of the voltage control circuit 200 will be described later.

EXAMPLE

An example of the liquid crystal lens 100 will be described below.

The liquid crystal layers 114 and 134 each have a thickness of about 50 μm. The transparent substrates (glass substrates) 117 and 137 each have a thickness of about 50 μm. Glass has a relative dielectric constant of about 5. Although the transparent substrates (glass substrates) 111 and 131 each have a thickness of about 500 μm, the thickness can be arbitrarily set because it is irrelevant to the operation of the liquid crystal lens 100. Although 50-μm thick glass substrates may be used as the glass substrates 117 and 137 from the beginning, it is possible to use a glass substrate having a thickness of, for example, 500 μm at an early stage and decrease it to 50 μm by etching or polishing after the substrate is bonded to the glass substrate 111 or 131.

The electrode 121 is formed from a thin conductive film and has an inside diameter of about 1.5 mm. The electrode 121 is formed by forming a thin metal film made of chromium (Cr) or the like on the glass substrate 117 and then processing the thin metal film by photolithography or by printing and calcining a conductive ink. As a material for the electrode 121, it is preferable to use a carbon-based conductive ink, e.g., an ink having low reflectance with respect to light, like a conductive resin containing graphite particles. Using a black conductive material for the electrode 121 will reduce unnecessary light reflected by the electrode 121 and improve the imaging characteristics of the liquid crystal lens 100.

The high-k layer 122 is made of, for example, propylene carbonate. Since propylene carbonate is a liquid, air bubbles do not easily enter the material in a manufacturing process. This material facilitates manufacturing steps as compared with a solid insulating film. In addition, since the high-k layer 122 can be formed in the same manufacturing step as that for a liquid crystal, it is possible to reduce the manufacturing cost. The high-k layer 122 has a thickness of about 50 µm and a relative dielectric constant of about 20. The high-k layer 122 may be formed by coating a material obtained by dispersing fine particles of a ferroelectric material containing barium titanate as a main component in a resin binder and curing the material with heat or ultraviolet light (UV).

(Operation)

Figure 3:
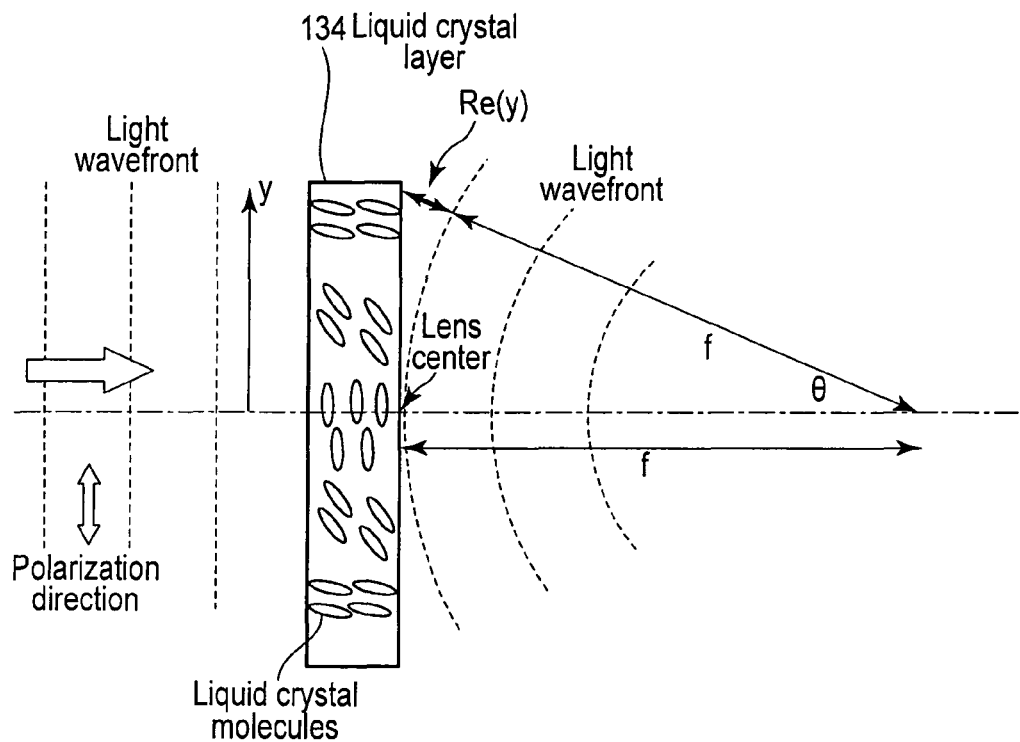
FIG. 3 is a sectional view for explaining the operation principle of the liquid crystal lens 100.

The operation principle of the liquid crystal lens 100 will be described first. FIG. 3 is a sectional view for explaining the operation principle of the liquid crystal lens 100. FIG. 3 shows the liquid crystal layer 134 functioning as a lens in an extracted state.

An inhomogeneous electric field is applied to the homogeneously aligned liquid crystal layer 134 to form an alignment distribution such that the average tilt angle of the long axes of the liquid crystal molecules is small at the lens center and gradually increases toward the lens peripheral portion. When planar waves enter the liquid crystal layer 134, optical path differences occur between the lens center and the lens peripheral portion due to the refractive index anisotropy of the liquid crystal layer 134, and light passing through the liquid crystal layer 134 has a curved wavefront.

Referring to FIG. 3, reference symbol "y" denotes the height (radius) from the lens center; "f", the focal length; and "Re(y)", the optical path difference between the lens center and a position on the radius y. Re(y) is represented by "Δn×d", where "Δn" is a refractive index anisotropy and "d" is the thickness of the liquid crystal layer.

The radius y and the optical path difference Re(y) are respectively represented by $$f \tan \theta = y \quad (1)$$

$$f(\sec \theta - 1) = Re \quad (2)$$

Eliminating θ from equations (1) and (2) will establish $$1/f = 2Re/(y^2 - Re^2) \approx 2Re/y^2 \quad (3)$$

"1/f" is a lens power.

Equation (3) is rewritten to express Re(y) as follows:

$$Re(y) \approx y^2/2f \quad (4)$$

The liquid crystal layer 134 is operated to cause the optical path difference Re(y) proportional to the square of the radius y according to mathematical expression (4).

Figure 4:
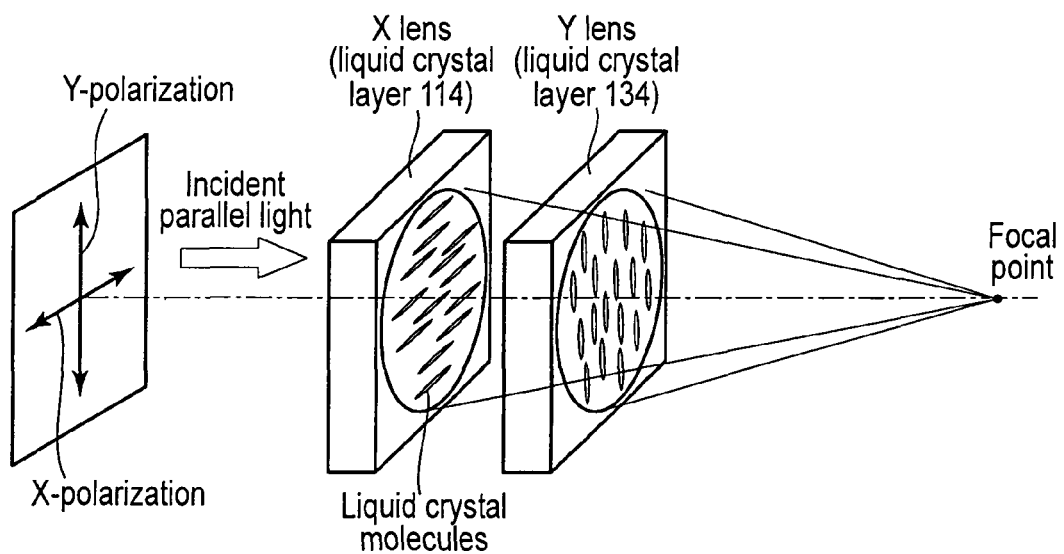
FIG. 4 is a perspective view for explaining the operation principle of the liquid crystal lens 100.

The single liquid crystal layer 134 acts on only polarized light in one direction. For this reason, in order to form a liquid crystal lens effective for polarized light in all directions, the two liquid crystal layers 114 and 134 in which the aligning directions of the liquid crystal molecules are perpendicular to each other may be used in combination, as shown in FIG. 4. This can perform control to make light passing through the liquid crystal layers 114 and 134 have a spherical wavefront, and hence light passing through the liquid crystal lens 100 focuses on one point on the optical axis. That is, the arrangement shown in FIG. 4 functions as a convex lens. The liquid crystal layer 114 functions as an X lens which acts on polarized light in the X direction. The liquid crystal layer 134 functions as a Y lens which acts on polarized light in the Y direction.

Applying voltage gradients to the liquid crystal layers 114 and 134 will align liquid crystal (e.g., nematic liquid crystal) molecules each having an elongated rod-like shape such that the long axes are aligned in the electric field direction. As a result, as the alignment distributions on the liquid crystal layers 114 and 134 change, the refractive index distribution changes from the lens center to the lens peripheral portion. This allows the liquid crystal layers 114 and 134 to function as a lens. It is possible to freely change the refractive index distributions on the liquid crystal layers 114 and 134 by controlling the manner of applying voltages to the electrodes 112, 121, and 132. This makes it possible to control the optical characteristics of the convex lens.

A technique of obtaining a smooth voltage gradient from the lens center of the liquid crystal lens 100 to the lens peripheral portion will be described next.

Figure 5:
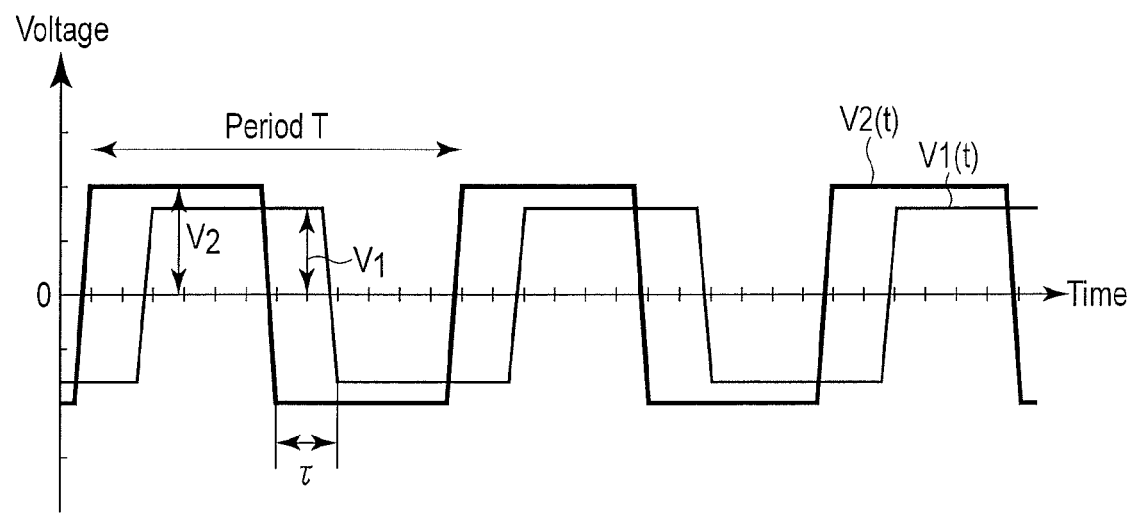
FIG. 5 is a graph for explaining the voltage control operation of the voltage control circuit 200.

FIG. 5 is a graph for explaining the voltage control operation of the voltage control circuit 200.

The voltage control circuit 201 applies an alternating voltage (alternating current voltage) V1(t) with a rectangular waveform which has a single-sided amplitude V1 and a period T to the electrode 112. The voltage control circuit 202 applies an alternating voltage V2(t) with a rectangular waveform which has a single-sided amplitude V2 and the period T to the electrode 132. Let τ be a phase shift time between the voltage V1(t) and the voltage V2(t). The voltages V1(t) and (V2(t) have the same period T.

The voltage control circuit 201 can control the single-sided amplitude V1, period T, and phase of the voltage V1(t). Likewise, the voltage control circuit 202 can control the single-sided amplitude V2, period T, and phase of the voltage V2(t). The magnitudes of the single-sided amplitudes V1 and V2 are properly controlled to make the electric fields applied to the liquid crystal layers 114 and 134 have the same magnitude. As shown in FIG. 1, in the first embodiment, the distance between the electrodes 132 and 121 becomes larger than that between the electrodes 112 and 121. In the case shown in FIG. 5, in order to correct this distance difference, the single-sided amplitude V2 is larger than the single-sided amplitude V1.

Figure 6:
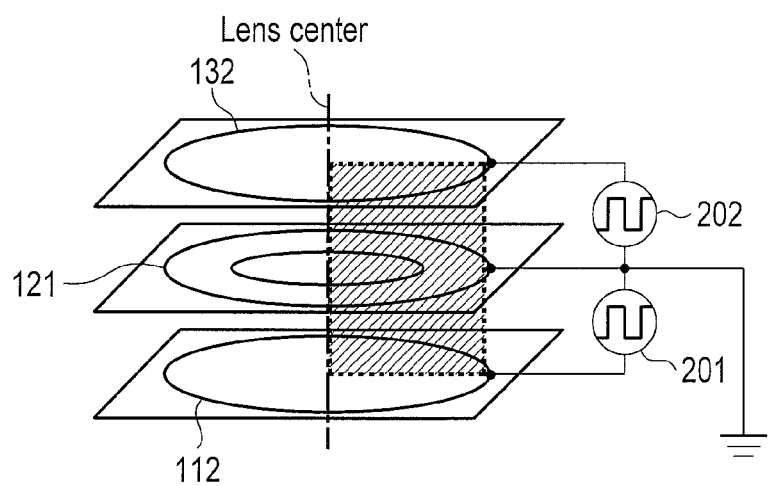
FIG. 6 is a view for explaining a region where a voltage distribution is numerically simulated.
Figure 7:
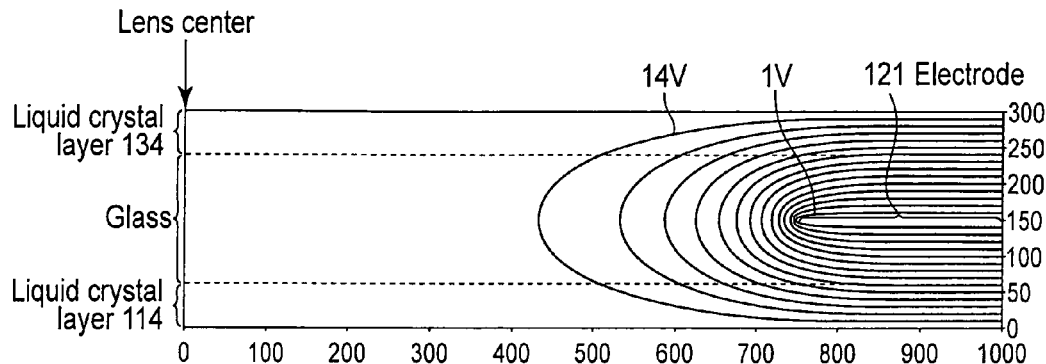
FIG. 7 is a view for explaining a voltage distribution on a liquid crystal lens according to a comparative example.
Figure 8:
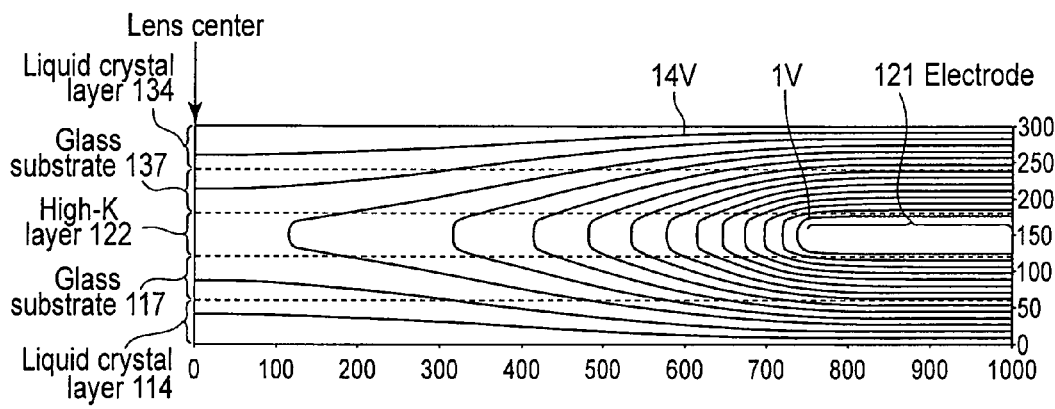
FIG. 8 is a view for explaining a voltage distribution on the liquid crystal lens 100 upon application of in-phase voltages.
Figure 9:
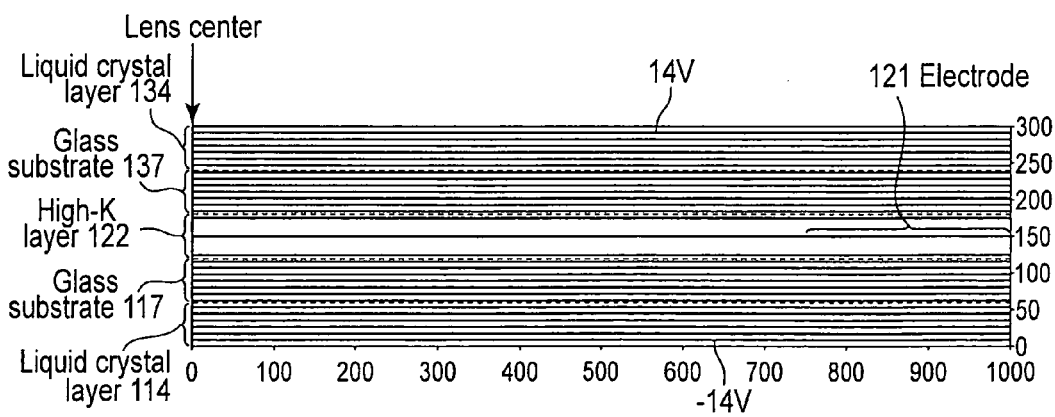
FIG. 9 is a view for explaining a voltage distribution on the liquid crystal lens 100 upon application of opposite-phase voltages.

FIGS. 7 to 9 each show the voltage distribution on a section of the liquid crystal lens 100 which is obtained by numerical simulation. FIGS. 7 to 9 each show the voltage distribution on the sectional portion indicated by the hatching in FIG. 6, i.e., a half region of a lens section. The units on the ordinate and the abscissa in each of FIGS. 7 to 9 are [µm]. V1=V2=15 V. The interval between equipotential lines is 1 V. Note that the voltage distributions shown in FIGS. 8 and 9 use the numerical values associated with the liquid crystal lens 100 described in the above embodiment.

FIG. 7 shows equipotential lines in a case in which voltages defined by V1(t)=V2(t) are applied, i.e., the voltage V1(t) is in phase with the voltage V2(t), and the arrangement includes no high-k layer. Referring to FIG. 7, for example, a glass material is used instead of a high-k layer, and hence the gap between the liquid crystal layers 114 and 134 is filled with the glass material. The simulation is performed assuming that the relative dielectric constant of the glass material is 5. Without any high-k layer, applied voltage gradients concentrate on a liquid crystal layer portion in a region near the electrode 121 on the lens peripheral portion, but almost no electric field is applied to a liquid crystal layer portion near the lens center. In the case shown in FIG. 7, since no voltage gradients can be provided for the liquid crystal layer, this arrangement cannot function as a convex lens.

FIG. 8 shows equipotential lines in a case in which voltages defined by V1(t)=V2(t) are applied, i.e., the voltage V1(t) is in phase with the voltage V2(t), and the arrangement includes the high-k layer 122. The simulation is performed assuming that the relative dielectric constant of the high-k layer 122 is 20. With the high-k layer 122, electric fields enter a portion near the lens center, and smooth voltage gradients extend from the lens center to the lens peripheral portion. In this case, the optical path difference gradually changes from the lens center to the lens peripheral portion, thereby obtaining good convex lens performance. It is possible to perform control to make equipotential lines largely enter in the lens center direction by increasing the relative dielectric constant of the high-k layer 122 and increasing the thickness of the high-k layer 122 or increasing one of them. This makes it possible to increase the region where voltage gradients can be obtained (i.e., the lens aperture).

FIG. 9 shows equipotential lines in a case in which voltages defined by $V1(t)=-V2(t)$ are applied, i.e., the voltage $V1(t)$ is in opposite phase with the voltage $V2(t)$, and the arrangement includes the high-k layer 122. At this time, electric fields are uniformly applied to the region from the lens center to the lens peripheral portion. In this state, this arrangement does not function as a lens, and the focal length is infinite.

The state shown in FIG. 8 corresponds to a case in which the in-phase rectangular-wave alternating voltages $V1(t)$ and $V2(t)$ having the same amplitude are applied. The state shown in FIG. 9 corresponds to a case in which the opposite-phase rectangular-wave alternating voltages $V1(t)$ and $V2(t)$ having the same amplitude are applied. It is possible to continuously change the effective voltages applied to the liquid crystal layers 114 and 134 by forming an intermediate state between the state in which the voltage $V1(t)$ is in phase with the voltage $V2(t)$ and the state in which the voltage $V1(t)$ is in opposite phase with the voltage $V2(t)$, i.e., by shifting the phases of the voltage $V1(t)$ and voltage $V2(t)$.

Figure 10:
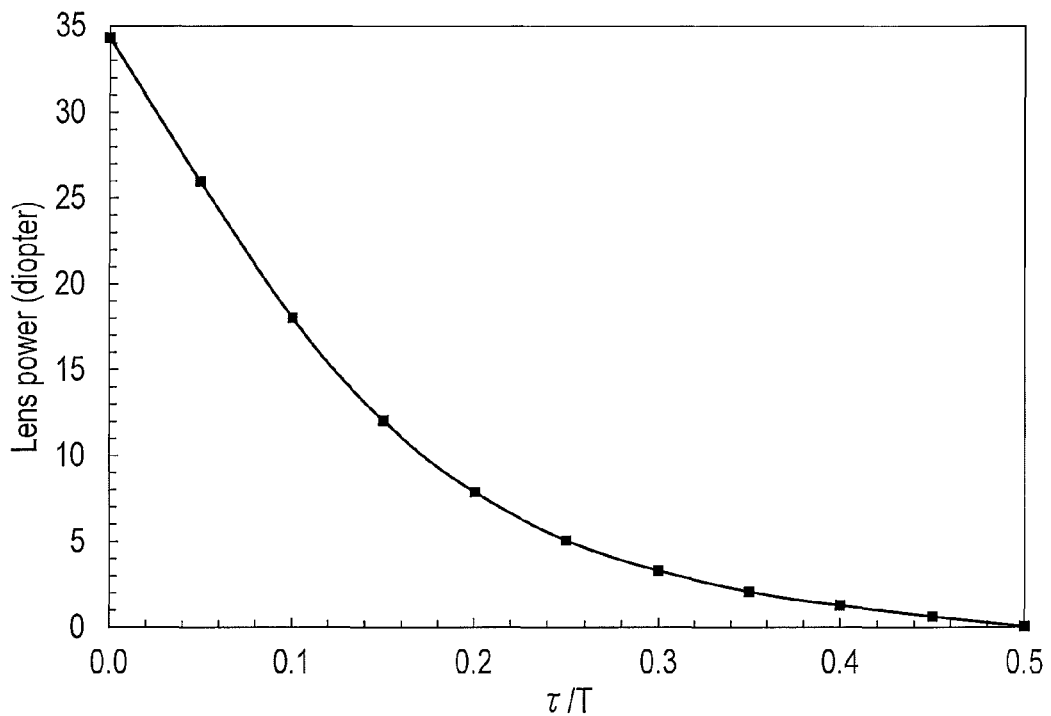
FIG. 10 is a graph showing the relationship between a phase shifting time τ and a focal length f.

FIG. 10 is a graph showing the relationship between a phase shifting time $\tau$ and a focal length f. Referring to FIG. 10, the abscissa represents a ratio "$\tau/T$" of the phase shifting time $\tau$ to a period T, and the ordinate represents a lens power (diopter). $V1=V2=15$ V.

As is obvious from FIG. 10, when $\tau/T$ is 0, i.e., the voltage $V1(t)$ is in phase with the voltage $V2(t)$, the lens power increases. That is, the arrangement functions as a convex lens whose focal length f is short. On the other hand, when $\tau/T$ is 0.5, i.e., the voltage $V1(t)$ is in opposite phase with the voltage $V2(t)$, the lens power is 0. That is, the focal length f is infinite. It is possible to change the focal length f of the liquid crystal lens 100 by controlling the phase shifting time $\tau$ between the voltages $V1(t)$ and $V2(t)$.

(Effects)

As described in detail above, in the first embodiment, the liquid crystal lens 100 includes the first liquid crystal cell 110, the second liquid crystal cell 130, and the intermediate layer 120 sandwiched between them. The first liquid crystal cell 110 includes the electrode 112 and the liquid crystal layer 114. The second liquid crystal cell 130 includes the electrode 132 and the liquid crystal layer 134. The intermediate layer 120 includes the electrode 121 having an opening portion and the high-k layer 122. The liquid crystal layer 114 has homogeneous alignment. The liquid crystal layer 134 has homogeneous alignment in a direction differing from the liquid crystal layer 114 by 90°. While the electrode 121 is grounded, the alternating voltage $V1(t)$ and the alternating voltage $V2(t)$ are respectively applied to the electrode 112 and the electrode 132. In addition, the phase difference between the alternating voltage $V1(t)$ and the alternating voltage $V2(t)$ is changed.

According to the first embodiment, therefore, it is possible to change the focal length of the liquid crystal lens 100 merely by the single driving method of shifting the phase between the alternating voltage $V1(t)$ and the alternating voltage $V2(t)$. Furthermore, including the two liquid crystal layers 114 and 134 having different aligning directions can form the liquid crystal lens 100 having the function of the convex lens, which is effective for polarized light in all directions.

In addition, it is possible to drive the liquid crystal lens 100 with a simple driving circuit because it controls the focal length by using two parameters, namely the amplitudes of the respective alternating voltages applied to the upper and lower electrodes 112 and 132 of the liquid crystal lens 100 and the phase difference between the voltages. This can further reduce the power consumption.

There is no need to provide any electrode pattern which has a complex shape as in a conventional liquid crystal lens and requires an accurate process. This makes it possible to reduce the manufacturing cost of the liquid crystal lens 100.

Furthermore, since there is no electrode pattern in a portion through which light passes, the liquid crystal lens is free from deterioration in imaging performance due to the light scattered by a pattern edge. This makes it possible to implement the liquid crystal lens 100 having excellent imaging performance.

[Second Embodiment]

According to the second embodiment, a liquid crystal lens 100 is formed by using two homeotropically aligned liquid crystal layers.

A liquid crystal layer 114 has homeotropic alignment such that the long axes of liquid crystal molecules are almost perpendicular to the in-plane direction. The homeotropically aligned liquid crystal layer 114 increases in refractive index in the same direction as that in which the dielectric constant decreases. That is, the dielectric constant anisotropy of the liquid crystal layer 114 is negative. For this reason, if the liquid crystal molecules are aligned to be almost perpendicular to the in-plane direction in an initial alignment state, i.e., in a no-voltage state, the liquid crystal molecules are tilted upon application of a voltage. The liquid crystal layer 114 is initially aligned to be slightly tilted from the vertical direction in the first direction (X direction) of the film surface so as to tilt the liquid crystal molecules in the same direction upon application of a voltage. That is, the liquid crystal molecules of the liquid crystal layer 114 uniformly have slight pre-tilt angles in the X direction. The pre-tilt angles are the tilt angles of the long axes of the liquid crystal molecules relative to the direction perpendicular to the film surface. Alignment films 113 and 116 and an alignment process step control the alignment of the liquid crystal layer 114.

A liquid crystal layer 134 has homeotropic alignment like the liquid crystal layer 114. In addition, the liquid crystal layer 134 is initially aligned to be slightly tilted from the vertical direction in the second direction (Y direction) perpendicular to the X direction of the film surface so as to tilt the liquid crystal molecules in the same direction upon application of a voltage. That is, the liquid crystal molecules of the liquid crystal layer 134 uniformly have slight pre-tilt angles in the Y direction. As described above, the directions in which the liquid crystal molecules of the liquid crystal layers 114 and 134 are tilted are perpendicular to each other when viewed from the lens optical axis.

The arrangement of the liquid crystal lens 100 is the same as that shown in FIGS. 1 and 2 in the first embodiment except that the liquid crystal layers 114 and 134 are initially aligned differently. In addition, the operation of a voltage control circuit 200 which applies voltages to the liquid crystal lens 100 is the same as that in the first embodiment.

Figure 11:
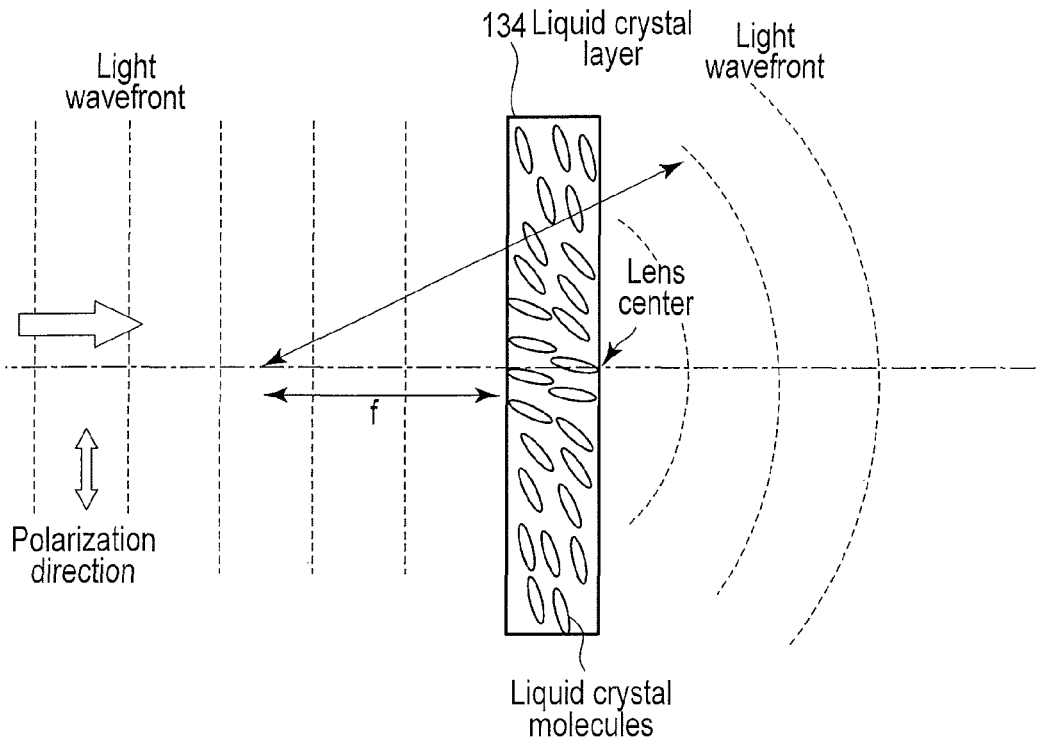
FIG. 11 is a sectional view for explaining the operation principle of a liquid crystal lens 100 according to the second embodiment.

FIG. 11 is a sectional view for explaining the operation principle of the liquid crystal lens 100 according to the second embodiment. FIG. 11 shows the liquid crystal layer 134 functioning as a lens in an extracted state. The operation of the liquid crystal layer 114 is the same as that of the liquid crystal layer 134 in FIG. 11 except that the aligning directions differ from each other by 90°.

When voltage gradients like those shown in FIG. 8 are applied to the liquid crystal layer 134 by using the voltage control circuit 200, the liquid crystal molecules of the liquid crystal layer 134 are aligned in a direction almost perpendicular to the in-plane direction at the lens central portion and are gradually tilted in the in-plane direction toward the lens peripheral portion. Using the homeotropically aligned liquid crystal layer 134 makes the optical path difference at the lens central portion become smaller than that at the lens peripheral portion, as shown in FIG. 11. This makes the liquid crystal layer 134 function as a concave lens. That is, this can implement the liquid crystal lens 100 having a negative lens power.

As described in detail above, according to the second embodiment, it is possible to form the liquid crystal lens 100 having the function of a concave lens having a variable focal length. Other effects are the same as those of the first embodiment.

[Third Embodiment]

According to the third embodiment, a liquid crystal lens 100 is formed by using two bend-aligned liquid crystal layers.

Figure 12:
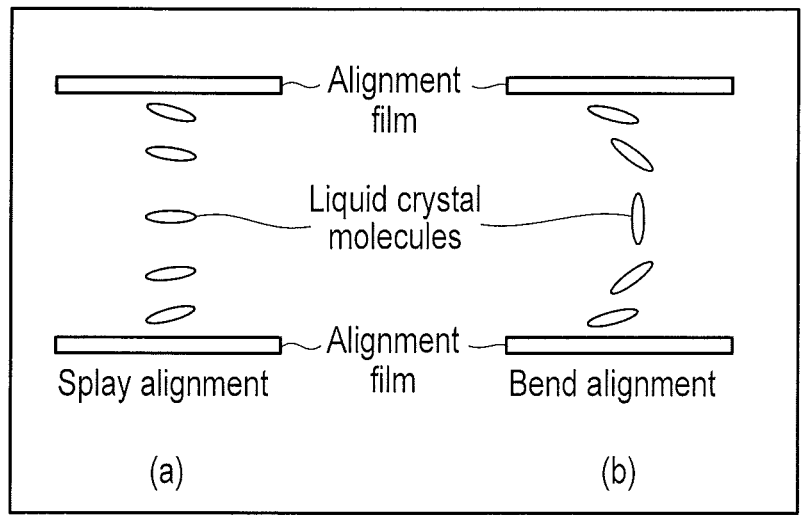
FIG. 12 is a view for explaining splay alignment and bend alignment.

A liquid crystal layer 114 has splay alignment in an initial alignment state, i.e., in a no-voltage state, but transfers to bend alignment upon application of a voltage. In FIG. 12, (a) is a view for explaining the splay alignment, and (b) is a view for explaining bend alignment. When liquid crystal molecules are splay-aligned, they are aligned in a splay pattern so as to have slight tilt angles relative to the in-plane direction. When liquid crystal molecules are bend-aligned, they are aligned in an arc pattern. The liquid crystal layer 114 has splay alignment such that the long axes of liquid crystal molecules are aligned in the first direction (X direction) of the film surface. Alignment films 113 and 116 and an alignment process control the alignment of the liquid crystal layer 114.

A liquid crystal layer 134 has splay alignment in a no-voltage state like the liquid crystal layer 114, but transfers to bend alignment upon application of a voltage. In addition, the liquid crystal layer 134 is splay-aligned such that the long axes of liquid crystal molecules are aligned in the second direction (Y direction) perpendicular to the X direction of the film surface. As described above, the aligning directions of the liquid crystal molecules of the liquid crystal layers 114 and 134 are perpendicular to each other when viewed from the lens optical axis.

The arrangement of the liquid crystal lens 100 is the same as that shown in FIGS. 1 and 2 in the first embodiment except that the liquid crystal layers 114 and 134 are initially aligned differently. In addition, the operation of a voltage control circuit 200 which applies a voltage to the liquid crystal lens 100 is the same as that in the first embodiment.

Figure 13:
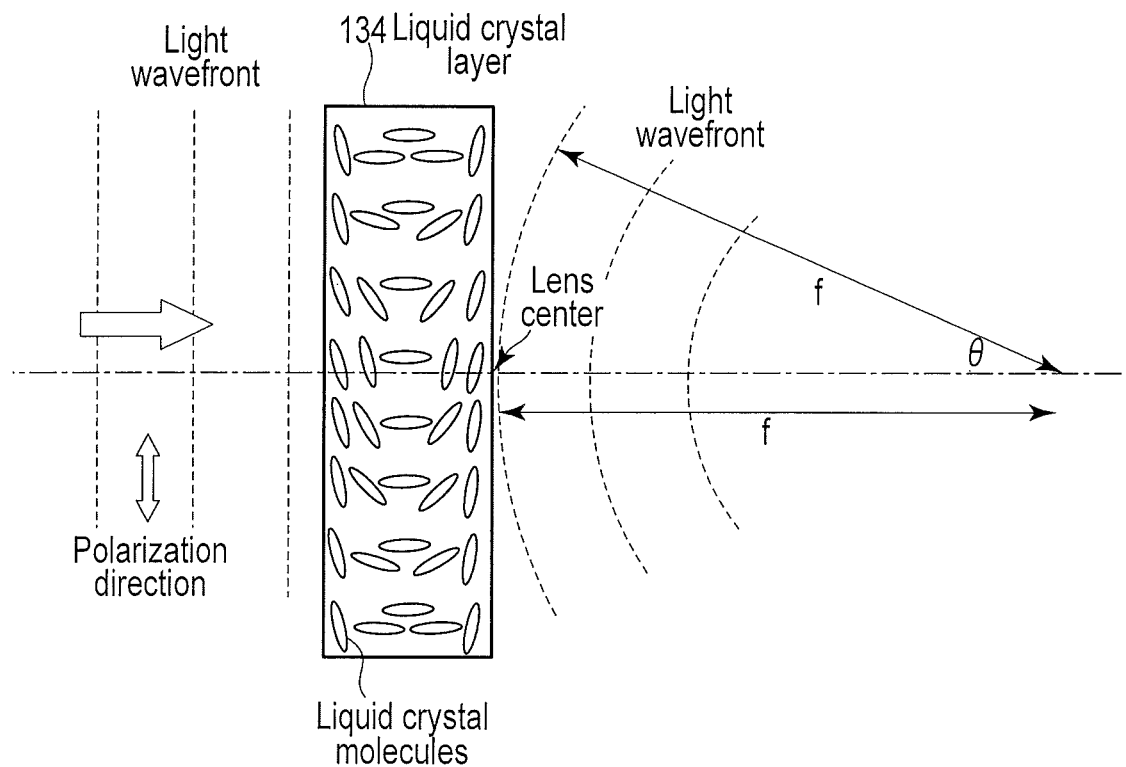
FIG. 13 is a sectional view for explaining the operation principle of a liquid crystal lens 100 according to the third embodiment.

FIG. 13 is a sectional view for explaining the operation principle of the liquid crystal lens 100 according to the third embodiment. FIG. 13 shows the liquid crystal layer 134 functioning as a lens in an extracted state. The operation of the liquid crystal layer 114 is the same as that of the liquid crystal layer 134 in FIG. 13 except that the aligning directions differ from each other by 90°.

When voltage gradients like those shown in FIG. 8 are applied to the liquid crystal layer 134 by using the voltage control circuit 200, the liquid crystal layer 134 transfers from the splay alignment to the bend alignment, and the liquid crystal molecules tilt largely in the direction perpendicular to the film surface from the lens central portion to the lens peripheral portion. As a result, as the alignment distribution of the liquid crystal layer 134 changes, the refractive index distribution changes from the lens center to the lens peripheral portion. This allows the liquid crystal layer 134 to function as a lens. It is possible to freely change the refractive index distribution on the liquid crystal layer 134 by controlling the manner of applying voltages to the electrodes 112, 121, and 132. This makes it possible to control the optical characteristics of the convex lens.

As described in detail above, according to the third embodiment, it is possible to form the liquid crystal lens 100 having the function of a concave lens having a variable focal length. The bend alignment mode exhibits smaller changes in optical path difference due to voltage changes than the homogeneous alignment mode with the same cell gap, and hence a characteristic feature of having a high response speed although having a small lens power. Other effects are the same as those in the first embodiment.

Note that the liquid crystal lens 100 described in each embodiment can be applied to various types of optical apparatuses and electronic devices which use lenses. For example, the liquid crystal lens can be applied to compact electronic devices such as a camera module, camera, camera-equipped compact electronic device (cellular phone, portal information terminal, and the like), optical pickup, reader for reading barcodes, QR (Quick Response) codes, and the like, and scanner.

[Fourth Embodiment]

The fourth embodiment will exemplify a technique for restricting the blurring of a liquid crystal lens 100 of the present invention and a manufacturing method for implementing a structure suitable for the liquid crystal lens 100 of the present invention.

Figure 14:
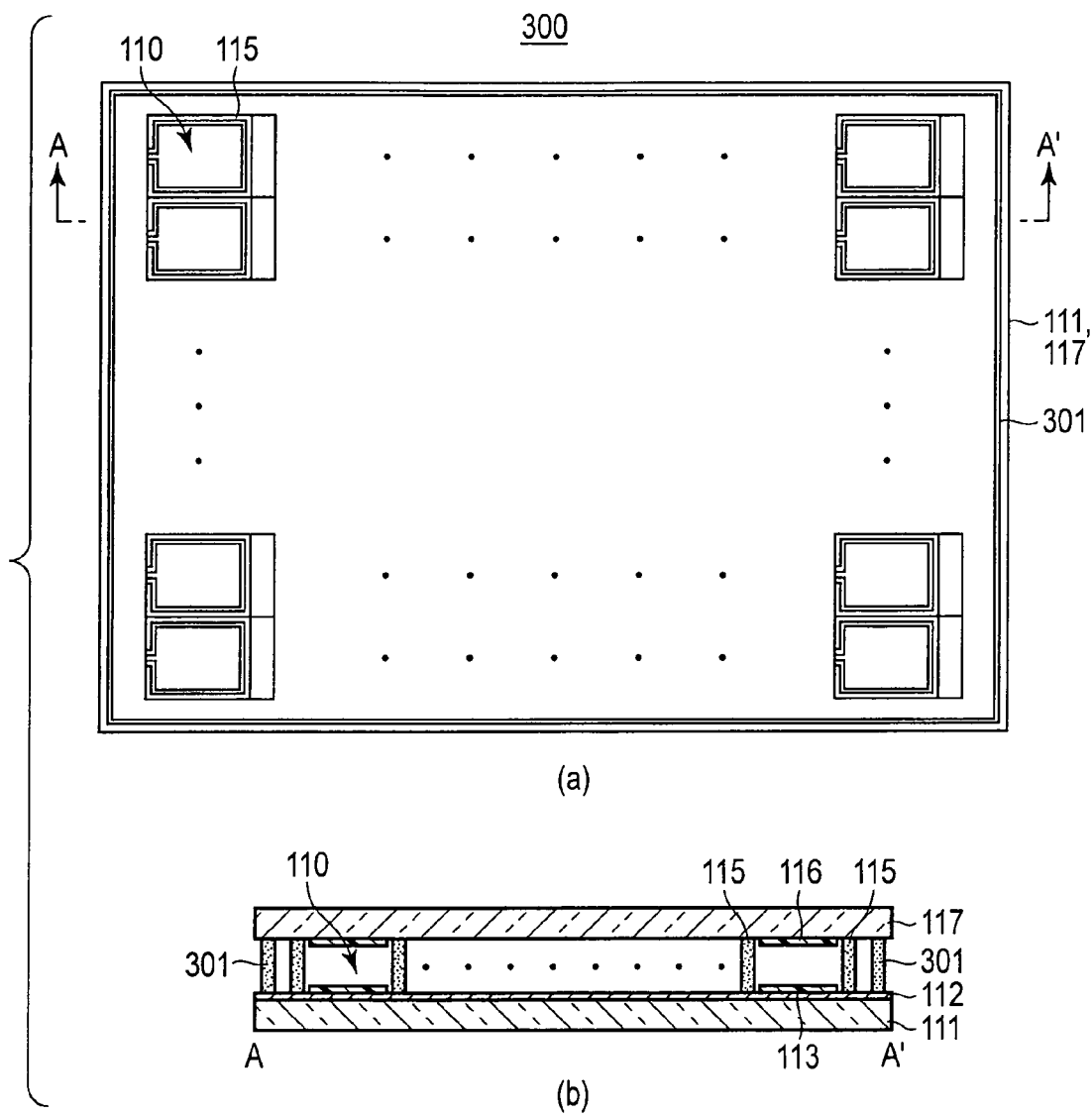
FIG. 14 shows a step of manufacturing a liquid crystal lens according to the fourth embodiment.

In FIG. 14, (a) is a plan view showing a step of manufacturing the liquid crystal lens 100, and (b) is a sectional view taken along a line A-A' in (a) in FIG. 14. Note that the plan view shown in (a) in FIG. 14 schematically shows a liquid crystal cell 110 to be diced in the subsequent step.

As shown in FIG. 14, two mother glasses 111 and 117 are bonded to each other to form a unit 300. One mother glass 111 includes a transparent electrode 112. The other mother glass 117 is blank glass having no transparent electrode. Since the unit 300 is manufactured in the existing general process of manufacturing a liquid crystal panel, each mother glass has a thickness of about 0.5 mm to 1.1 mm. Alignment films 113 and 116 are respectively formed on the mother glasses 111 and 117. Rubbing treatments are performed on the alignment films 113 and 116.

Seal members 115 and 301 are printed on the mother glass 111 (or the mother glass 117), and the two mother glasses 111 and 117 are then bonded to each other to form the unit 300. The seal member 115 includes a spacer having a desired size to control the thickness of the liquid crystal layer. The seal member 115 has, for example, a rectangular outer shape. The position 301 is formed along an end portion of mother glass 111.

Figure 15:
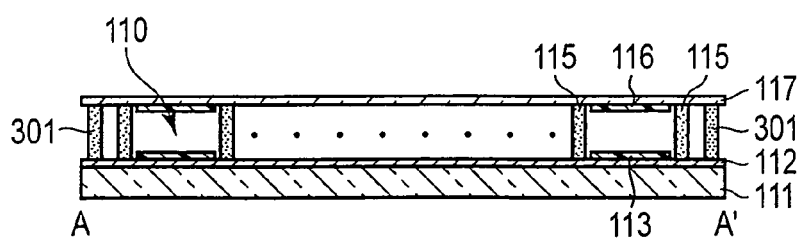
FIG. 15 is a view showing a step of manufacturing the liquid crystal lens following the step in FIG. 14.

Subsequently, as shown in FIG. 15, the unit 300 is processed into a low-profile unit (thin unit) by thinning the mother glass 117 on the bland glass side. The process of thinning the glass includes a mechanical polishing method of mechanically abrading off the glass surface by using an abrasive or a chemical polishing method of abrading off the glass surface by a chemical reaction. This embodiment may use either the mechanical polishing method or the chemical polishing method. Film thickness conditions for the glass substrate 117 (and a glass substrate 137) to be thinned film will be described later.

Figure 16:
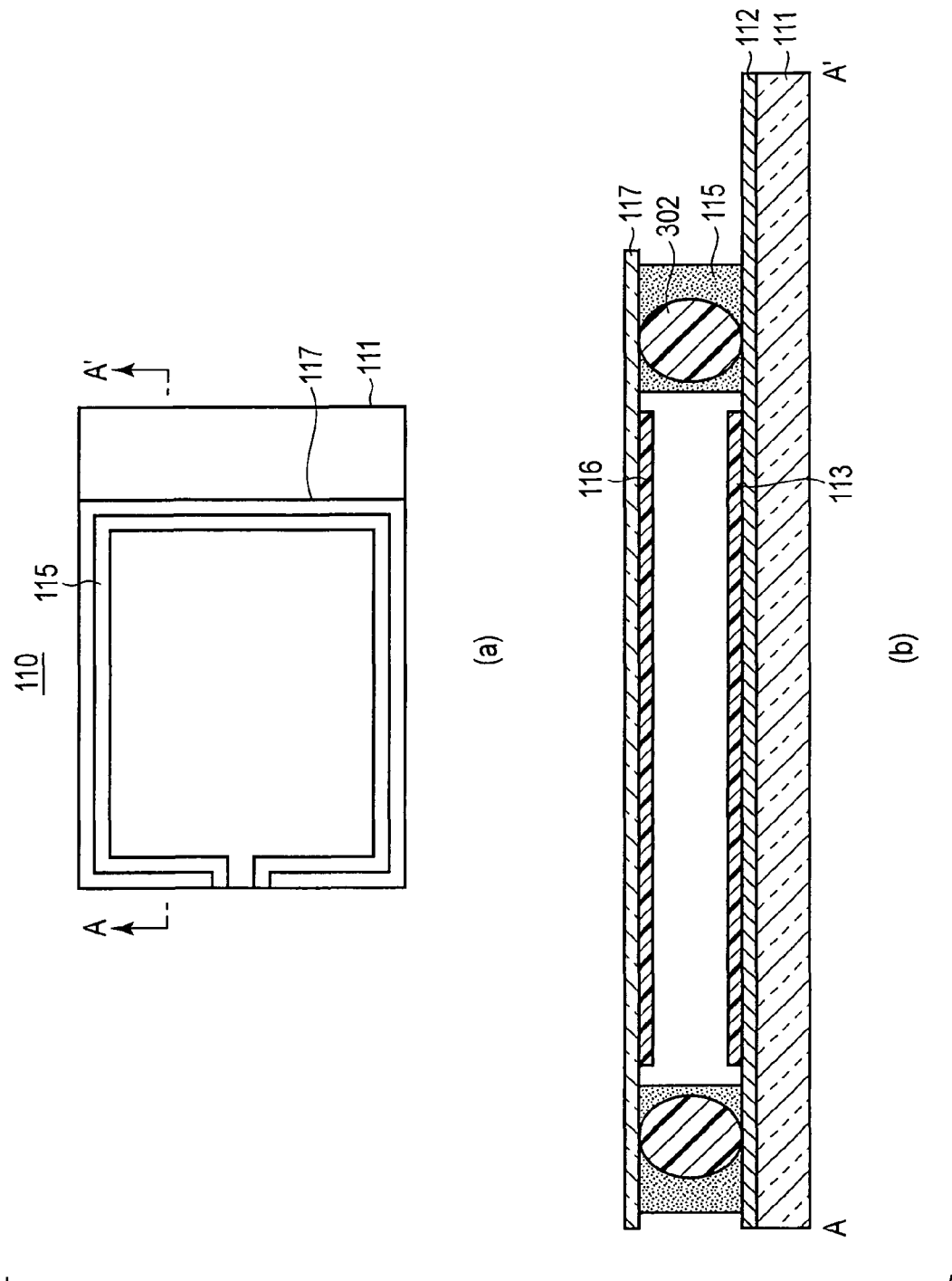
FIG. 16 shows a step of manufacturing the liquid crystal lens following the step in FIG. 15.

Subsequently, scribing and braking steps are performed to cut the unit 300 into the discrete liquid crystal cell 110. More specifically, a scribing process is performed to form scribe lines on the unit 300 by laser scribing or the like, and a braking process is performed to divide the unit 300 by applying pressure on the scribe lines. In FIG. 16, (a) is a plane view of the diced liquid crystal cell 110, and (b) is a sectional view taken along a line A-A' in (a) in FIG. 16. The liquid crystal cell 110 has a rectangular shape larger in the horizontal direction than in the vertical direction. Likewise, the seal member 115 has a rectangular outer shape.

To extract outward the transparent electrode 113 inside the cell, the size of the thinned glass substrate 117 is set to be smaller than that of the glass substrate 111 on the transparent electrode 113 side. Referring to FIG. 16, the size of the thinned glass substrate 117 is decreased in the horizontal direction in FIG. 16 to expose a portion of the glass substrate 111 (and the transparent electrode 112) when viewed in a plan view. Note that FIG. 16 shows a spacer 302 for controlling the thickness of the liquid crystal layer. The spacer 302 is formed from, for example, a plastic or glass material.

In the scribing and braking steps, since pressure acts on the unit 300, the liquid crystal cell 110 (especially the glass substrate) may distort. In this case, if the seal member 115 is rectangular, the liquid crystal cell 110 also distorts in a shape corresponding to a rectangular shape. This is not preferable when forming a circular lens. As a countermeasure against this, the seal member 115 is formed into a ring-like (circular) shape like the lens, as indicated by (a) in FIG. 17. This make the circular region surrounded by the seal member 115 of the liquid crystal cell 110 distort in a shape corresponding to a circular shape. This makes it possible to restrict a deterioration in lens characteristics even through the scribing and braking steps.

Figure 17:
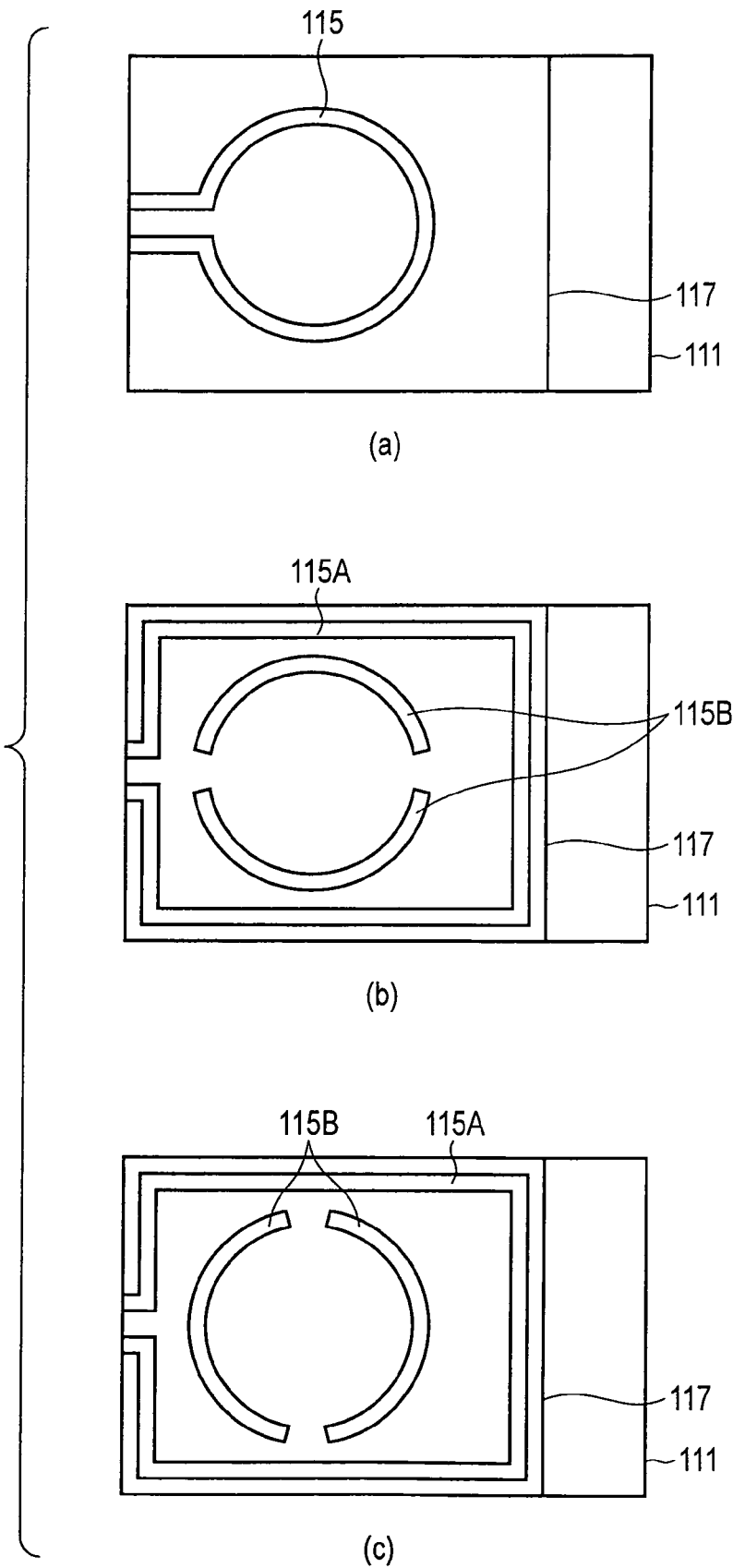
FIG. 17 shows an example of a seal member.

As indicated by (b) and (c) in FIG. 17, a seal member 115B having a partially notched ring-like shape may be formed inside a rectangular seal member 115A for sealing a liquid crystal. In other words, the seal member 115B is constituted by two arcuated members. This arrangement can hold the strength of the liquid crystal cell 110 with the rectangular seal member 115A in addition to the effect indicated by (a) in FIG. 17.

Note that a notched portion of the seal member 115B serves as a liquid crystal injection port. The example shown in FIG. 17 is also applied to the seal member 135.

Figure 18:
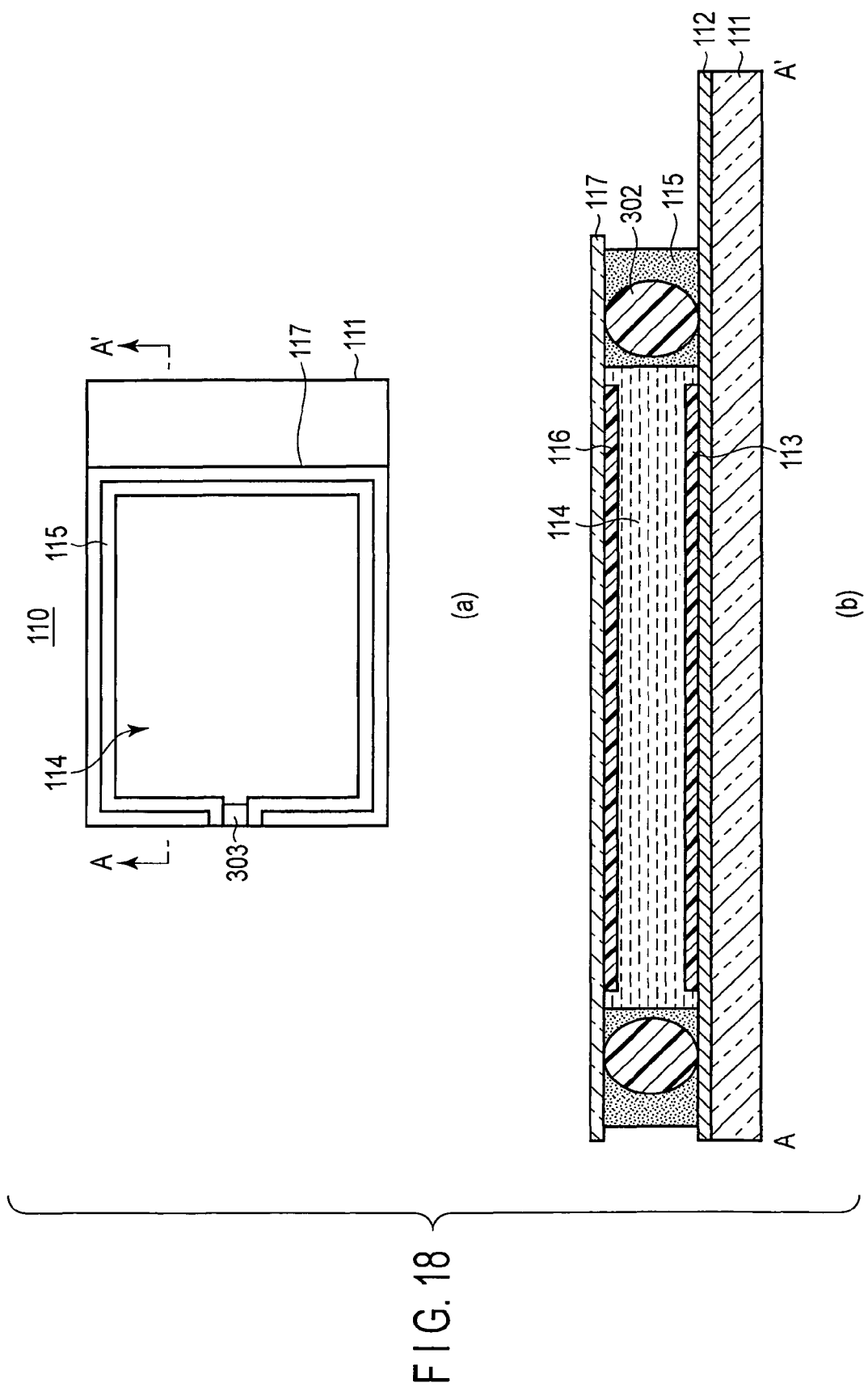
FIG. 18 shows a step of manufacturing the liquid crystal lens following the step in FIG. 16.

Subsequently, as shown in FIG. 18, a liquid crystal is injected into the liquid crystal cell 110. The opening portion of the seal member 115 is then sealed with a seal member 303. Note that the seal member 303 preferably does not protrude outside because the two liquid crystal cells are bonded to each other in the subsequent step. With the above manufacturing steps, the liquid crystal cell 110 is complete. As the liquid crystal cell 130, a cell identical to the diced liquid crystal cell 110 is used.

Figure 19:
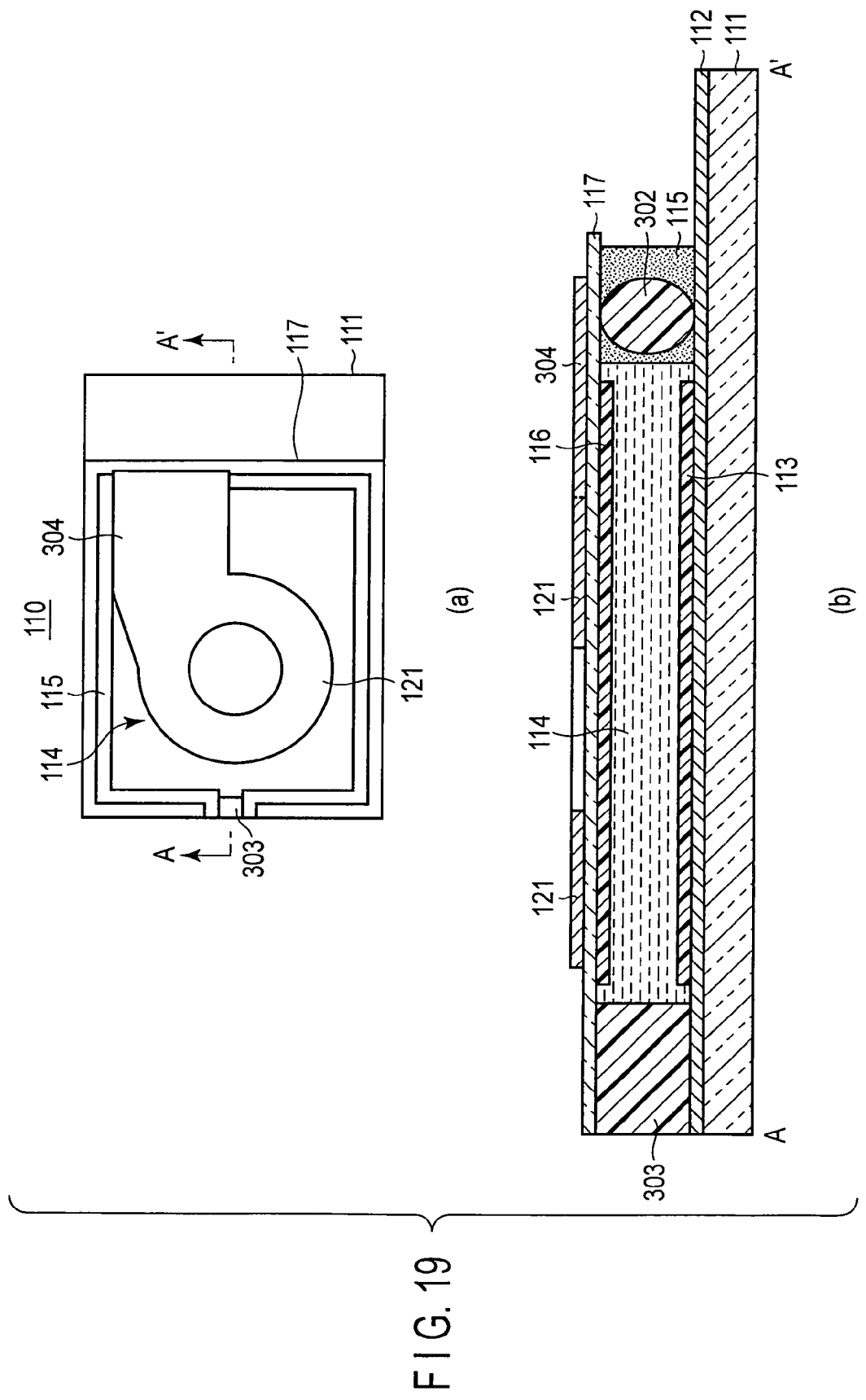
FIG. 19 shows a step of manufacturing the liquid crystal lens following the step in FIG. 18.

Subsequently, as shown in FIG. 19, a ring-like electrode 121 is formed on the glass substrate 117. At this time, a connecting terminal (extraction electrode) 304 is extracted from the ring-like electrode 121. In this embodiment, the connecting terminal 304 is extracted to the side where an electrode 132 is exposed. A black carbon-based conductive paste is used for the ring-like electrode 121 to reduce the reflection of light by the ring electrode when it operates as a lens. The conductive paste is printed on the upper surface of the glass substrate 117 by screen printing to form the ring-like electrode 121. The ring-like electrode 121 preferably has a thickness of about 5 μm to 10 μm to fully fill a stepped portion when a high dielectric constant film sheet is bonded in the next step. In a demonstration experiment in this embodiment, a ring-like electrode was formed by using "SS Rio phase" available from TOYO INK.

In FIG. 20, (a) is a plan view of a diced liquid crystal cell 130, and (b) is a sectional view taken along a line A-A' in (a) in FIG. 20. As shown in FIG. 20, a high-k layer 122 having a larger size than the ring electrode is formed on the transparent substrate 137 of the liquid crystal cell 130. The high-k layer 122 is formed by bonding a sheet-like high dielectric constant film having a thickness of about 30 μm on the glass substrate 137. This high dielectric constant film sheet is a sheet obtained by dispersing fine particles of a ferroelectric material containing barium titanate as a main component in a resin binder. This resin binder has a thermosoftening property and causes a curing reaction upon irradiation with UV. In the step in FIG. 20, the high dielectric constant film sheet is softened by heating and is bonded to the surface of the liquid crystal cell 130. This sheet is cured by UV in the next step.

Figure 21:
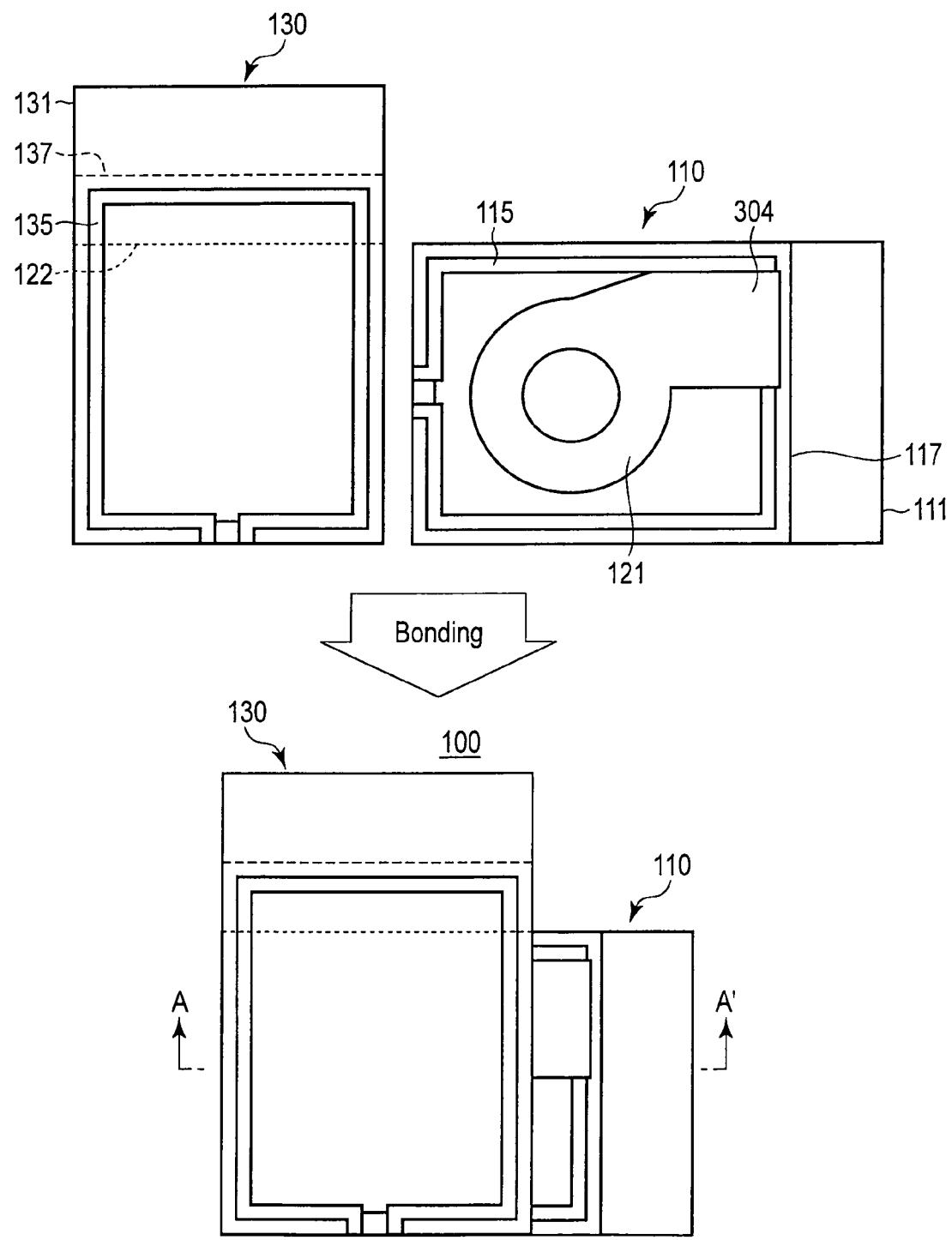
FIG. 21 is a plan view showing a step of manufacturing the liquid crystal lens following the step in FIG. 20.
Figure 22:
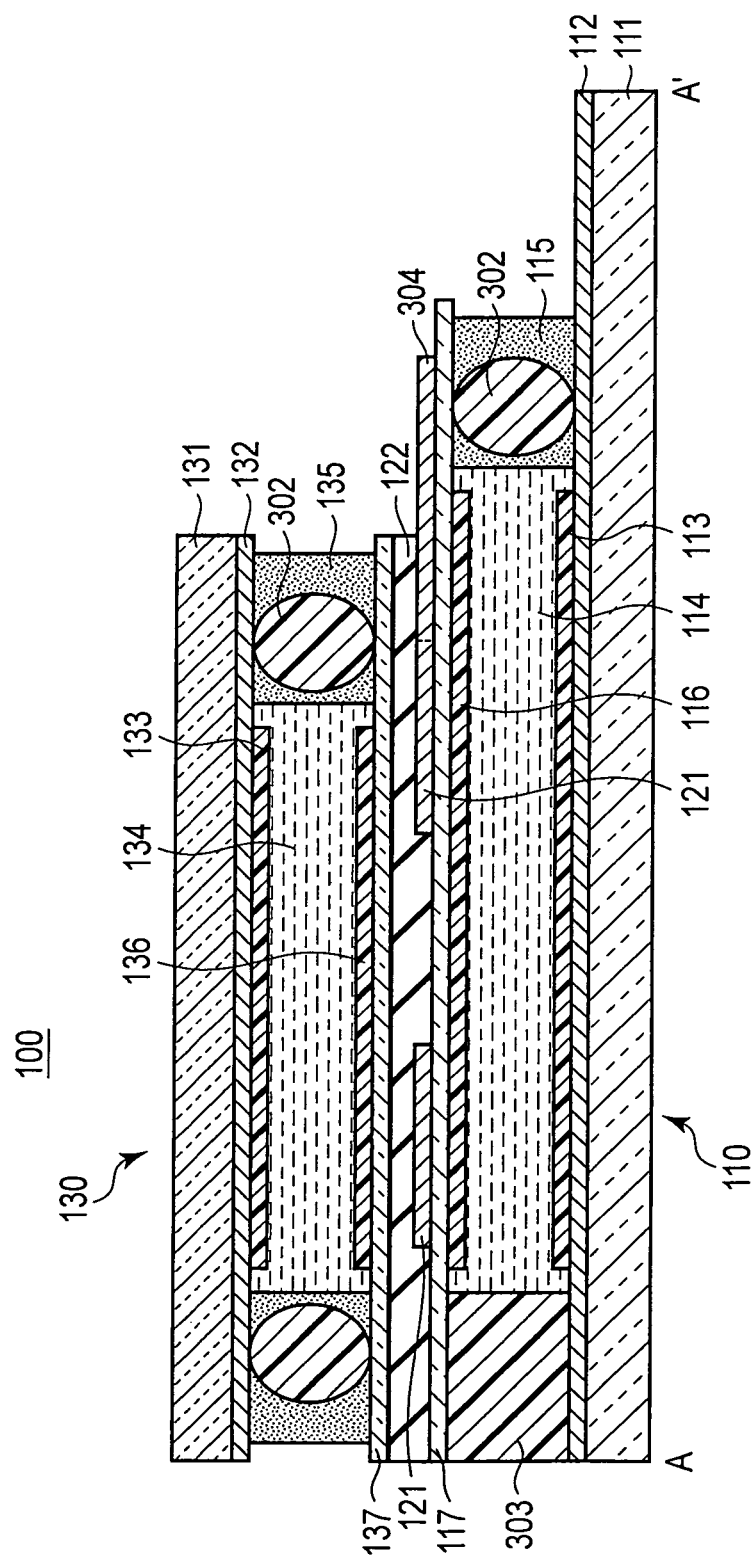
FIG. 22 is a sectional view taken along a line A-A' in FIG. 21 and showing a step of manufacturing the liquid crystal lens.

As shown in FIGS. 21 and 22, the liquid crystal cell 110 on which the ring-like electrode 121 is formed is bonded to the liquid crystal cell 130 on which the high-k layer 122 is formed. More specifically, the liquid crystal cell 110 is made to face the liquid crystal cell 130 such that the aligning direction of a liquid crystal layer 114 differs from that of a liquid crystal layer 134 by 90°. Thereafter, the ring-like electrode 121 is brought into contact with the high-k layer 122. The two liquid crystal cells are pressurized while the high-k layer 122 is softened by heating. At this time, since the high-k layer 122 is softened, the stepped portion of the opening portion of the electrode 121 can be filled up. Note that this bonding step is preferably performed in a vacuum because air bubbles may enter between the two liquid crystal cells. After the two liquid crystal cells are bonded by pressure, the overall bonded liquid crystal cells are irradiated with UV to cure the high-k layer 122, thereby bonding the two liquid crystal cells. In this manner, the liquid crystal lens 100 according to the fourth embodiment is manufactured.

Figure 23:
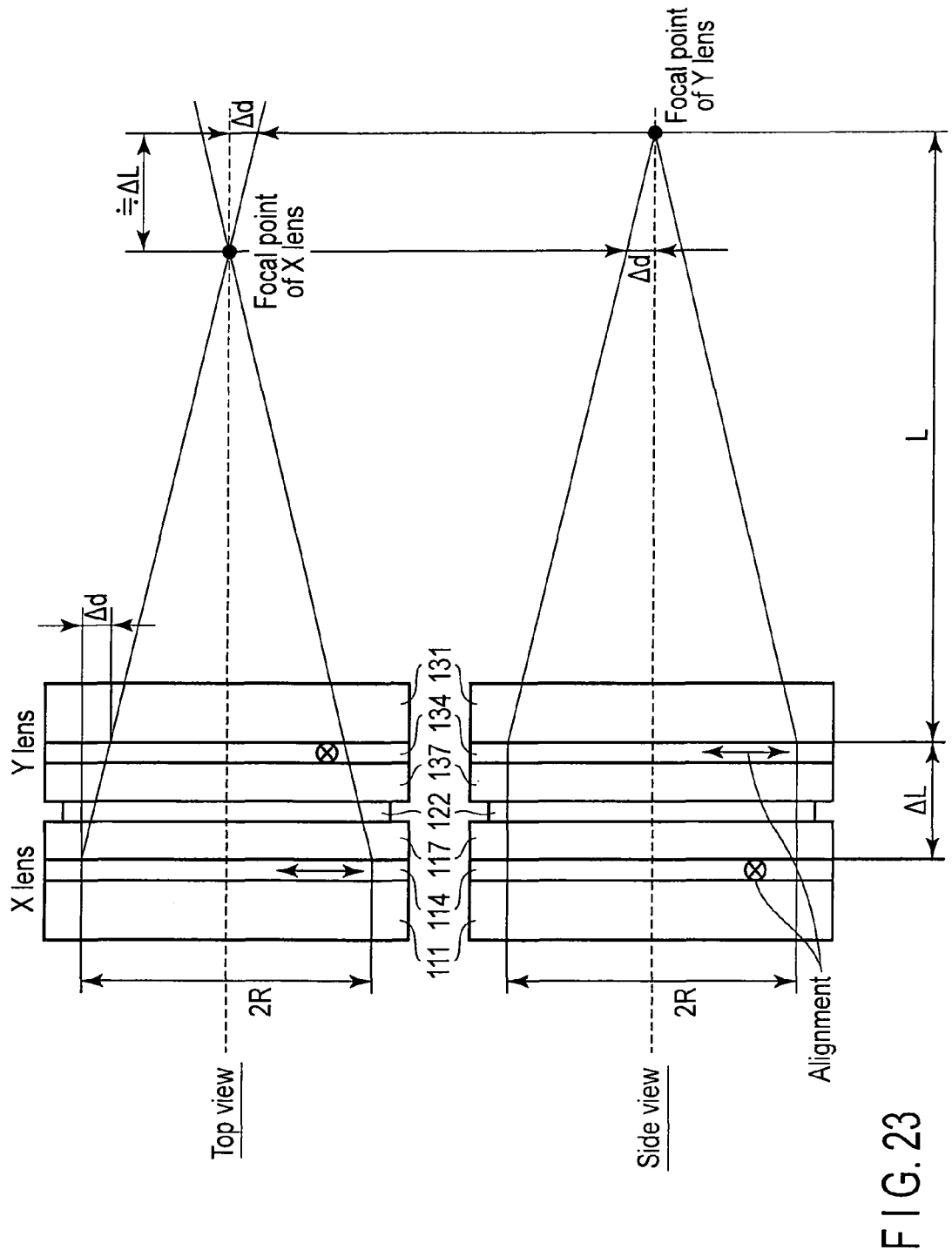
FIG. 23 is a schematic view for explaining the defocusing of the liquid crystal lens.
Figure 24:
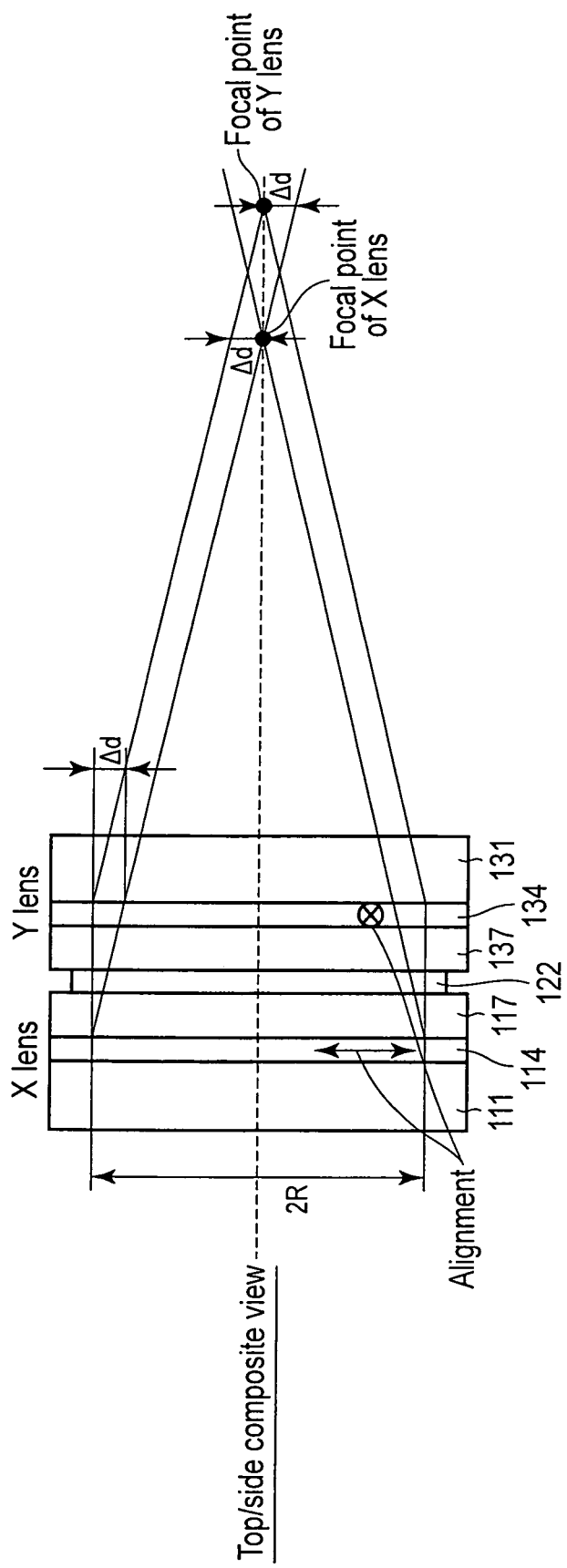
FIG. 24 is a schematic view obtained by combining the top view and side view shown in FIG. 23.
Figure 25:
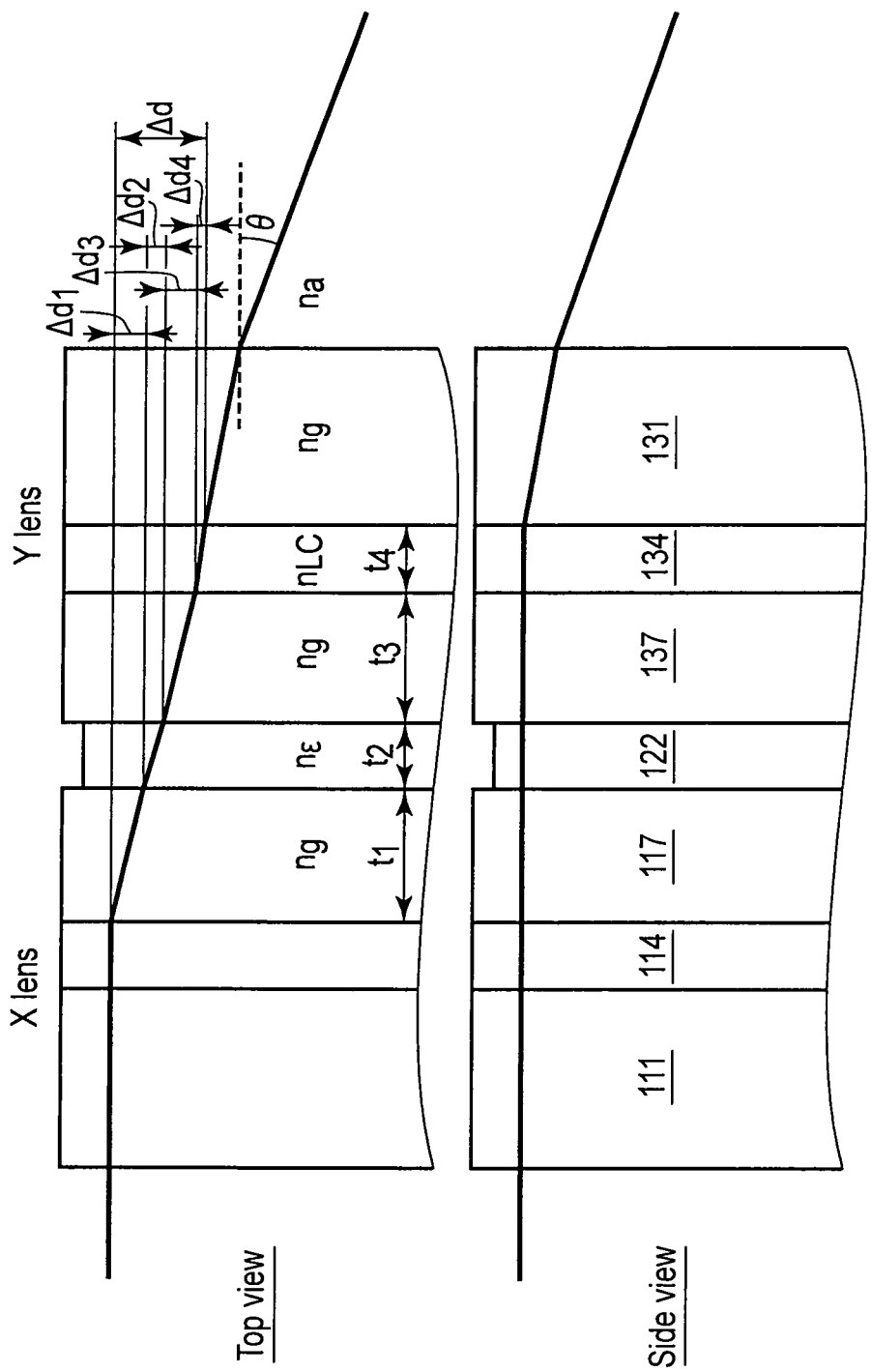
FIG. 25 is a schematic view for explaining the aberration between an X lens and a Y lens.

Film thickness conditions for the glass substrate 117 (and the glass substrate 137) to be thinned will be described next. FIG. 23 is a schematic view for explaining the defocusing of the liquid crystal lens 100. FIG. 23 shows a top view and side view of the liquid crystal lens 100. FIG. 24 is a schematic view obtained by combining the top view and side view shown in FIG. 23. FIG. 25 is a schematic view for explaining the aberration between the X lens and the Y lens. The X lens corresponds to the liquid crystal cell 110. The Y lens corresponds to the liquid crystal cell 130.

Referring to FIG. 23, let L be a focal length, 2R be a lens aperture, and ΔL be the distance between the light exit surfaces (light output surfaces) of the X and Y lenses. In this embodiment, a light exit surface (light output surface) is a reference surface from which the light refracted by a liquid crystal cell exits. At this time, the focal point of the X lens shifts from that of the Y lens in the optical axis direction by almost ΔL (≈ΔL). That is, the aberration (focal point shift amount) between the X lens and the Y lens in the optical axis direction is "≈ΔL". In the embodiment, the focal point shift amount between the X lens and the Y lens in a direction (lens aperture direction) perpendicular to the optical axis will be referred to as a transverse aberration Δd.

Referring to FIG. 25, let θ be the refraction angle of light exiting from the liquid crystal lens 100, $n_a$ be the refractive index of air, $n_g$ and $θ_g$ be the refractive index and refraction angle of each glass substrate (the glass substrates 111, 117, 131, and 137), $n_{LC}$ and $θ_{LC}$ be the refractive index and refraction angle of a liquid crystal (the liquid crystal layers 114 and 134), $n_∈$ and $θ_∈$ be the refractive index and refraction angle of a dielectric body (the high-k layer 122), $t_1$ be the thickness of the glass substrate 117, $t_2$ be the thickness of the high-k layer 122, $t_3$ be the thickness of the glass substrate 137, and $t_4$ be the thickness of the liquid crystal layer 134. Therefore, the distance between the light output surfaces of the X and Y lenses is expressed by "$\Delta L = t_1 + t_2 + t_3 + t_4$". Let $\Delta d_1$ be the distance that light passing through the glass substrate 117 propagates in the lens aperture direction, $\Delta d_2$ be the distance that light passing through the high-k layer 122 propagates in the lens aperture direction, $\Delta d_3$ be the distance that light passing through the glass substrate 137 propagates in the lens aperture direction, and $\Delta d_4$ be the distance that light passing through the liquid crystal layer 134 propagates in the lens aperture direction.

According to Snell's law, "$\alpha = n_a \cdot \sin\theta = n_g \cdot \sin\theta_g = n_L \cdot \sin\theta_{LC} = n_\in \cdot \sin\theta_\in$" holds, where $\alpha$ is a constant. The distances $\Delta d_1$ to $\Delta d_4$ shown in FIG. 25 are expressed by mathematical expressions (5) to (8). Mathematical expression (9) represents $\sin\theta$.

$$\Delta d_1 = t_1 \sqrt{\frac{\alpha^2}{n_g^2 - \alpha^2}} \quad (5)$$

$$\Delta d_2 = t_2 \sqrt{\frac{\alpha^2}{n_\in^2 - \alpha^2}} \quad (6)$$

$$\Delta d_3 = t_3 \sqrt{\frac{\alpha^2}{n_g^2 - \alpha^2}} \quad (7)$$

$$\Delta d_4 = t_4 \sqrt{\frac{\alpha^2}{n_{LC}^2 - \alpha^2}} \quad (8)$$

$$\sin\theta = \frac{R}{\sqrt{L^2 + R^2}} = \sqrt{\frac{R^2}{L^2 + R^2}} \quad (9)$$

For example, $\Delta d_4$ is calculated as indicated by mathematical expression (10).

$$\Delta d_4 = \quad (10)$$

$$t_4 \cdot \tan\theta_{LC} = t_4 \sqrt{\frac{\sin^2\theta_{LC}}{1 - \sin^2\theta_{LC}}} = t_4 \sqrt{\frac{\left[\frac{\alpha}{n_{LC}}\right]^2}{1 - \left[\frac{\alpha}{n_{LC}}\right]^2}} = t_4 \sqrt{\frac{\alpha^2}{n_{LC}^2 - \alpha^2}}$$

$\Delta d_1$ to $\Delta d_3$ are calculated in the same manner as for $\Delta d_4$.

The transverse aberration $\Delta d$ is the sum of $\Delta d_1$ to $\Delta d_4$, and hence depends on the refractive index of each layer. The refractive indices $n_g$, $n_\in$, and $n_{LC}$ are generally larger than the refractive index $n_a$ of air, and hence "$n_g \to n_a$, $n_\in \to n_a$, and $n_{LC} \to n_a$, and $\Delta d \to$ large". Therefore, the transverse aberration $\Delta d$ is maximized when "$n_g = n_a$, $n_\in = n_a$, and $n_{LC} = n_a$". Under these conditions, the transverse aberration $\Delta d$ is expressed by mathematical expression (11).

$$\Delta d = \Delta d_1 + \Delta d_2 + \Delta d_3 + \Delta d_4 \quad (11)$$

$$= t_1 \sqrt{\frac{\alpha^2}{n_a^2 - \alpha^2}} + t_2 \sqrt{\frac{\alpha^2}{n_a^2 - \alpha^2}} + t_3 \sqrt{\frac{\alpha^2}{n_a^2 - \alpha^2}} + t_4 \sqrt{\frac{\alpha^2}{n_a^2 - \alpha^2}}$$

$$= (t_1 + t_2 + t_3 + t_4) \sqrt{\frac{\alpha^2}{n_a^2 - \alpha^2}} = \Delta L \sqrt{\frac{\sin^2\theta}{1 - \sin^2\theta}}$$

$$= \Delta L \sqrt{\frac{\left[\frac{R^2}{L^2 + R^2}\right]}{\left[1 - \frac{R^2}{L^2 + R^2}\right]}}$$

This embodiment assumes a liquid crystal lens whose lens aperture 2R is about 2 mm and focal length L≥100 nm. Under these conditions, the transverse aberration $\Delta d$ is expressed by mathematical expression (12).

$$\Delta d = \Delta L \sqrt{\frac{\left[\frac{1^2}{100^2 + 1^2}\right]}{\left[1 - \frac{1^2}{100^2 + 1^2}\right]}} = 10^{-2} \cdot \Delta L \quad (12)$$

In a CCD (Charge Coupled Device) image sensor or CMOS (Complementary Metal Oxide Semiconductor) image sensor having about 1,000,000 pixels as imaging elements, the imaging element pitch (pixel pitch) is about 5 μm. In order to reduce the blurring of the liquid crystal lens 100, $\Delta d$ needs to fall within 5 μm. Therefore, "$\Delta d = 10^{-2} \cdot \Delta L \leq 5$ μm" holds, and "$\Delta L \leq 500$ μm" is calculated.

According to the above description, the interface between the liquid crystal layer and the glass substrate is used as the reference surface (the light exit surface from which light passing through one liquid crystal cell exits) which refracts light entering one liquid crystal cell. However, the above description holds even when the central surface of the liquid crystal layer in the lens aperture direction is used as a reference.

In order to satisfy "$\Delta L \leq 500$ μm", if the high-k layer 122 has a thickness of 100 μm or less and the liquid crystal layers 114 and 134 each have a thickness of 100 μm or less, the glass substrates 117 and 137 to be thinned each are preferably processed to have a thickness of 150 μm or less.

Although the above description has exemplified the case in which the number of imaging elements is about 1,000,000 (pixels), it is necessary to set $\Delta d$ within 5 μm even in a case in which the number of imaging elements is 1,000,000 (pixels) or more. Therefore, "$\Delta L \leq 500$ μm" holds even in the case in which the number of imaging elements is 1,000,000 (pixels) or more.

(Effect)

As described in detail above, the fourth embodiment is configured to adjust the distance between the liquid crystal layer 114 and the liquid crystal layer 134 by thinning each of the transparent substrates 117 and 137 to a predetermined thickness. This reduces the transverse aberration between the X lens (liquid crystal cell 110) and the Y lens (liquid crystal cell 130). More specifically, the transverse aberration between the X and Y lenses is set to be equal to or less than the pixel pitch of the liquid crystal display apparatus incorporating the liquid crystal lens 100.

According to the fourth embodiment, it is possible to reduce the blurring of the liquid crystal lens 100. In addition, having the structure exemplified in the fourth embodiment can implement the liquid crystal lens 100 having desired performance and desired strength.

In addition, as the connecting terminals to be electrically connected to the transparent electrodes 112 and 132 and the ring-like electrode 121 are exposed, it is possible to electrically connect the terminals to the lens unit incorporated in the liquid crystal lens 100.

Furthermore, it is possible to manufacture the two liquid crystal cells 110 and 130 by using one unit including two pieces of mother glass. This makes it possible to reduce the manufacturing cost of the liquid crystal lens 100.

[Fifth Embodiment]

A liquid crystal lens is finally incorporated in various types of lens units, and is connected to each lens unit via connecting terminals. If, therefore, the connecting terminals of the liquid crystal lens have a complex arrangement, it is difficult to incorporate the liquid crystal lens in the lens unit. The fifth embodiment is therefore configured to implement a liquid crystal lens including connecting terminals that allow easy connection to the lens unit.

Figure 26:
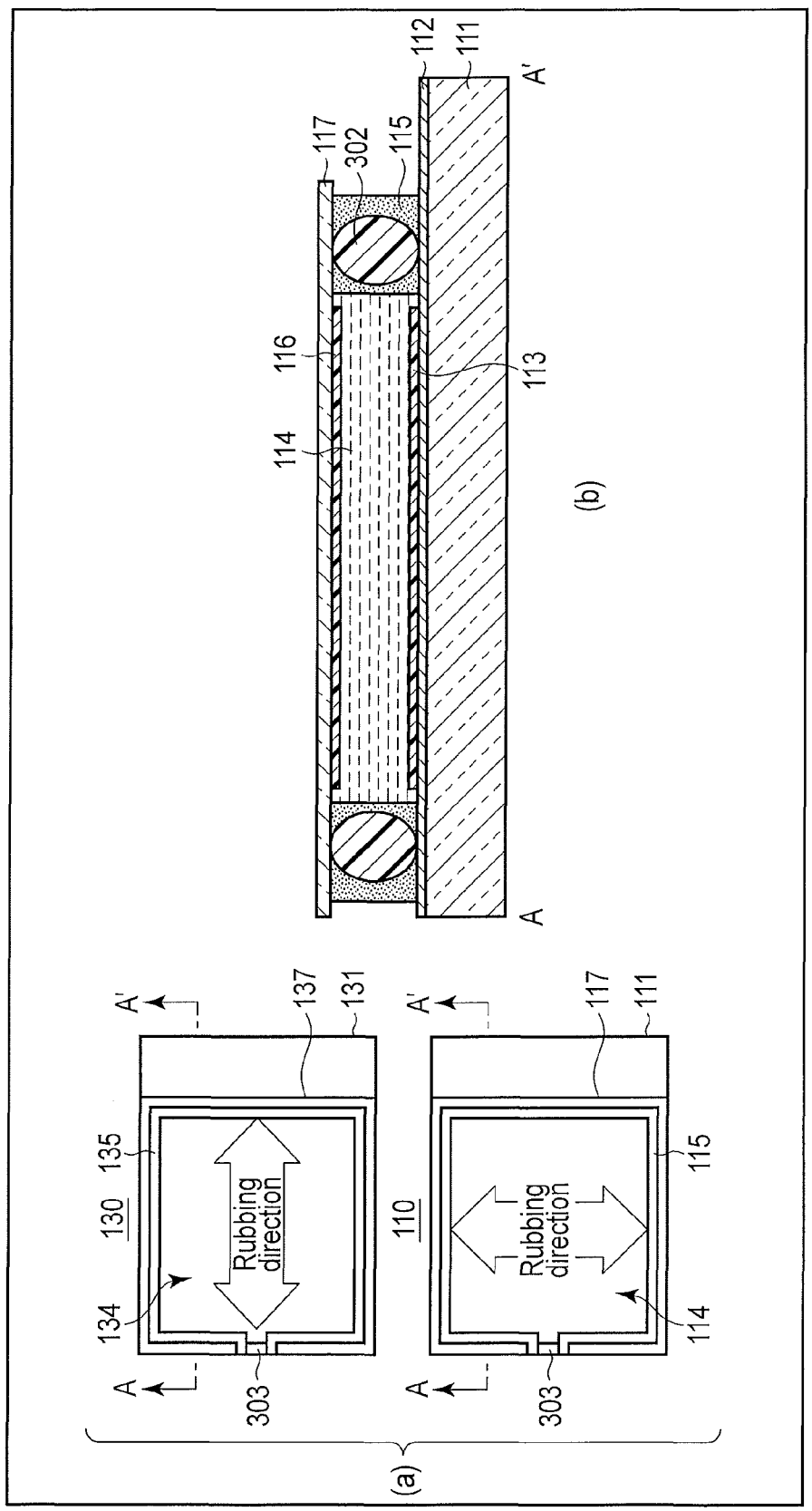
FIG. 26 shows a step of manufacturing a liquid crystal lens according to the fifth embodiment.

In FIG. 26, (a) is a plan view showing the step of manufacturing liquid crystal cells 110 and 130, and (b) is a sectional view taken along a line A-A' of the liquid crystal cell 110 in (a) in FIG. 26. The sectional view of the liquid crystal cell 130 is the same as that shown in (b) in FIG. 26 except that the rubbing directions of the respective alignment films differ from each other. First of all, the liquid crystal cells 110 and 130 are manufactured by the same manufacturing method as that in the fourth embodiment. At this time, the liquid crystal cells 110 and 130 are manufactured such that their rubbing directions differ from each other by 90°. This can be implemented by controlling rubbing processing for alignment films.

That is, in the fourth embodiment, the X and Y lenses are manufactured by disposing the two liquid crystal cells having the same rubbing direction so as to make them cross at 90°, whereas in the fifth embodiment, two liquid crystal cells whose rubbing directions differ from each other by 90° are manufactured at the stage of manufacturing liquid crystal cells. For example, in the fifth embodiment, at the stage of manufacturing the unit 300 in FIG. 14, the respective units of the liquid crystal cells 110 and 130 are manufactured.

Figure 27:
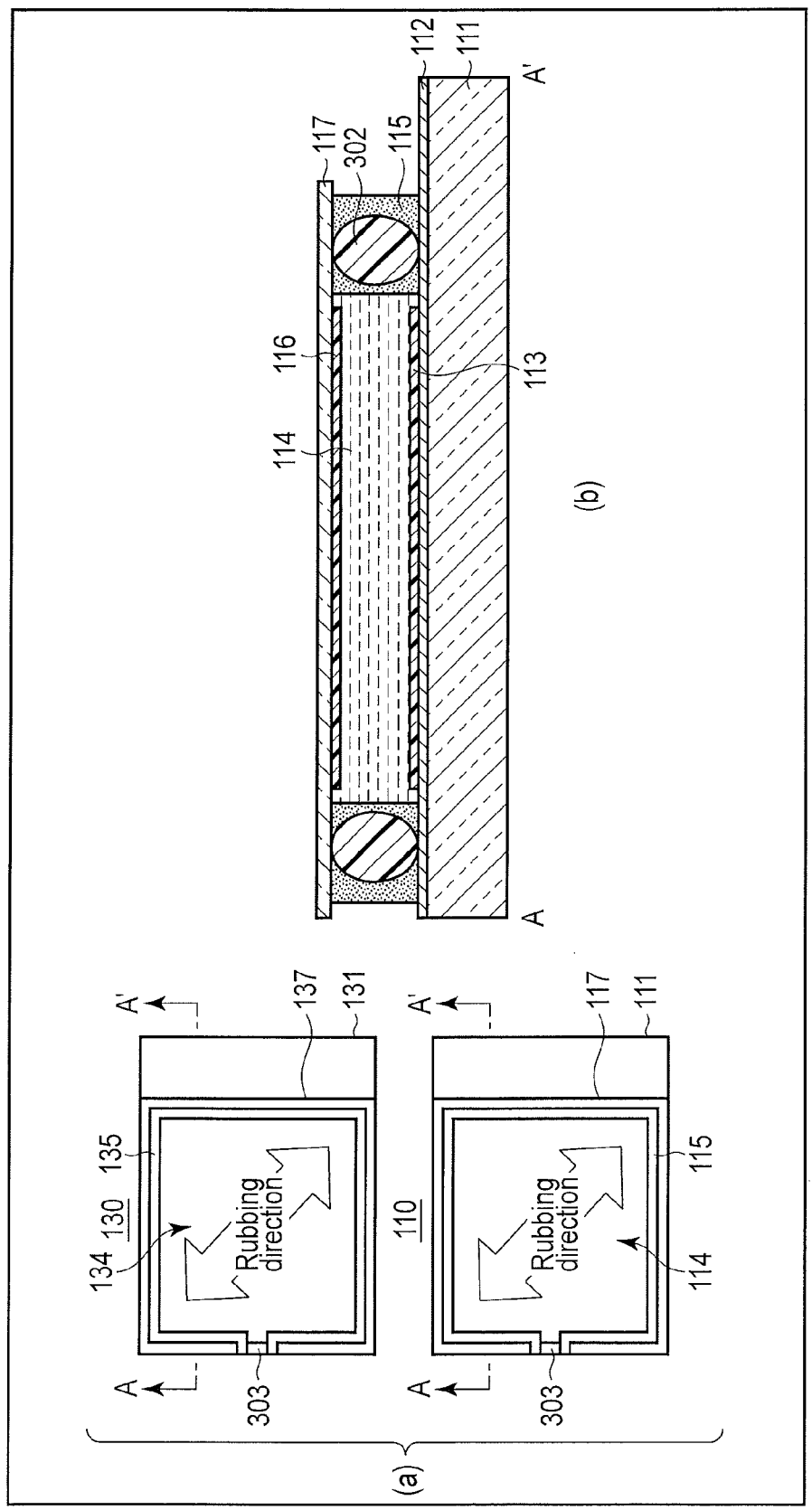
FIG. 27 shows another example of the arrangement of a liquid crystal cell.

As shown in FIG. 27, the rubbing directions of the alignment films in the liquid crystal cells 110 and 130 may be tilted by 45° relative to the horizontal direction.

Figure 28:
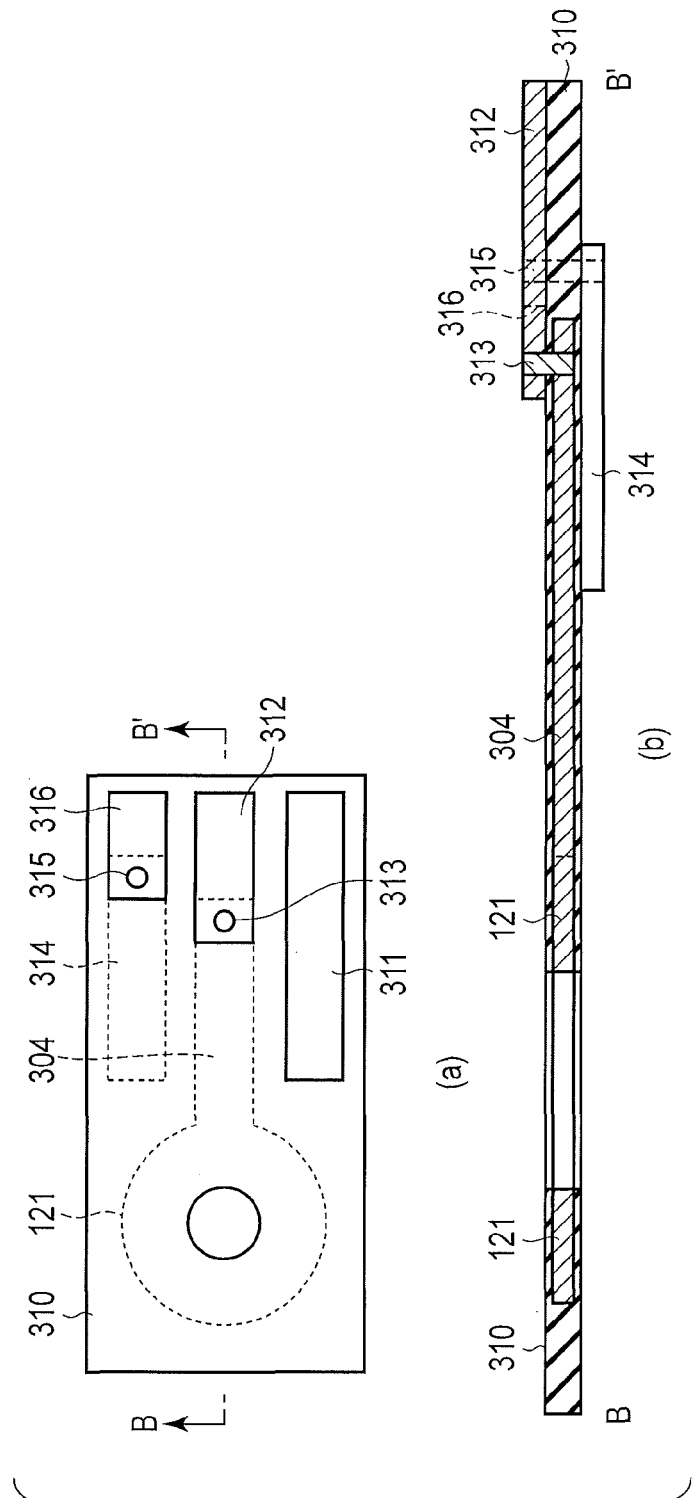
FIG. 28 shows a step of manufacturing the liquid crystal lens following the step in FIG. 26.

Subsequently, as shown in FIG. 28, an insulating FPC (Flexible Printed Circuit) board 310 including a ring-like electrode 121 is manufactured. The board 310 includes three wiring layers. A connecting terminal 311 electrically connected to a transparent electrode 132 of the liquid crystal cell 130 is formed on the upper surface of the board 310.

The ring-like electrode 121 and an extraction electrode 304 electrically connected to the electrode 121 are formed on the intermediate layer of the board 310. A connecting terminal 312 electrically connected to the ring-like electrode 121 is formed on the upper surface of the board 310. The ring-like electrode 121 is electrically connected to the connecting terminal 312 via the extraction electrode 304 and a contact 313.

A connecting terminal 314 electrically connected to a transparent electrode 112 of the liquid crystal cell 110 is formed on the bottom surface of the board 310. A connecting terminal 316 electrically connected to the connecting terminal 314 is formed on the upper surface of the board 310. The connecting terminal 314 is electrically connected to the connecting terminal 316 via a contact 315.

Figure 29:
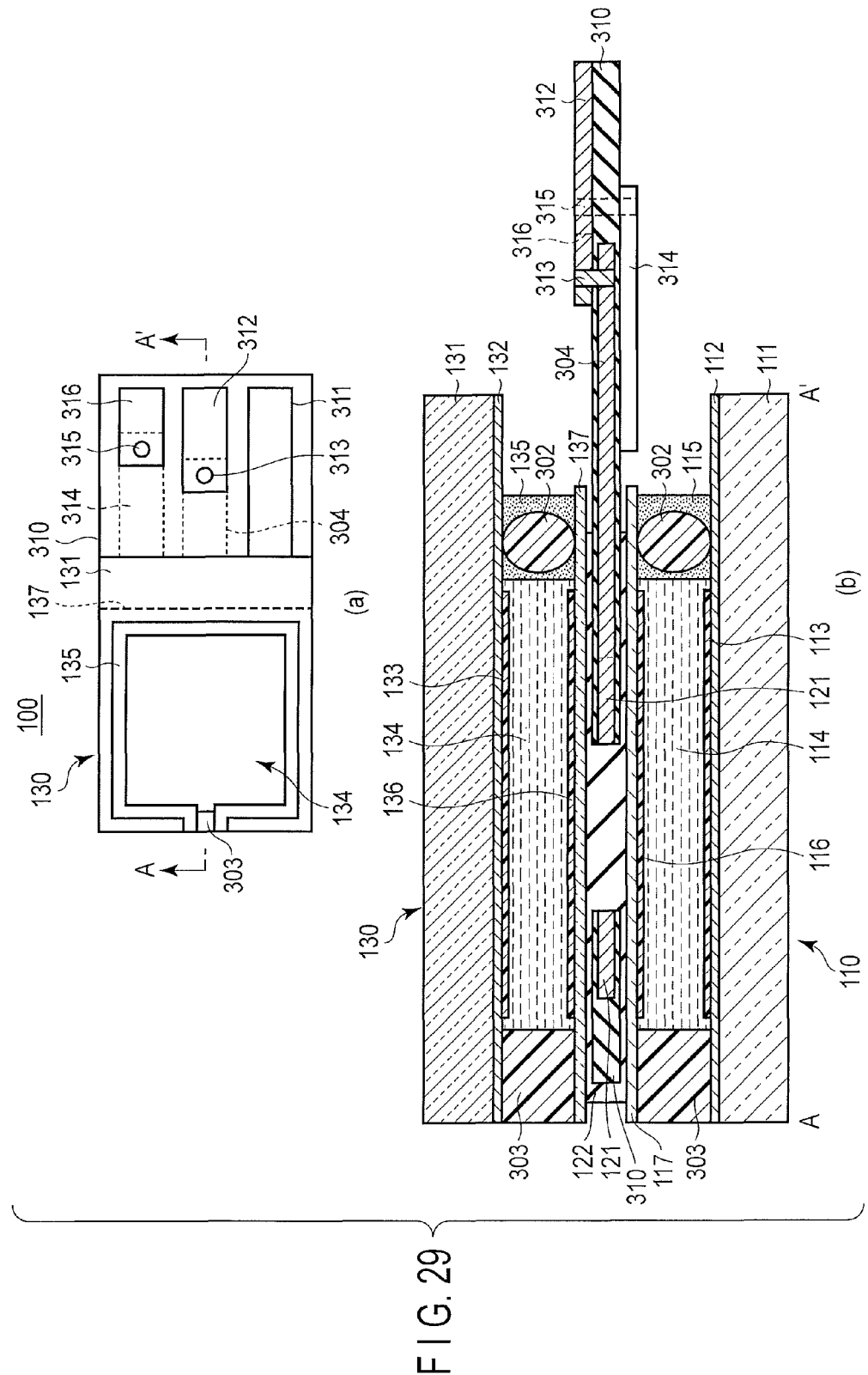
FIG. 29 shows a step of manufacturing the liquid crystal lens following the step in FIG. 28.

Subsequently, after the liquid crystal cell 130 is reversed from the state in FIG. 26, the liquid crystal cell 110 and the liquid crystal cell 130 are bonded to each other so as to sandwich the FPC 310, as shown in FIG. 29. At this time, a liquid or paste binder is used as a high-k layer 122, and the high-k layer 122 is also used as an adhesive with which the liquid crystal cell 110 is bonded to the liquid crystal cell 130.

Figure 30:
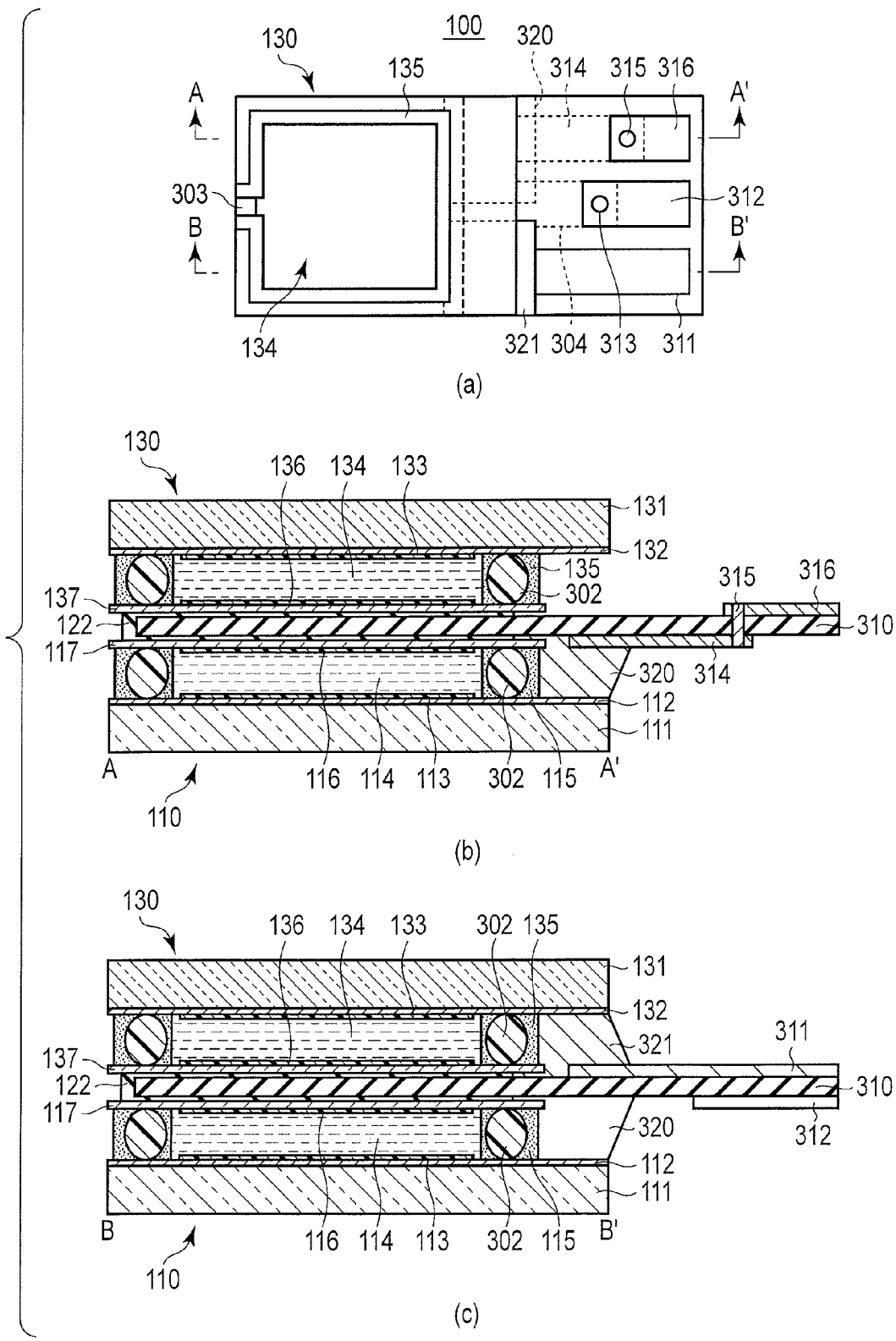
FIG. 30 shows a step of manufacturing the liquid crystal lens following the step in FIG. 29.

Subsequently, a conductive layer 320 which electrically connects the transparent electrode 112 to the connecting terminal 314 is formed between the liquid crystal cell 110 and the FPC 310. Likewise, a conductive layer 321 which electrically connects the transparent electrode 132 to the connecting terminal 311 is formed between the liquid crystal cell 130 and the FPC 310. In FIG. 30, (a) is a plan view showing the step of manufacturing conductive layers, (b) is a sectional view taken along a line A-A' in (a) in FIG. 30, and (c) is a sectional view taken along a line B-B' in (a) in FIG. 30. The conductive layers 320 and 321 are formed by coating the respective prospective formation portions with a conductive paste. With this arrangement, the transparent electrode 112 is electrically connected to the connecting terminal 316, and the transparent electrode 132 is electrically connected to the connecting terminal 311.

(Effects)

As has been described in detail above, according to the fifth embodiment, a liquid crystal lens 100 can include the connecting terminal 316 electrically connected to the transparent electrode 112 of the liquid crystal cell 110, the connecting terminal 312 electrically connected to the ring-like electrode 121, and the connecting terminal 311 electrically connected to the transparent electrode 132 of the liquid crystal cell 130. In addition, it is possible to extract three connecting terminals as wiring layers at the same level at one portion of the liquid crystal lens 100. This makes it possible to implement the liquid crystal lens 100 which can be easily connected to the lens unit.

In addition, since the liquid crystal cell 110 and the liquid crystal cell 130 are bonded to each other upon being aligned with the longitudinal direction, the shape of the liquid crystal lens 100 is free from complexity, and the size of the liquid crystal lens 100 in a direction perpendicular to the longitudinal direction can be reduced. This facilitates housing the liquid crystal lens in the lens unit.

[Sixth Embodiment]

The sixth embodiment is configured to reduce the size and manufacturing cost of a liquid crystal lens 100 while letting it have connecting terminals to the outside as in the fifth embodiment.

Figure 31:
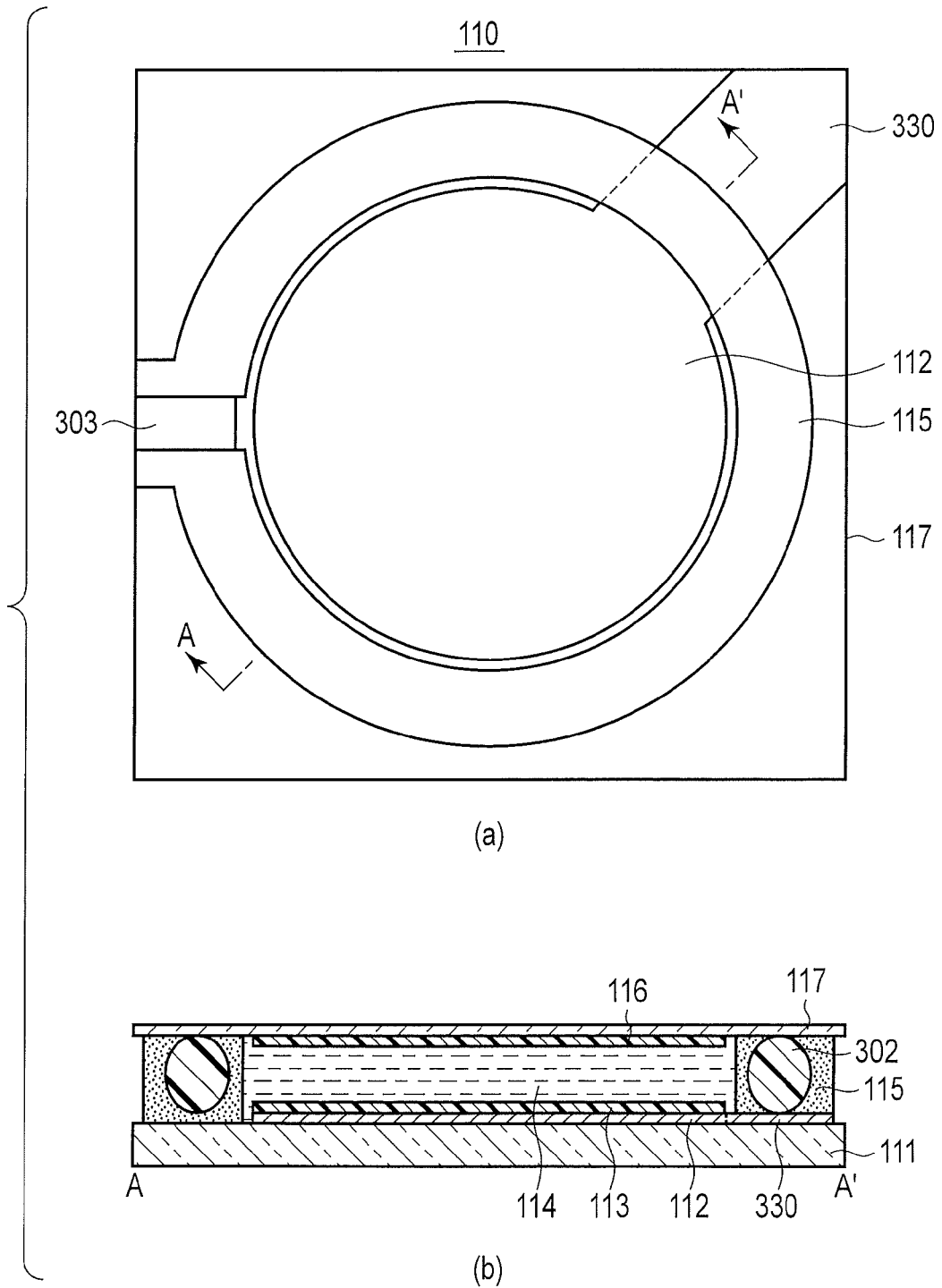
FIG. 31 shows a step of manufacturing a liquid crystal lens according to the sixth embodiment.

In FIG. 31, (a) is a plan view showing the step of manufacturing a liquid crystal cell 110, and (b) is a sectional view taken along a line A-A' in (a) in FIG. 31. The liquid crystal cell 110 has, for example, a square shape and is 8 mm-square or less. A seal member 115 of the liquid crystal cell 110 has a circular outer shape. A transparent electrode 112 in the liquid crystal cell 110 also has a circular shape. When patterning the transparent electrode 112 into a circular shape, an extraction electrode 330 electrically connected to the transparent electrode 112 is formed. The extraction electrode 330 is extracted from the transparent electrode 112 to the upper right corner of the liquid crystal cell 110. A liquid crystal cell 130 has the same arrangement as that shown in FIG. 31. The manufacturing steps up to the step of discretizing the liquid crystal cells 110 and 130 are the same as those in the fourth embodiment. Liquid crystals are then injected into the liquid crystal cells 110 and 130, and the opening portion of each seal member is sealed with a seal member 303.

Figure 32:
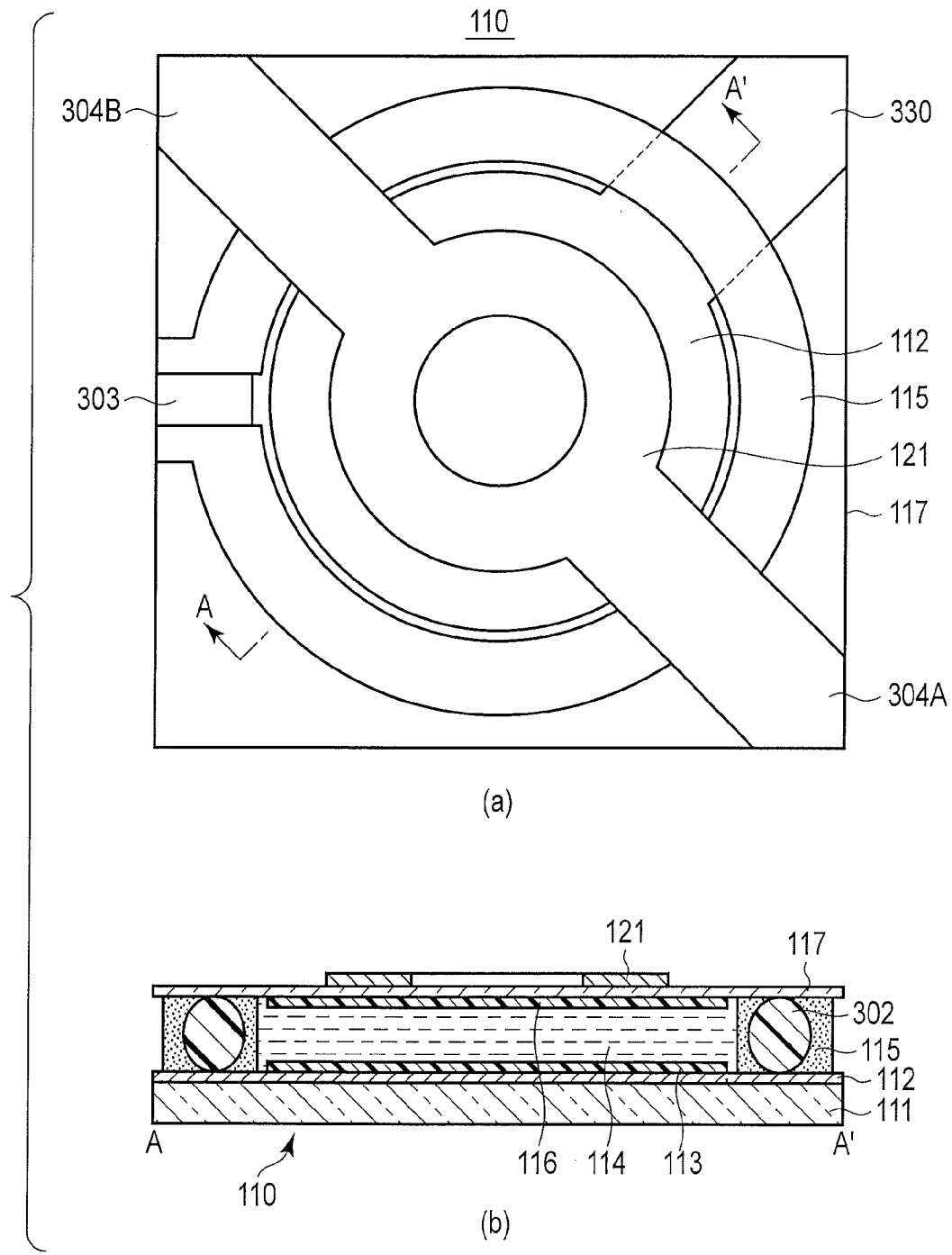
FIG. 32 shows a step of manufacturing the liquid crystal lens following the step in FIG. 31.

Subsequently, as shown in FIG. 32, a ring-like electrode 121 concentric with the transparent electrode 112 is formed on a glass substrate 117 of the liquid crystal cell 110. When patterning the ring-like electrode 121, extraction electrodes 304A and 304B electrically connected to the ring-like electrode 121 are formed. The extraction electrodes 304A and 304B are extracted from the ring-like electrode 121 to the upper left and lower right of the liquid crystal cell 110.

Subsequently, a high-k layer 122 is formed on a glass substrate 137 of the liquid crystal cell 130. In FIG. 33, (a) is a plan view showing the step of manufacturing the high-k layer 122, and (b) is a sectional view taken along a line B-B' in (a) in FIG. 33. The liquid crystal cell 130 is identical to the liquid crystal cell 110. Therefore, the liquid crystal cell 130 includes an extraction electrode 331 extracted from a transparent electrode 132 to the upper right corner of the liquid crystal cell 130. The high-k layer 122 is formed to cover the entire transparent electrode 132.

Figure 34:
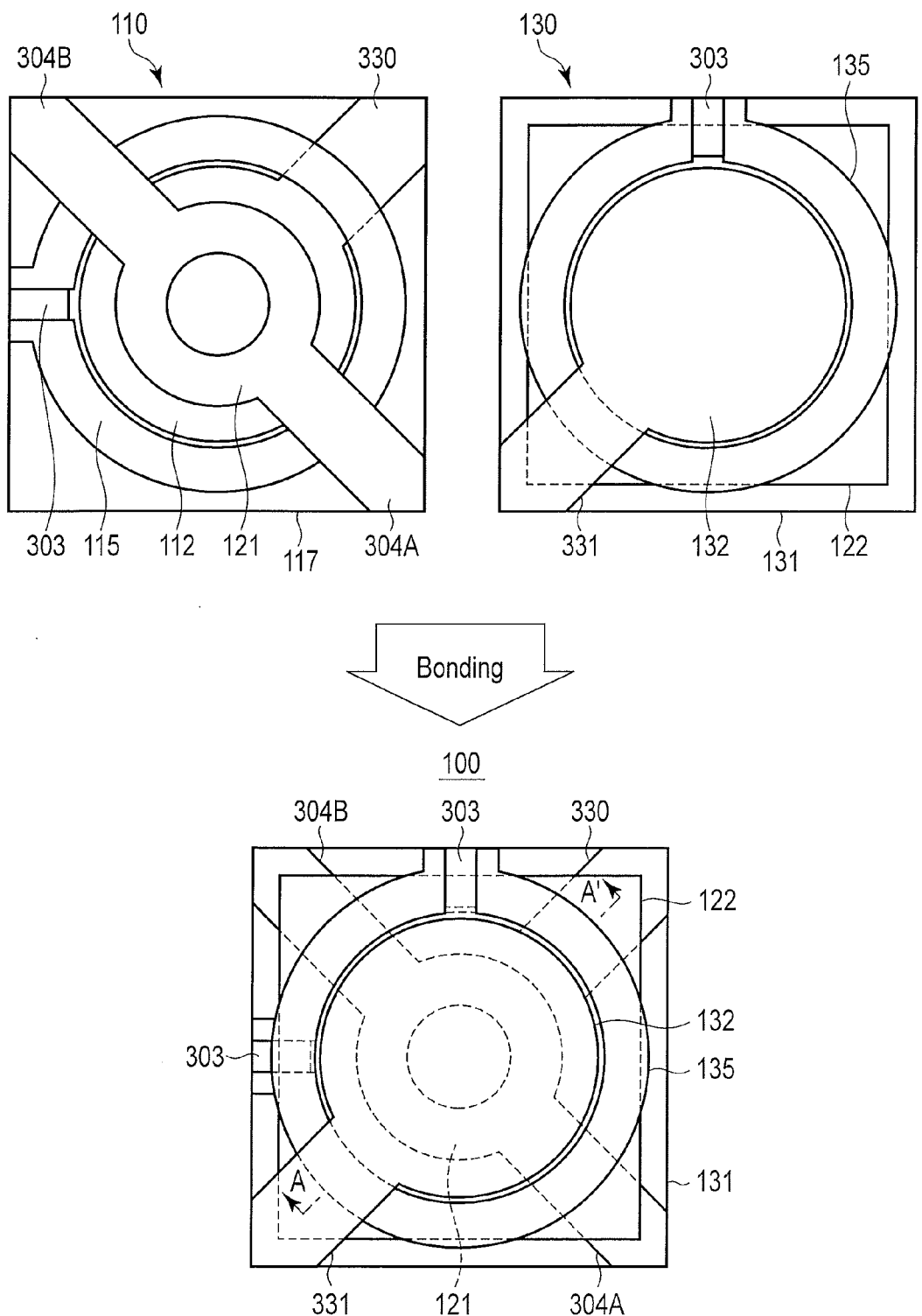
FIG. 34 is a plan view showing a step of manufacturing the liquid crystal lens following the step in FIG. 33.
Figure 35:
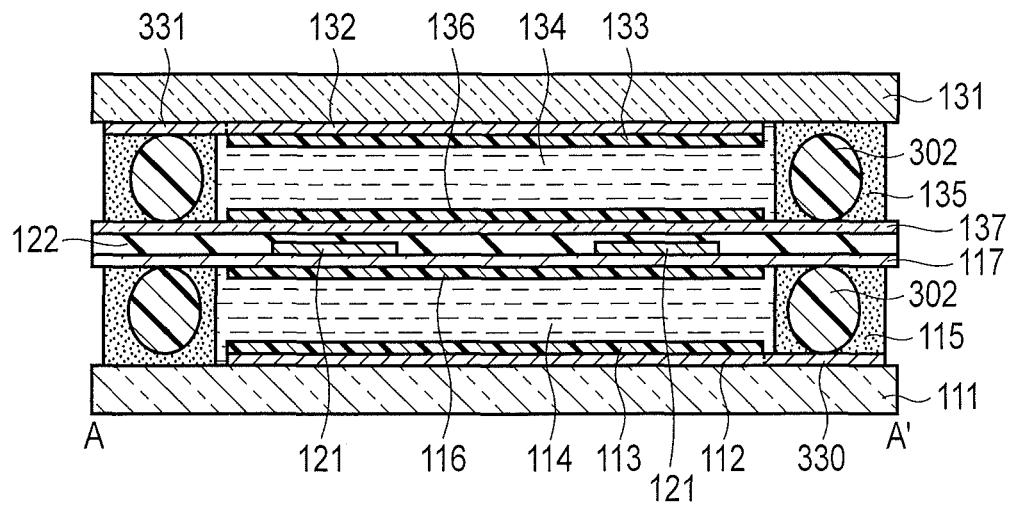
FIG. 35 is a sectional view taken along a line A-A' in FIG. 34 and showing a step of manufacturing the liquid crystal lens.

Subsequently, the liquid crystal cell 110 and the liquid crystal cell 130 are bonded to each other while the liquid crystal cell 130 is reversed from the state shown in FIG. 33 and is rotated leftward through 90°. FIG. 34 is a plane view for explaining this bonding step. FIG. 35 is a sectional view taken along a line A-A' in FIG. 34. More specifically, as in the fourth embodiment, the high-k layer 122 has a thermosoftening property and causes a curing reaction upon irradiation with UV. The two liquid crystal cells are pressurized while the high-k layer 122 is heated to be softened. This exposes the extraction electrode 330 electrically connected to the transparent electrode 112 and the extraction electrode 331 electrically connected to the transparent electrode 132 at one pair of diagonal corners of the liquid crystal lens 100. In addition, the extraction electrodes 304A and 304B electrically connected to the ring-like electrode 121 are exposed at the other pair of diagonal corners of the liquid crystal lens 100.

Figure 36:
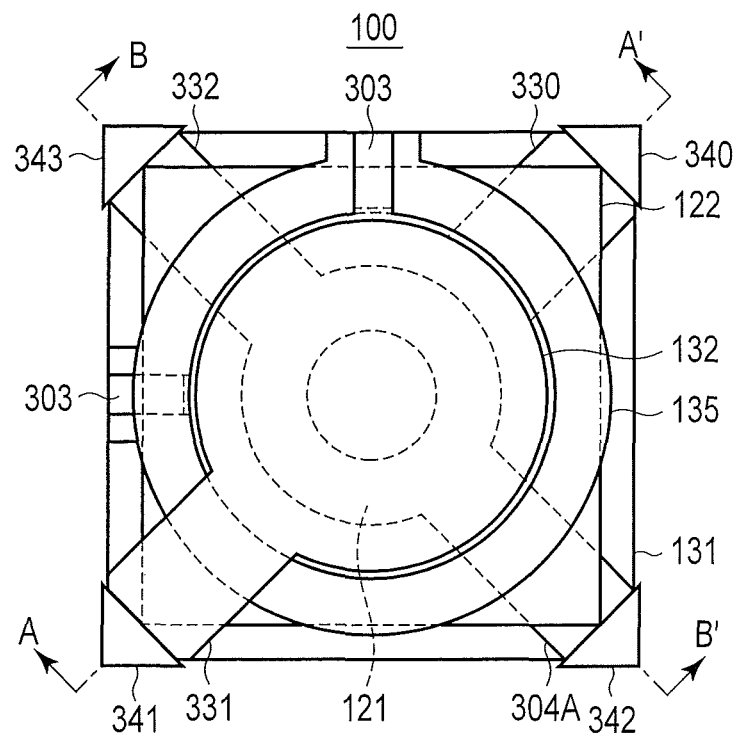
FIG. 36 is a plan view showing a step of manufacturing the liquid crystal lens following the step in FIG. 35.

Subsequently, connecting terminals to the outside (a lens unit and the like) are formed. FIG. 36 is a plan view for explaining the step of forming connecting terminals. In FIG. 37, (a) is a sectional view taken a line A-A' in FIG. 36, and (b) is a sectional view taken along a line B-B' in FIG. 36. Connecting terminals 340 to 343 are respectively formed on the four corners of the liquid crystal lens 100 by coating the four corners of the liquid crystal lens 100 with a conductive paste. This conductive paste is applied to the upper and bottom surfaces of the liquid crystal lens 100 so as to be exposed. This forms the connecting terminal 340 electrically connected to the transparent electrode 112 via the extraction electrode 330, the connecting terminal 341 electrically connected to the transparent electrode 132 via the extraction electrode 331, and the connecting terminals 342 and 343 electrically connected to the ring-like electrode 121 via the extraction electrodes 304A and 304B.

(Effects)

As described in detail above, according to the sixth embodiment, it is possible to make the liquid crystal lens 100 include the connecting terminals to the lens unit incorporated in it while reducing the size of the liquid crystal lens 100. In addition, it is possible to extract the connecting terminals 340 to 343 to the upper and bottom surfaces of the liquid crystal lens 100. This makes it possible to implement the liquid crystal lens 100 which can be easily connected to the lens unit.

In addition, since external connecting terminals can be formed without using any FPC used in the fifth embodiment, it is possible to reduce the manufacturing cost of the liquid crystal lens 100.

Furthermore, it is possible to manufacture the two liquid crystal cells 110 and 130 by using one unit including two pieces of mother glass. This makes it possible to reduce the manufacturing cost of the liquid crystal lens 100.

[Seventh Embodiment]

The seventh embodiment exemplifies the arrangement of a camera module 1 including the liquid crystal lens 100 according to each embodiment described above. The camera module 1 having a focus adjustment function will be described first. FIG. 38 is a schematic view showing the arrangement of the camera module 1 having the focus adjustment function. The camera module 1 includes a lens unit 2 and an imaging device 3.

The imaging device 3 is a semiconductor element which captures light entering from the lens unit 2 and converts the amount of captured light into an electrical signal. The imaging device 3 is formed from, for example, a CMOS image sensor and includes a plurality of pixels. Each pixel includes a photoelectric conversion element (photodiode), color filter, and microlens (condenser lens).

The lens unit 2 includes a fixed lens group 4 and the liquid crystal lens 100. The fixed lens group 4 and the liquid crystal lens 100 are respectively fixed at specific positions. The fixed lens group 4 has a fixed focal length and functions as a single focus lens. The fixed lens group 4 is constituted by a plurality of lenses so as to obtain a desired focal length, and is configured to focus light transmitted through the plurality of lenses at a predetermined focal length. The fixed lens group 4 functions as a convex lens. The fixed lens group 4 may be formed from one fixed lens having a fixed focal length.

Figure 39:
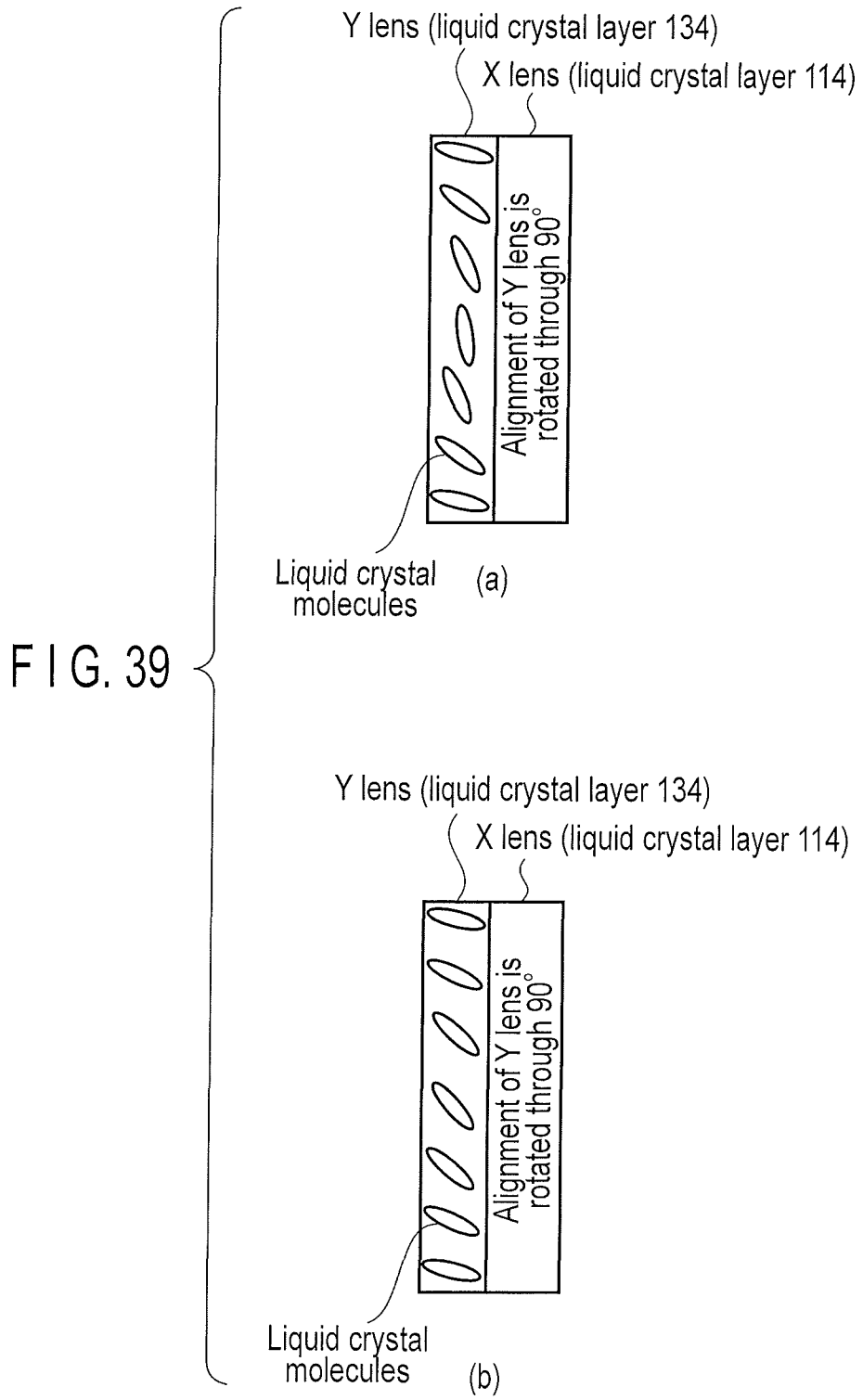
FIG. 39 explains the alignment of a liquid crystal lens.

The liquid crystal lens 100 uses a homogeneously aligned liquid crystal layer. That is, the liquid crystal lens 100 functions as a convex lens with a variable focal length and positive lens power. FIG. 39 explains the alignment of the liquid crystal lens 100. In FIG. 39, (a) shows the alignment state of the liquid crystal lens 100 in (a) in FIG. 38, and (b) shows the alignment state of the liquid crystal lens 100 in (b) in FIG. 38.

In FIG. 38, (a) is an optical path diagram in a state in which object A at a distance Da from the imaging device 3 is focused. FIG. 38 shows a refracting surface as a principal surface when the lens unit 2 is viewed as one lens.

As indicated by (a) in FIG. 39, voltage gradients are applied to homogeneously aligned liquid crystal layers 114 and 134 to form a gradient distribution such that the long axes of liquid crystal molecules are aligned in the in-plane direction at the lens central portion and are gradually aligned in a direction perpendicular to the in-plane direction toward the lens peripheral portion. Setting the focal length of the lens unit 2 to f1 will form an image of object A as image A on the imaging device 3. On the other hand, an image of object B at a distance Db from the imaging device 3 is formed in front of the imaging plane of the imaging device 3, and hence an image of object B which is not formed on the imaging device 3 blurs.

In FIG. 38, (b) is an optical path diagram in a state in which object B at the distance Db from the imaging device 3 is focused. As indicated by (b) in FIG. 39, voltage gradients are applied to homogeneously aligned liquid crystal layers 114 and 134 to form a gradient distribution such that the long axes of liquid crystal molecules are aligned in a direction almost perpendicular to the in-plane direction at the lens central portion relative to the state in (a) in FIG. 39. Setting the focal length of the lens unit 2 to f2 will form an image of object B as image B on the imaging device 3. On the other hand, an image of object A at the distance Da from the imaging device 3 is formed behind the imaging plane of the imaging device 3, and hence an image of object A which is not formed on the imaging device 3 blurs.

Adjusting the focal length of the liquid crystal lens 100 incorporated in the lens unit 2 can adjust the focal length of the lens unit 2 and the position of the principal surface. This makes it possible to add the focus adjustment function to the camera module 1.

Figure 40:
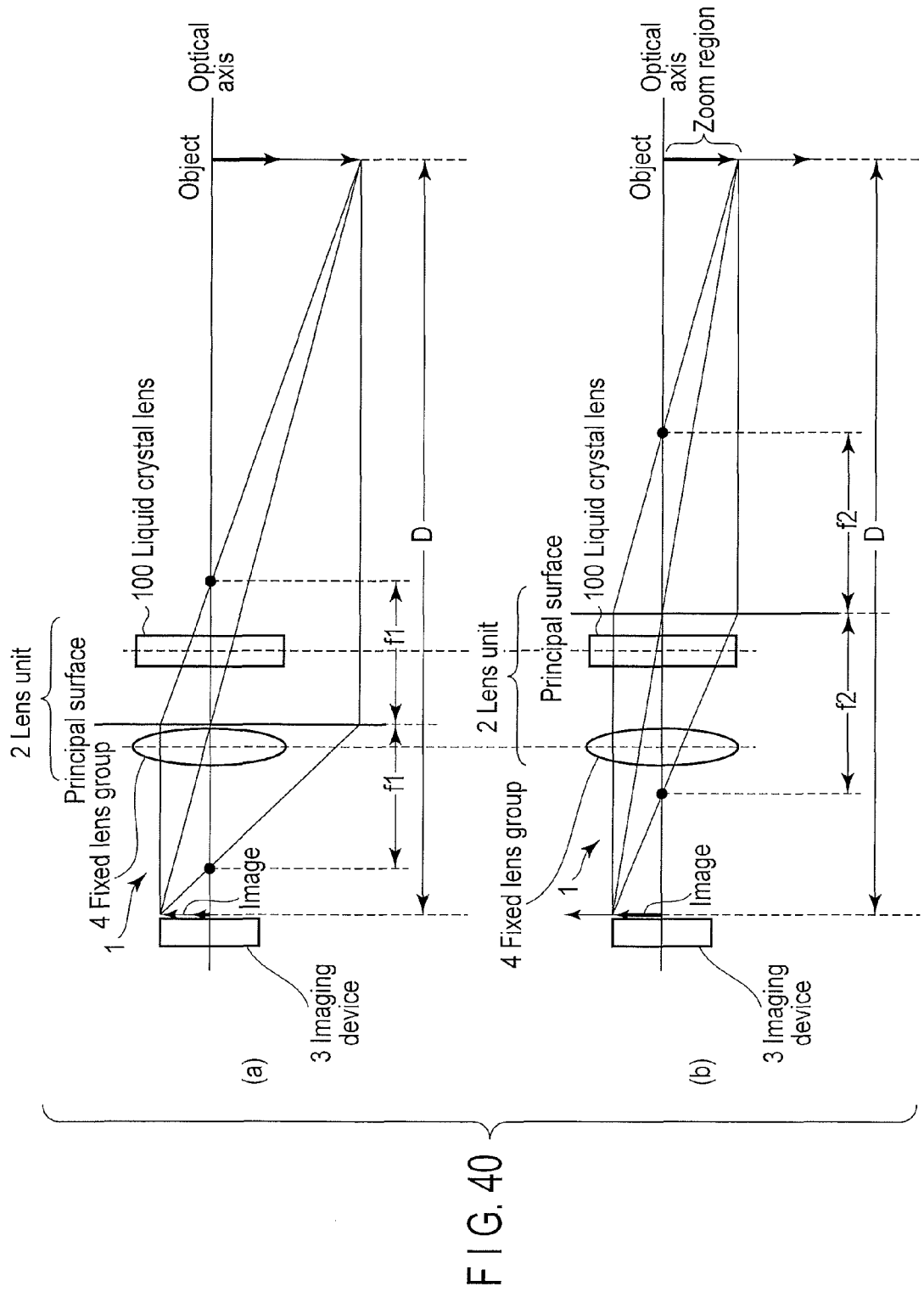
FIG. 40 shows the arrangement of a camera module having an angle-of-view adjustment function according to the seventh embodiment.

The camera module 1 having the angle-of-view adjustment function will be described next. FIG. 40 schematically shows the arrangement of the camera module 1 having the angle-of-view adjustment function.

Figure 41:
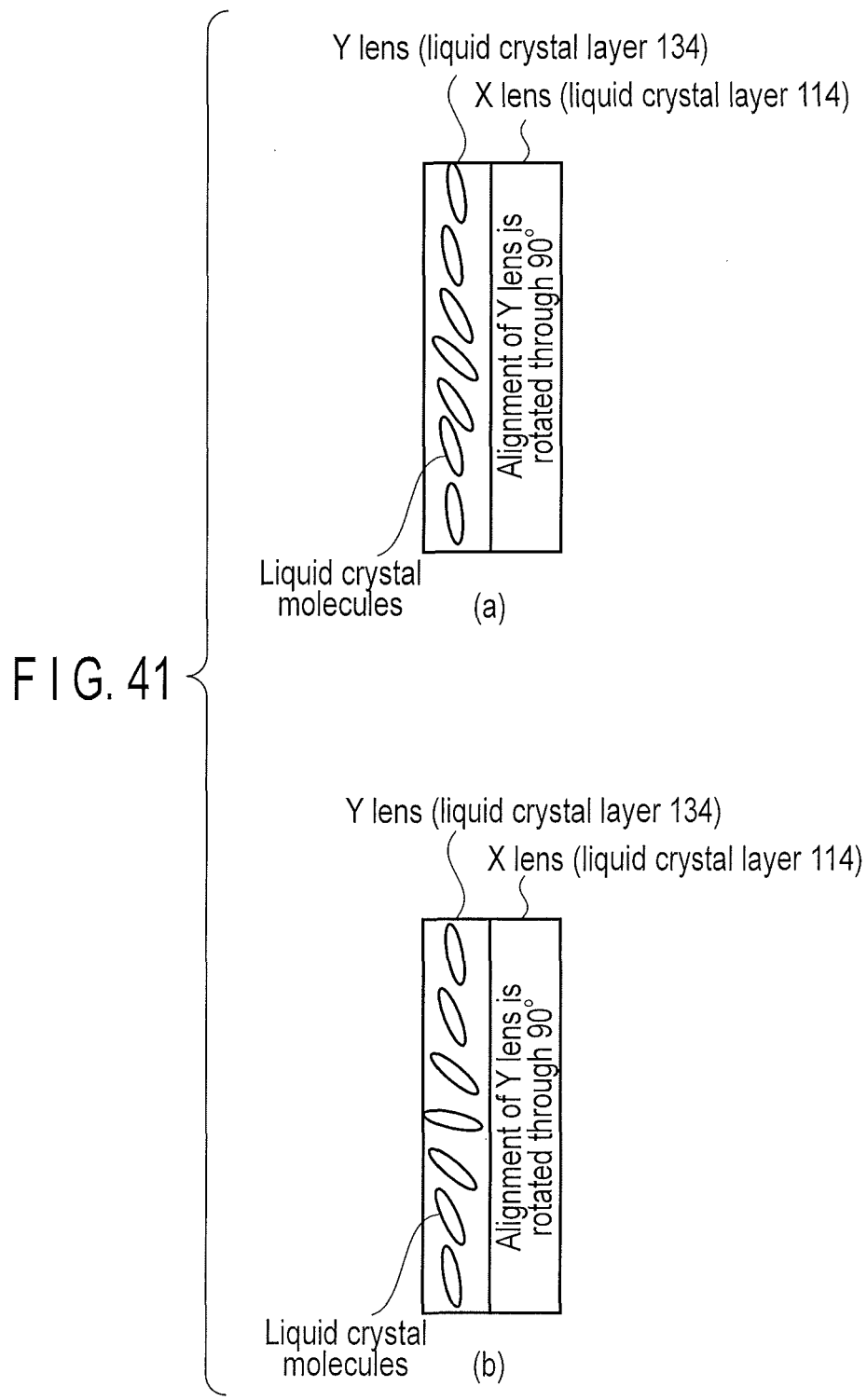
FIG. 41 explains the alignment of a liquid crystal lens.

The liquid crystal lens 100 uses homeotropically aligned liquid crystal layers. That is, the liquid crystal lens 100 functions as a concave lens with a variable focal length and negative lens power. FIG. 41 explains the alignment of the liquid crystal lens 100. In FIG. 41, (a) shows the alignment state of the liquid crystal lens 100 in (a) in FIG. 40, and (b) shows the alignment state of the liquid crystal lens 100 in (b) in FIG. 40.

In FIG. 40, (a) is an optical path diagram in a state in which an object at a distance D from the imaging device 3 is focused. As indicated by (a) in FIG. 41, voltage gradients are applied to the homeotropically aligned liquid crystal layers 114 and 134 to form a gradient distribution such that the long axes of liquid crystal molecules are aligned in the in-plane direction as a whole. The lens power of the liquid crystal lens 100 at this time is almost 0. Setting the focal length of the lens unit 2 to f1 forms an overall image of the object on the imaging device 3.

In FIG. 40, (b) shows an optical path diagram in a state in which a portion of an object at the distance D from the imaging device 3 is enlarged. As indicated by (b) in FIG. 41, voltage gradients are applied to the homeotropically aligned liquid crystal layers 114 and 134 to form a gradient distribution such that the long axes of liquid crystal molecules are aligned in a direction almost perpendicular to the in-plane direction at the lens central portion and are gradually aligned in the in-plane direction toward the lens peripheral portion. Setting the focal length of the lens unit 2 to f2 will form an enlarged image of a portion (zoom region) of the object on the imaging device 3.

As described above, it is possible to adjust the focal length of the lens unit 2 and the position of the principal surface by adjusting the focal length of the liquid crystal lens 100 incorporated in the lens unit 2. This can add an angle-of-view adjustment function to the camera module 1.

Figure 42:
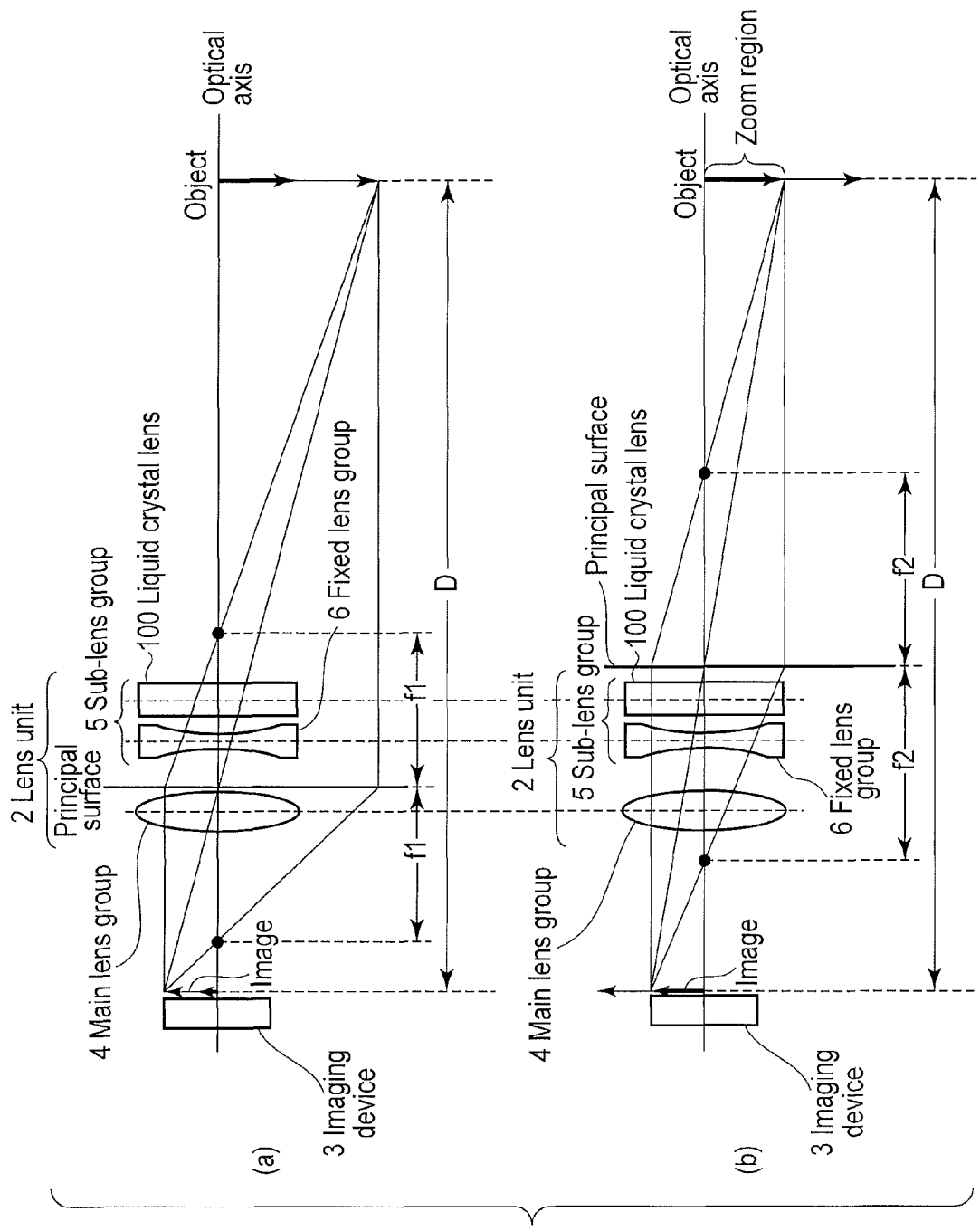
FIG. 42 schematically shows another arrangement of a camera module having an angle-of-view adjustment function.

FIG. 42 shows another arrangement of the camera module 1 having the angle-of-view adjustment function. The lens unit 2 includes a main lens group 4 and a sub-lens group 5. The sub-lens group 5 includes a fixed lens group 6 and the liquid crystal lens 100. The main lens group 4 and the sub-lens group 5 are respectively fixed at specific positions.

The main lens group 4 has a fixed focal length and functions as a single focus lens. The main lens group 4 functions as a convex lens. The main lens group 4 may be formed from one main lens having a fixed focal length. The fixed lens group 6 has a fixed focal length and functions as a single focus lens. The fixed lens group 6 functions as a concave lens. The fixed lens group 6 may be formed from one fixed lens having a fixed focal length.

The liquid crystal lens 100 uses homogeneously aligned liquid crystal layers. That is, the liquid crystal lens 100 functions as a convex lens with a variable focal length and positive lens power.

In FIG. 42, (a) shows an optical path diagram in a state in which an object at the distance D from the imaging device 3 is focused. The alignment state of the liquid crystal lens 100 is the same as that in (a) in FIG. 39. The focal length of the lens unit 2 is set to f1 by controlling voltages to the liquid crystal lens 100. This forms an overall image of the object on the imaging device 3. Assume that the focal length of the main lens group 4 is designed to focus the object with only the main lens group 4. In this case, the focal length of the liquid crystal lens 100 is adjusted to set the refractive index of the sub-lens group 5 to 1 (that is, to make the sub-lens group 5 refract almost no light).

In FIG. 42, (b) shows an optical path diagram in a state in which a portion of an object at the distance D from the imaging device 3 is enlarged. The alignment state of the liquid crystal lens 100 is the same as that in (b) in FIG. 39. The focal length of the lens unit 2 is set to f2 by controlling voltages to the liquid crystal lens 100. This forms an enlarged image of the portion (zoom region) of the object on the imaging device 3. Assume that the focal lengths of the main lens group 4 and fixed lens group 6 are designed to form an image of the zoom region of the object on the imaging device 3 with the main lens group 4 and the fixed lens group 6. In this case, voltages to the liquid crystal lens 100 are controlled to set the lens power of the liquid crystal lens 100 to almost 0.

(Example of Camera Module 1)

Figure 43:
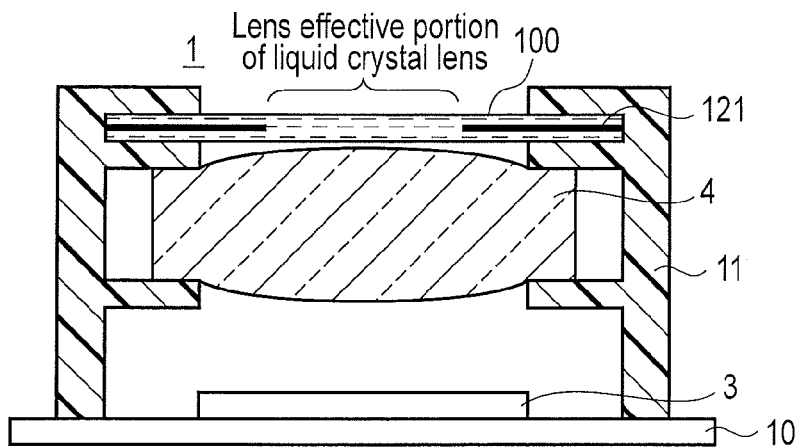
FIG. 43 is a sectional view showing the arrangement of a camera module according to Example 1.

A concrete example of the arrangement of the camera module 1 according to the seventh embodiment will be described next. FIG. 43 is a sectional view showing the arrangement of the camera module 1 according to Example 1.

The imaging device 3 is provided on a peripheral circuit board 10. The fixed lens group 4 and the liquid crystal lens 100 are sequentially arranged above the imaging device 3. A lens holder (support body) 11 holds the fixed lens group 4 and the liquid crystal lens 100. The lens holder 11 is formed into a cylindrical shape so as to surround the imaging device 3. The lens holder 11 is formed from, for example, a resin. The lens holder 11 is bonded to the peripheral circuit board 10 with, for example, an adhesive.

The liquid crystal lens 100 and the imaging device 3 are wired to the peripheral circuit board 10. The peripheral circuit board 10 includes a control circuit for driving and controlling an imaging device 33 and the liquid crystal lens 100, and also includes a voltage control circuit 200.

Figure 44:
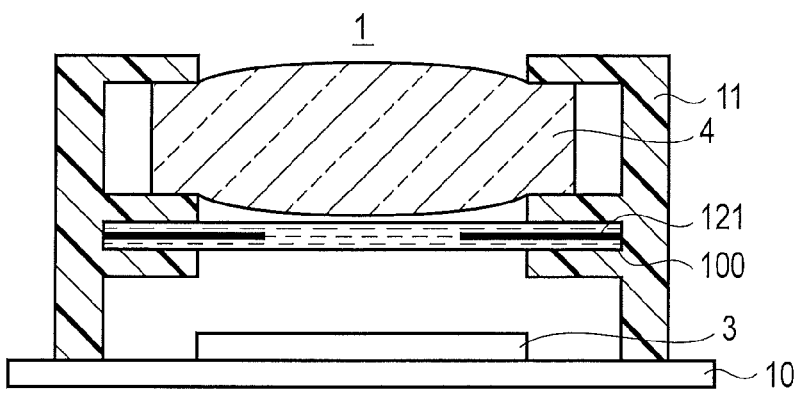
FIG. 44 is a sectional view showing the arrangement of a camera module according to Example 2.

FIG. 44 is a sectional view showing the arrangement of the camera module 1 according to Example 2. The liquid crystal lens 100 and the fixed lens group 4 are sequentially arranged above the imaging device 3. That is, the liquid crystal lens 100 is disposed on the imaging device 3 side.

Figure 45:
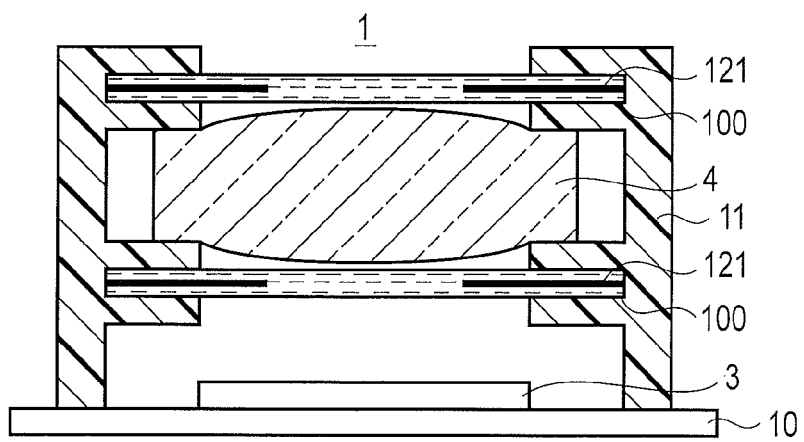
FIG. 45 is a sectional view showing the arrangement of a camera module according to Example 3.

FIG. 45 is a sectional view showing the arrangement of the camera module 1 according to Example 3. The liquid crystal lens 100, the fixed lens group 4, and the liquid crystal lens 100 are sequentially arranged above the imaging device 3. That is, the camera module 1 according to Example 3 includes two liquid crystal lenses 100 so as to sandwich the fixed lens group 4.

The positions of the liquid crystal lenses 100 and fixed lens group 4 can be freely designed. In addition, the numbers of liquid crystal lenses 100 and fixed lenses can be freely designed. It is possible to implement the camera module 1 having a focus adjustment function and an angle-of-view adjustment function by selecting one of Examples 1 to 3 in accordance with the characteristics of lens groups to be combined.

(Effects)

As described in detail above, the seventh embodiment is configured to implement the camera module 1 by using the liquid crystal lens 100 including the two liquid crystal layers which are homogeneously aligned so as to make the initial alignment directions differ from each other by 90°, the fixed lens group 4, and the imaging device 3. The focal length of the liquid crystal lens 100 is changed by controlling voltage gradients applied to the liquid crystal lens 100. This makes it possible to implement the camera module 1 having a focus adjustment function.

In addition, the camera module 1 is formed by using the liquid crystal lens 100 including the two liquid crystal layers homeotropically aligned such that the respective alignment directions are slightly tilted in directions differing from each other by 90°, the fixed lens group 4, and the imaging device 3. The focal length of the liquid crystal lens 100 is changed by controlling voltage gradients applied to the liquid crystal lens 100. This makes it possible to implement the camera module 1 having an angle-of-view adjustment function.

In addition, since it is possible to implement the camera module 1 to which the focus adjustment function and the angle-of-view adjustment function are added without using any mechanism such as a voice coil motor, it is possible to implement the downsizing of the camera module 1.

[Eighth Embodiment]

Figure 46:
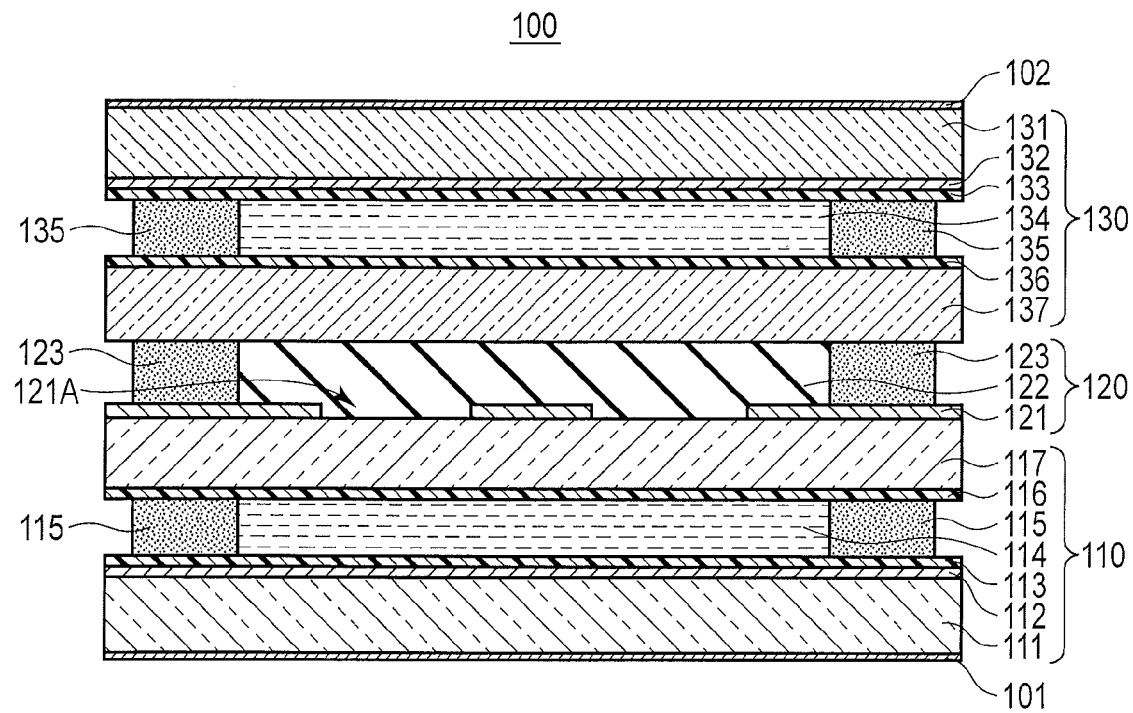
FIG. 46 is a sectional view showing the arrangement of a fly-eye liquid crystal lens according to the eighth embodiment.
Figure 47:
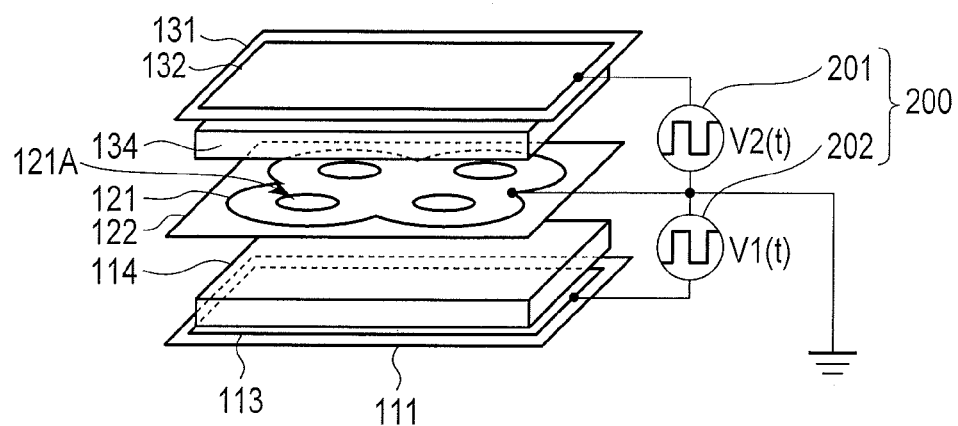
FIG. 47 is a perspective view showing the arrangement of a fly-eye liquid crystal lens.

The eighth embodiment exemplifies the arrangement of a fly-eye (compound eye) liquid crystal lens to be used to generate stereoscopic images. FIG. 46 is a sectional view showing the arrangement of a fly-eye liquid crystal lens 100 according to the eighth embodiment. FIG. 47 is a perspective view showing the arrangement of the fly-eye liquid crystal lens 100. An intermediate layer 120 is provided between a first liquid crystal cell 110 and a second liquid crystal cell 130. The first and second liquid crystal cells 110 and 130 have the same arrangements as those in FIG. 1. The first liquid crystal cell 110 has a transparent substrate 117 disposed in contact with the intermediate layer 120. The second liquid crystal cell 130 has a transparent substrate 137 disposed in contact with the intermediate layer 120.

The intermediate layer 120 includes an electrode 121 and a high-k layer 122. The electrode 121 includes a plurality of circular opening portions 121A. Each opening portion 121A corresponds to the lens aperture (lens effective region) of each lens of the fly-eye lens. The plurality of opening portions 121A have the same diameter. FIGS. 46 and 47 exemplify a case in which the number of opening portions 121A is four. The four opening portions 121A are arranged in a square shape. Note that it is possible to arbitrarily set the number of opening portions 121A as long as the number is two or more. Other arrangements are the same as those in FIG. 1.

A voltage control method for the fly-eye liquid crystal lens 100 is the same as that in the first embodiment. The fly-eye liquid crystal lens 100 includes a plurality of lens portions corresponding to the plurality of opening portions 121A. Each lens portion operates in the same manner as the liquid crystal lens in the first embodiment. Therefore, the plurality of lens portions corresponding to the plurality of opening portions 121A have the same focal length, and each can change its optical length. In addition, the eighth embodiment can equally control the focal lengths of the plurality of lens portions of the fly-eye liquid crystal lens 100 merely by using one electrical signal for controlling a voltage to the electrode 121.

(Arrangement of Multieye Camera Module 1)

The arrangement of the multieye camera module 1 including the fly-eye liquid crystal lens 100 will be described next. The multieye camera module 1 which does not include the fly-eye liquid crystal lens 100 will be described first. FIG. 48 is a plan view showing the arrangement of the multieye camera module 1 according to Example 1. FIG. 49 is sectional view showing the arrangement of the multieye camera module 1 according to Example 1.

An imaging device 3 is provided on the peripheral circuit board 10. A fly-eye lens 4 is disposed above the imaging device 3. Each lens of the fly-eye lens 4 has a fixed focal length and functions as a single focus lens. The fly-eye lens 4 may be configured to obtain desired lens characteristics by combining a plurality of fly-eye lenses. The fly-eye lens 4 is formed by, for example, arranging four lenses in a square shape. The number of lenses constituting the fly-eye lens 4 can be arbitrarily set as long as the number is two or more. A lens holder 11 holds the fly-eye lens 4. The lens holder 11 is formed into a cylindrical shape so as to surround the imaging device 3. Portions of the lens holder 11 which hold the fly-eye lens 4 have opening portions each having the same circular shape as that of each lens. The lens holder 11 is bonded to the peripheral circuit board 10 with, for example, an adhesive.

FIG. 50 is a sectional view showing the arrangement of the multieye camera module 1 according to Example 2. The fly-eye lens 4 and the fly-eye liquid crystal lens 100 are sequentially arranged above the imaging device 3. That is, the fly-eye lens 4 is disposed on the imaging device 3 side. The lens holder 11 holds the fly-eye lens 4 and the fly-eye liquid crystal lens 100. The number of lenses of the fly-eye liquid crystal lens 100 is the same as that of the fly-eye lens 4. The four opening portions 121A (lens portions) of the electrode 121 of the fly-eye liquid crystal lens 100 are arranged above the four lenses constituting the fly-eye lens 4. One lens portion of the fly-eye liquid crystal lens 100 is disposed on the optical axis of one lens of the fly-eye lens 4. This allows one lens unit constituted by one lens of the fly-eye liquid crystal lens 100 and one lens of the fly-eye lens 4 to implement the same focus adjustment function as that shown in FIGS. 38 and 39 when using homogenous alignment for each liquid crystal layer. If homeotropic alignment is used for each liquid crystal layer, it is possible to implement the same angle-of-view adjustment function as that shown in FIGS. 40 and 41.

FIG. 51 is a sectional view showing the arrangement of the multieye camera module 1 according to Example 3. The fly-eye liquid crystal lens 100 and the fly-eye lens 4 are sequentially arranged above the imaging device 3. That is, the fly-eye liquid crystal lens 100 is disposed on the imaging device 3 side.

FIG. 52 is a sectional view showing the arrangement of the multieye camera module 1 according to Example 4. The fly-eye liquid crystal lens 100, the fly-eye lens 4, and fly-eye liquid crystal lens 100 are sequentially arranged above the imaging device 3. That is, the multieye camera module 1 according to Example 4 includes the two fly-eye liquid crystal lenses 100 so as to sandwich the fly-eye lens 4.

As described above, when forming the multieye camera module 1, it is possible to freely design the positions of the fly-eye liquid crystal lenses 100 and fly-eye lens 4. In addition, it is possible to implement the multieye camera module 1 by selecting one of Examples 1 to 4 in accordance with the characteristics of lens groups to be combined. FIG. 53 is a view for explaining the image captured by the multieye camera module 1. Imaging one object (a spherical object in FIG. 53) by using the multieye camera module 1 can obtain four image data with parallaxes from one image formed on the imaging device 3. Performing image processing of the four image data with parallaxes can generate a stereoscopic image.

(Effects)

As described in detail above, according to the eighth embodiment, it is possible to form the liquid crystal lens 100 into a fly-eye liquid crystal lens by providing the plurality of circular opening portions 121A for the electrode 121 of the liquid crystal lens 100. It is possible to change the focal lengths of the plurality of lenses of the fly-eye liquid crystal lens 100 by controlling voltages to the fly-eye liquid crystal lens 100.

In addition, it is possible to implement the multieye camera module 1 by combining the fly-eye liquid crystal lens 100 with the fly-eye lens 4 having a fixed focal length. A stereoscopic image can be obtained by performing image processing of a plurality of image data with parallaxes which are captured by the multieye camera module 1. In this case, although the fly-eye lens is used, using one imaging device 3 can downsize the multieye camera module 1.

In addition, as in the first embodiment, the multieye camera module 1 can be configured to have a focus adjustment function by using homogeneously aligned liquid crystal layers for the fly-eye liquid crystal lens 100. Furthermore, as in the second embodiment, the multieye camera module 1 can be configured to have an angle-of-view adjustment function by using homeotropically aligned liquid crystal layers for the fly-eye liquid crystal lens 100.

[Ninth Embodiment]

The ninth embodiment exemplifies the arrangement of a capsule type medical device 20. The capsule type medical device 20 is used by being swallowed by an object. This device forms an image of an observation region illuminated with a light source on the surface of the imaging device via a lens in the body cavity, processes the image, and transmits the resultant data as an image signal.

Figure 54:
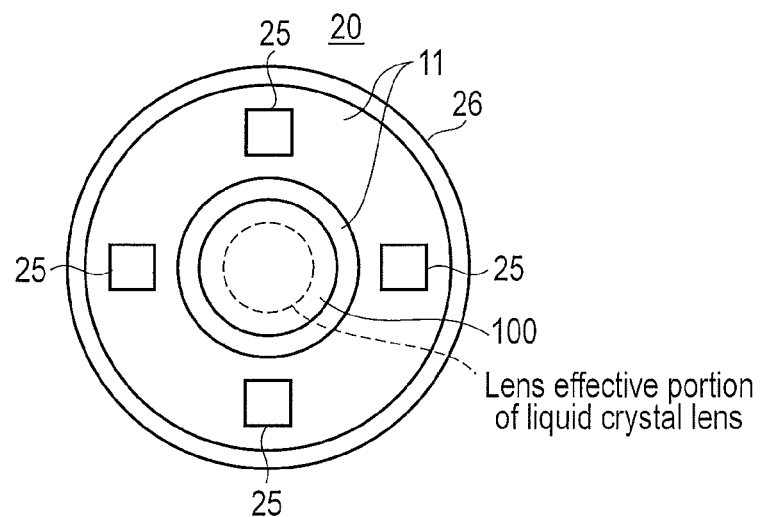
FIG. 54 is a top view showing the arrangement of a capsule type medical device according to the ninth embodiment.
Figure 55:
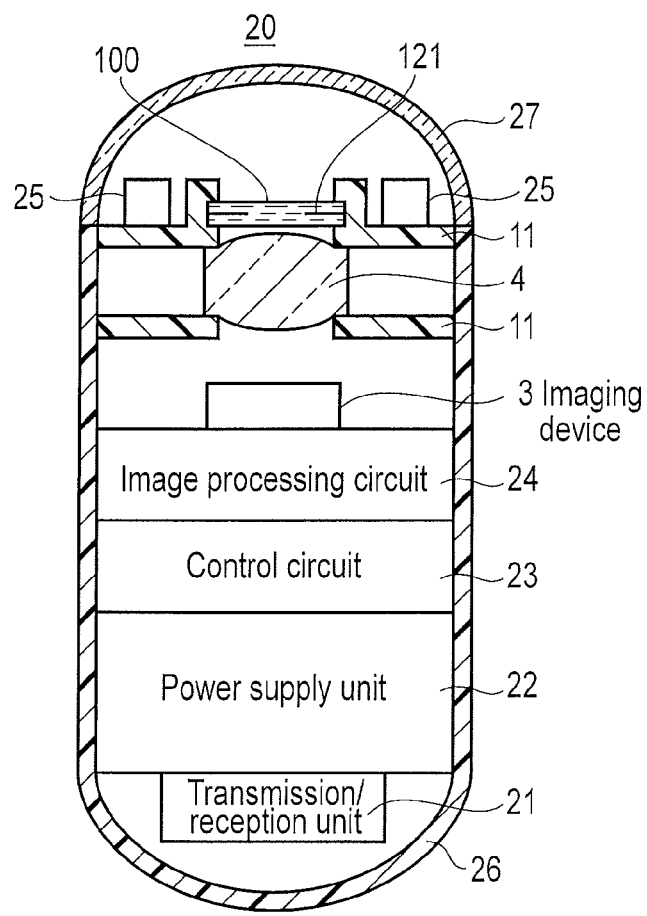
FIG. 55 is a sectional view showing the arrangement of a capsule type medical device according to Example 1.

FIG. 54 is a top view showing the arrangement of the capsule type medical device 20 according to the ninth embodiment. FIG. 55 is a sectional view showing the arrangement of the capsule type medical device 20 according to the ninth embodiment. The capsule type medical device 20 includes a transmission/reception unit 21, a power supply unit 22, a control circuit 23, an image processing circuit 24, an imaging device 3, a fixed lens group 4, a liquid crystal lens 100, a lens holder 11, and a plurality of illumination units (light source units) 25. The capsule type medical device 20 includes a plurality of circuit units described above housed in a sealed capsule formed by bonding an outer case 26 and a transparent cover 27.

The imaging device 3 is provided on a substrate (not shown). The fixed lens group 4 and the liquid crystal lens 100 are sequentially arranged above the imaging device 3. As the liquid crystal lens 100, the liquid crystal lens exemplified by the first embodiment is used. The lens holder 11 holds the fixed lens group 4 and the liquid crystal lens 100. The lens holder 11 is formed to hold the surroundings of the fixed lens group 4 and liquid crystal lens 100. For example, four illumination units 25 are provided on the uppermost portion of the lens holder 11. The light emitted from the illumination units 25 passes through the transparent cover 27 and illuminates the inner wall surface of a digestive organ (e.g., the small intestine or large intestine), in a predetermined range, through which the capsule type medical device 20 passes.

The transmission/reception unit 21 is constituted by an antenna, a switching circuit for switching between transmission and reception, a reception amplifier for amplifying a received signal, and the like. The transmission/reception unit 21 transmits image data and the like to the outside. The control signal received by the transmission/reception unit 21 is sent to the control circuit 23.

The power supply unit 22 supplies power to each circuit unit. As the power supply unit 22, for example, a battery is used. In addition, the power supply unit 22 may be formed from a circuit capable of noncontact power transmission such as an electromagnetic induction scheme. The image processing circuit 24 generates image data by using the image captured by the imaging device 3. The image processing circuit 24 also performs compression processing for image data.

The control circuit 23 controls each circuit unit in the capsule type medical device 20. The control circuit 23 also performs the processing of controlling an imaging timing and voltage control for the liquid crystal lens 100 based on instructions from the operator. The liquid crystal lens 100 is electrically connected to the control circuit 23 via wirings (not shown). The control circuit 23 includes the voltage control circuit 200. The control circuit 23 also includes a memory for storing image data.

Note that the positions of the liquid crystal lens 100 and fixed lens group 4 are not limited to those shown in FIG. 55 (Example 1), and various forms can be used. Another example of the arrangement of the capsule type medical device 20 will be described below.

FIG. 56 is a sectional view showing the arrangement of the capsule type medical device 20 according to Example 2. The liquid crystal lens 100 and the fixed lens group 4 are sequentially arranged above the imaging device 3. That is, the liquid crystal lens 100 is disposed on the imaging device 3 side.

FIG. 57 is a sectional view showing the arrangement of the capsule type medical device 20 according to Example 3. The liquid crystal lens 100, the fixed lens group 4, and the liquid crystal lens 100 are sequentially arranged above the imaging device 3. That is, the capsule type medical device 20 according to Example 3 includes the two liquid crystal lenses 100 so as to sandwich the fixed lens group 4.

The capsule type medical device 20 having the above arrangement can include a focus adjustment function and an angle-of-view adjustment function. The principles of the focus adjustment function and angle-of-view adjustment function are the same as those in the seventh embodiment. It is also possible to implement the capsule type medical device 20 having a focus adjustment function and an angle-of-view adjustment function by selecting one of Examples 1 to 3 in accordance with the characteristics of lens groups to be combined.

[10th Embodiment]

The 10th embodiment exemplifies the arrangement of a multieye capsule type medical device. FIG. 58 is a top view showing the arrangement of a multieye capsule type medical device 20 according to the 10th embodiment. FIG. 59 is a sectional view showing the arrangement of the multieye capsule type medical device 20 according to the 10th embodiment.

An imaging device 3 is provided on a substrate (not shown). A fly-eye lens 4 and a fly-eye liquid crystal lens 100 are sequentially arranged above the imaging device 3. As the fly-eye liquid crystal lens 100, the fly-eye liquid crystal lens exemplified by the eighth embodiment is used. A lens holder 11 holds the fly-eye lens 4 and the fly-eye liquid crystal lens 100.

The lens holder 11 is formed to hold the surroundings of the respective lenses of the fly-eye lens 4. The lens holder 11 is formed to hold regions corresponding to portions, of the upper and bottom surfaces of the fly-eye liquid crystal lens 100, on which an electrode 121 is formed. In other words, the lens holder 11 is formed to hold portions other than the lens effective portion of the fly-eye liquid crystal lens 100. For example, five illumination units 25 are provided on the uppermost portion of the lens holder 11. Other arrangements are the same as those in the ninth embodiment.

Note that the positions of the fly-eye liquid crystal lens 100 and fly-eye lens 4 are not limited to those shown in FIG. 59 (Example 1), and various forms can be used. Another example of the arrangement of the multieye capsule type medical device 20 will be described below.

FIG. 60 is a sectional view showing the arrangement of the multieye capsule type medical device 20 according to Example 2. The fly-eye liquid crystal lens 100 and the fly-eye lens 4 are sequentially arranged above the imaging device 3. That is, the fly-eye liquid crystal lens 100 is disposed on the imaging device 3 side.

FIG. 61 is a sectional view showing the arrangement of the multieye capsule type medical device 20 according to Example 3. The fly-eye liquid crystal lens 100, the fly-eye lens 4, and the fly-eye liquid crystal lens 100 are sequentially arranged above the imaging device 3. That is, the multieye capsule type medical device 20 according to Example 3 includes the two fly-eye liquid crystal lenses 100 so as to sandwich the fly-eye lens 4.

The multieye capsule type medical device 20 having the above arrangement can capture a plurality of image data (four image data in this embodiment) with parallaxes with respect to one object. Processing four image data with parallaxes which are captured by the multieye capsule type medical device 20 can generate a stereoscopic image.

It is possible to implement the multieye capsule type medical device 20 having the focus adjustment function and the angle-of-view adjustment function by selecting one of Examples 1 to 3 in accordance with the characteristics of lens groups to be combined.

11th Embodiment

In order to mount a liquid crystal lens in a compact camera module, it is necessary to electrically wire the connecting terminals of the liquid crystal lens to a peripheral circuit for liquid crystal lens control so as to avoid interference with the fixed portion of the fixed lens. As a method of electrically connecting the liquid crystal lens to the peripheral circuit for liquid crystal lens control, a connection method using lead wires may be used. In order to connect the liquid crystal lens to the peripheral circuit via lead wires, it is necessary to solder lead wires to the connecting terminals between the liquid crystal lens and the peripheral circuit. It is, however, not easy to solder lead wires to the liquid crystal lens and the peripheral circuit while the liquid crystal lens faces the peripheral circuit. Assume that lead wires are soldered in the step of incorporating the liquid crystal lens in the support body. In this case, if the support body is made of a plastic material, the heat generated at the time of soldering deforms the support body.

The 11th embodiment exemplifies an arrangement for electrically connecting the liquid crystal lens to the peripheral circuit for liquid crystal lens control. That is, the liquid crystal lens is electrically connected to the peripheral circuit by forming pipe-like holes through portions of the support body which holds the liquid crystal lens and the fixed lens and disposing spring-like conductive members in the pipe-like holes.

FIG. 62 is a perspective view schematically showing a liquid crystal lens 100. Connecting terminals 340 to 343 for connection to an external circuit are provided on the four corners of the liquid crystal lens 100.

Figure 63:
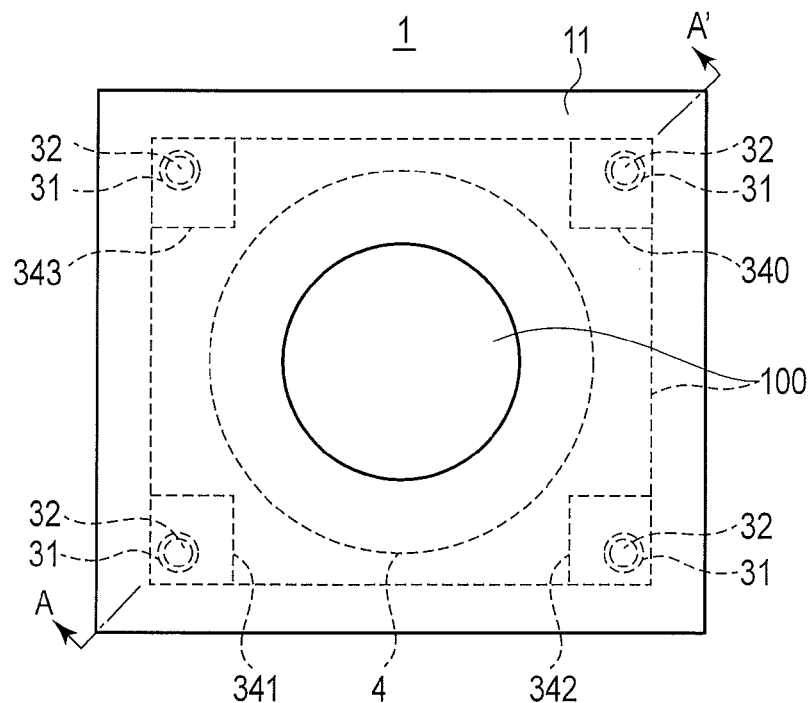
FIG. 63 is a plan view showing the arrangement of a camera module according to the 11th embodiment.
Figure 64:
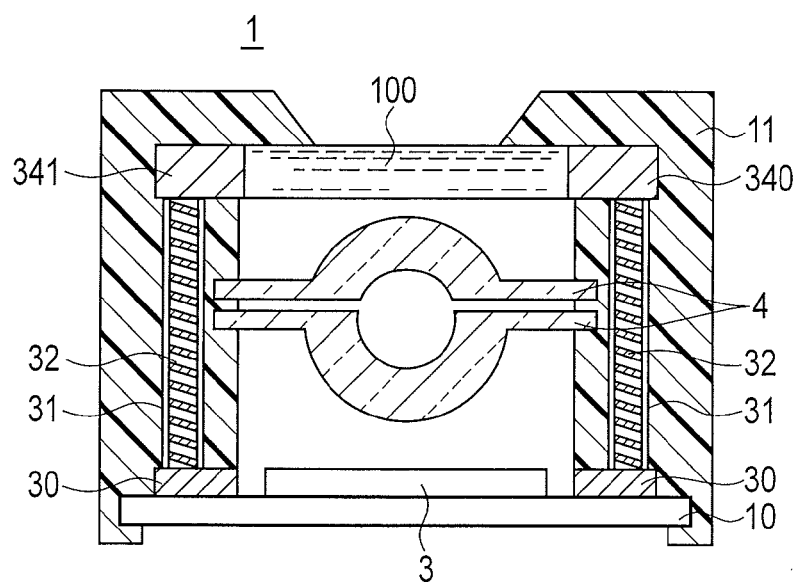
FIG. 64 is a sectional view taken along a line A-A' of the camera module shown in FIG. 63.

FIG. 63 is a plan view showing the arrangement of a camera module 1 according to the 11th embodiment. FIG. 64 is a sectional view taken along a line A-A' of the camera module 1 shown in FIG. 63.

An imaging device 33 and four external terminals 33 are provided on a peripheral circuit board 10. The imaging device 33 and the four external terminals 33 are electrically connected to the peripheral circuit board 10. The peripheral circuit board 10 includes a control circuit for driving and controlling the imaging device 33 and the liquid crystal lens 100 and a voltage control circuit 200. A fixed lens group 4 and the liquid crystal lens 100 are sequentially arranged above the imaging device 3. A lens holder (support body) 11 holds the fixed lens group 4 and the liquid crystal lens 100.

Arranging the rectangular liquid crystal lens 100 in FIG. 1 and the fixed lens group 4 on the same optical axis generates areas on the four corners of the liquid crystal lens 100 which do not interfere with the circular fixed lens group 4. Pipe-like holes 31 are formed through portions of the lens holder 11 which correspond to the areas which do not interfere with the fixed lens group 4. A spring-like conductive member 32 longer than the pipe-like hole 31 is disposed in the hole 31. With this arrangement, the connecting terminals of the liquid crystal lens 100 are electrically connected to the external terminals of the peripheral circuit board 10 by using the elastic force of the springs 32.

Note that elastic conductive rubber may be used for the spring-like conductive member 32. Alternatively, the spring 32 may be obtained by forming a metal, anisotropic conductive resin, or conductive resin material into a spring-like or columnar shape.

The liquid crystal lens 100 may be disposed in front of a fixed lens group 40 (FIG. 64), in the fixed lens group 4 (FIG. 65), or behind the fixed lens group 4 (FIG. 66). Referring to FIGS. 64, 65, and 66, the fixed lens group 4 is constituted by two lenses. However, this is merely an example, and the fixed lens group may be formed from one lens or may be constituted by three or more lenses.

(Effects)

As described in detail above, according to the 11th embodiment, it is possible to electrically connect the liquid crystal lens 100 to the peripheral circuit board 10 without using any lead wires and without performing any soldering step. In addition, it is possible to electrically connect the liquid crystal lens 100 to the peripheral circuit board 10 within the limited size of a compact camera module.

The present invention is not limited to the embodiments described above, and can be embodied by modifying constituent elements without departing from the gist of the invention. In addition, the above embodiments include inventions of various stages, and various inventions can be formed by proper combinations of a plurality of constituent elements disclosed in one embodiment or proper combinations of constituent elements disclosed in different embodiments. When, for example, the problems to be solved by the present invention can be solved and the effects of the invention can be obtained even if several constituent elements are omitted from all the constituent elements disclosed in each embodiment, an embodiment from which these constituent elements are omitted can be extracted as an invention.

What is claimed is:

1. A liquid crystal lens comprising:
a first liquid crystal cell including
a pair of a first transparent substrate and a second transparent substrate,
a first liquid crystal layer sandwiched between the first transparent substrate and the second transparent substrate, and
a first electrode arranged between the first transparent substrate and the first liquid crystal layer;
a second liquid crystal cell including
a pair of a third transparent substrate and a fourth transparent substrate,
a second liquid crystal layer sandwiched between the third transparent substrate and the fourth transparent substrate and aligned in a direction perpendicular to the first liquid crystal layer, and
a second electrode arranged between the fourth transparent substrate and the second liquid crystal layer; and
an intermediate layer including
an insulating layer sandwiched between the first liquid crystal cell and the second liquid crystal cell so as to be in contact with the second transparent substrate and the third transparent substrate, and
a third electrode provided on the second transparent substrate and including one or a plurality of opening portions, the insulating layer being on a surface of the third electrode facing away from the second transparent substrate,
a seal member bonding the first liquid crystal cell to the second liquid crystal cell, being on the third electrode and in contact with the third transparent substrate, and surrounding the insulating layer so as to be in contact with a side surface of the insulating layer.

2. The liquid crystal lens of claim 1, wherein
the first liquid crystal layer has homogeneous alignment in a first direction, and
the second liquid crystal layer has homogeneous alignment in a second direction perpendicular to the first direction.

3. The liquid crystal lens of claim 1, wherein
the first liquid crystal layer has homeotropic alignment such that liquid crystal molecules have pre-tilt angles in a first direction, and
the second liquid crystal layer has homeotropic alignment such that liquid crystal molecules have pre-tilt angles in a second direction perpendicular to the first direction.

4. The liquid crystal lens of claim 1, wherein
the first liquid crystal layer has splay alignment in a first direction, and
the second liquid crystal layer has splay alignment in a second direction perpendicular to the first direction.

5. The liquid crystal lens of claim 1, wherein a focal length changes in accordance with a phase difference between an alternating voltage to the first electrode and an alternating voltage to the second electrode.

6. The liquid crystal lens of claim 1, wherein a relative dielectric constant of the insulating layer is larger than a relative dielectric constant of glass.

7. The liquid crystal lens of claim 1, wherein the insulating layer comprises a resin dispersed with fine particles containing barium titanate as a main component.

8. The liquid crystal lens of claim 1, wherein the third electrode comprises a conductive material containing carbon.

9. The liquid crystal lens of claim 1, wherein an aberration between the first liquid crystal cell and the second liquid crystal cell in an aperture direction is not more than a pixel pitch.

10. The liquid crystal lens of claim 1, wherein a distance between a light output surface of the first liquid crystal layer and a light output surface of the second liquid crystal layer is not more than 500 µm.

11. The liquid crystal lens of claim 1, wherein
the second transparent substrate is processed to be thinner than the first transparent substrate, and
the third transparent substrate is processed to be thinner than the fourth transparent substrate.

12. The liquid crystal lens of claim 1, wherein a thickness of each of the second transparent substrate and the third transparent substrate is not more than 150 µm.

13. The liquid crystal lens of claim 1, further comprising a second seal member and a third seal member configured to seal the first liquid crystal layer and the second liquid crystal layer, respectively,
wherein each of the second seal member and the third seal member has a ring-like shape.

14. The liquid crystal lens of claim 1, further comprising a second seal member and a third seal member configured to seal the first liquid crystal layer and the second liquid crystal layer, respectively,
wherein each of the second seal member and the third seal member includes a first member having a ring-like shape and a second member having a rectangular shape and surrounding the first member.

15. The liquid crystal lens of claim 1, wherein a thickness of the third electrode is not more than 10 µm.

16. The liquid crystal lens of claim 1, wherein
the third electrode is provided on an insulating substrate, and
the insulating substrate is sandwiched between the first liquid crystal cell and the second liquid crystal cell by using the insulating layer as an adhesive.

17. The liquid crystal lens of claim 16, wherein the insulating substrate includes a first terminal electrically connected to the first electrode, a second terminal electrically connected to the second electrode, and a third terminal electrically connected to the third electrode.

18. The liquid crystal lens of claim 1, wherein
the third electrode includes the plurality of opening portions,
the plurality of opening portions have the same diameter, and
a plurality of lens portions corresponding to the plurality of opening portions have the same focal length.

19. A method of driving a liquid crystal lens defined in claim 1, comprising:
grounding the third electrode;
applying a first alternating voltage and a second alternating voltage to the first electrode and the second electrode, respectively; and
changing a focal length of the liquid crystal lens by changing a phase difference between the first alternating voltage and the second alternating voltage.

20. A lens unit comprising:
a liquid crystal lens defined in claim 1; and
a fixed lens arranged on an optical axis of the liquid crystal lens and having a fixed focal length,
wherein a focal point or an angle of view is adjusted by changing the focal length of the liquid crystal lens.

21. A lens unit comprising:
a liquid crystal lens defined in claim 1; and
a fly-eye lens arranged on an optical axis of the liquid crystal lens and having a fixed focal length,
wherein a focal point or an angle of view is adjusted by changing the focal length of the liquid crystal lens.

22. A camera module comprising:
a lens unit defined in claim 20;
an imaging device configured to receive light from the lens unit; and
a control circuit configured to control the liquid crystal lens and the imaging device.

23. A capsule type medical device comprising:
a lens unit defined in claim 20;
an imaging device configured to receive light from the lens unit;
a control circuit configured to control the liquid crystal lens and the imaging device; and
a capsule configured to seal the lens unit, the imaging device, and the control circuit.

24. The liquid crystal lens of claim 1, wherein each of the first through fourth transparent substrates is a glass substrate.

25. A liquid crystal lens comprising:
a first liquid crystal cell including
a pair of a first transparent substrate and a second transparent substrate,
a first liquid crystal layer sandwiched between the first transparent substrate and the second transparent substrate, and
a first electrode arranged between the first transparent substrate and the first liquid crystal layer;

a second liquid crystal cell including
- a pair of a third transparent substrate and a fourth transparent substrate,
- a second liquid crystal layer sandwiched between the third transparent substrate and the fourth transparent substrate and aligned in a direction perpendicular to the first liquid crystal layer, and
- a second electrode arranged between the fourth transparent substrate and the second liquid crystal layer; and an intermediate layer including
- an insulating layer sandwiched between the first liquid crystal cell and the second liquid crystal cell so as to be in contact with the second transparent substrate and the third transparent substrate, and
- a third electrode including one or a plurality of opening portions, wherein the first electrode includes a first electrode portion having a circular shape and a first terminal extracted from the first electrode portion to a corner of the first liquid crystal cell, the second electrode includes a second electrode portion having a circular shape and a second terminal extracted from the second electrode portion to a corner of the second liquid crystal cell, the third electrode includes a third electrode portion having a ring-like shape and a third terminal extracted from the third electrode portion to a corner of the first liquid crystal cell, and the first terminal, the second terminal, and the third terminal are arranged so as not to overlap each other.

26. The liquid crystal lens of claim 25, wherein each of the first liquid crystal cell and the second liquid crystal cell has a square planar shape.

27. A liquid crystal lens comprising:
a first liquid crystal cell including
- a pair of a first transparent substrate and a second transparent substrate,
- a first liquid crystal layer sandwiched between the first transparent substrate and the second transparent substrate, and
- a first electrode arranged between the first transparent substrate and the first liquid crystal layer;

a second liquid crystal cell including
- a pair of a third transparent substrate and a fourth transparent substrate,
- a second liquid crystal layer sandwiched between the third transparent substrate and the fourth transparent substrate and aligned in a direction perpendicular to the first liquid crystal layer, and
- a second electrode arranged between the fourth transparent substrate and the second liquid crystal layer; and an intermediate layer including
- an insulating layer sandwiched between the first liquid crystal cell and the second liquid crystal cell so as to be in contact with the second transparent substrate and the third transparent substrate, and
- a third electrode including one or a plurality of opening portions, wherein the third electrode is provided on an insulating substrate, the insulating substrate is sandwiched between the first liquid crystal cell and the second liquid crystal cell by using the insulating layer as an adhesive, and the insulating substrate includes a first terminal electrically connected to the first electrode, a second terminal electrically connected to the second electrode, and a third terminal electrically connected to the third electrode.

* * * * *